United States Patent
Lee et al.

(10) Patent No.: US 9,802,926 B2
(45) Date of Patent: Oct. 31, 2017

(54) ANHYDROUS CRYSTALLINE FREE BASE FORM OF 6-{2-[1-(6-METHYL-3-PYRIDAZINYL)-4-PIPERIDINYL]ETHOXY}-3-ETHOXY-1,2-BENZISOXAZOLE

(71) Applicant: Biota Pharmaceuticals, Inc., Alpharetta, GA (US)

(72) Inventors: Edward Lee, Alpharetta, GA (US); David McAllister, Notting Hill (AU); Andrew Trigwell, Notting Hill (AU); Robert Vincent Tuohy, III, Norristown, PA (US); Peter Snyder, Jr., Norristown, PA (US); Christa Leisa Frassetto, Norristown, PA (US)

(73) Assignee: AVIRAGEN THERAPEUTICS, INC., Alpharetta, GA (US)

( * ) Notice: Subject to any disclaimer, the term of this patent is extended or adjusted under 35 U.S.C. 154(b) by 0 days.

(21) Appl. No.: 14/916,373

(22) PCT Filed: Jun. 19, 2015

(86) PCT No.: PCT/US2015/036754
§ 371 (c)(1),
(2) Date: Mar. 3, 2016

(87) PCT Pub. No.: WO2015/196113
PCT Pub. Date: Dec. 23, 2015

(65) Prior Publication Data
US 2016/0194310 A1    Jul. 7, 2016

Related U.S. Application Data

(60) Provisional application No. 62/015,126, filed on Jun. 20, 2014.

(51) Int. Cl.
C07D 413/14    (2006.01)
A61K 47/10    (2017.01)
(Continued)

(52) U.S. Cl.
CPC .......... *C07D 413/14* (2013.01); *A61K 9/0095* (2013.01); *A61K 9/10* (2013.01);
(Continued)

(58) Field of Classification Search
CPC ...... A61K 31/501; A61K 47/10; A61K 47/12; A61K 47/14; A61K 47/26; A61K 47/36;
(Continued)

(56) References Cited

U.S. PATENT DOCUMENTS 8,580,791 B2    11/2013    Ryan et al.
2011/0144118 A1    6/2011    Ryan et al.
(Continued)

FOREIGN PATENT DOCUMENTS

WO    WO-02/50045    6/2002
WO    WO-2011/160191    12/2011

OTHER PUBLICATIONS

Moreton (chapter 3, from book, Pharmaceutical Suspensions, by Springer, 2010, ISBN 978/1/4419/1086/8.*
(Continued)

*Primary Examiner* — Savitha Rao
(74) *Attorney, Agent, or Firm* — B. Aaron Schulman, Esq.; Stites & Harbison, PLLC.

(57) ABSTRACT

A crystalline form of 6-{2-[1-(6-methyl-3-pyridazinyl)-4-piperidinyl]ethoxy}-3-ethoxy-1,2-benzoxazole is provided which is useful in the treatment of infections caused by Picornaviridae such as human rhinovirus (HRV), and in particular the crystal form is an anhydrous crystalline free base form of 6-{2-[1-(6-methyl-3-pyridazinyl)-4-piperidinyl]ethoxy}-3-ethoxy-1,2-benzoxazole. In addition, a
(Continued)

method of manufacturing the free base crystalline form is also provided, including a step of micronizing the compound particles, optionally using a wetting agent, as well as pharmaceutical compositions incorporating the free base crystalline form such as tablets or suspensions, and methods of therapeutic treatments using this form and pharmaceutical compositions thereof.

7 Claims, 32 Drawing Sheets

(51) Int. Cl.

| | | |
|---|---|---|
| *A61K 47/12* | (2006.01) | |
| *A61K 47/26* | (2006.01) | |
| *A61K 47/38* | (2006.01) | |
| *A61K 9/00* | (2006.01) | |
| *A61K 9/20* | (2006.01) | |
| *A61K 9/28* | (2006.01) | |
| *A61K 47/36* | (2006.01) | |
| *A61K 9/16* | (2006.01) | |
| *A61K 9/48* | (2006.01) | |
| *A61K 9/10* | (2006.01) | |
| *A61K 31/501* | (2006.01) | |
| *A61K 47/14* | (2017.01) | |

(52) U.S. Cl.
CPC .......... *A61K 9/1617* (2013.01); *A61K 9/1641* (2013.01); *A61K 9/1652* (2013.01); *A61K 9/20* (2013.01); *A61K 9/2013* (2013.01); *A61K 9/2018* (2013.01); *A61K 9/2054* (2013.01); *A61K 9/2059* (2013.01); *A61K 9/284* (2013.01); *A61K 9/4858* (2013.01); *A61K 31/501* (2013.01); *A61K 47/10* (2013.01); *A61K 47/12* (2013.01); *A61K 47/14* (2013.01); *A61K 47/26* (2013.01); *A61K 47/36* (2013.01); *A61K 47/38* (2013.01)

(58) Field of Classification Search
CPC ........ A61K 47/38; A61K 9/0095; A61K 9/10; A61K 9/1617; A61K 9/1641; A61K 9/1652; A61K 9/20; A61K 9/2013; A61K 9/2018; C07D 413/14
See application file for complete search history.

(56) References Cited

U.S. PATENT DOCUMENTS

| | | |
|---|---|---|
| 2011/0212966 A1 | 9/2011 | Watson et al. |
| 2011/0257192 A1 | 10/2011 | Lambert et al. |
| 2014/0179710 A1 | 6/2014 | Ryan et al. |

OTHER PUBLICATIONS

International Search Report for PCT/US2015/036754 dated Oct. 29, 2015.
Written Opinion of the International Searching Authority for PCT/US2015/036754 dated Oct. 29, 2015.
Feil et al. "An Orally Available 3-Ethoxybenzisoxazole Capsid Binder with Clinical Activity against Human Rhinovirus", ACS Med Chem Lett; (2012); vol. 3 No. 4: pp. 303-307.
First Examination Report dated Apr. 27, 2017 in New Zealand Application No. 728412.
Office Action dated May 16, 2017 in Japanese Application No. P2016-573021.
Noriaki, Hirayama, Handbook for Production of Crystals of Organic Compound, 2008, pp. 17-23, 37-40, 45-51 and 57-65.
Oshima, Hiroshi, Precipitation Behavior and Control of Crystal Polymorphism and Pseudo-Polymorphism, Pharm Stage, Jan. 15, 2007, vol. 6, No. 10, pp. 48-53.
Examination and Licensing Division of Pharmaceutical and Medical Safety Bureau of Ministry of Health, Labor and Welfare, Guidelines for Residual Solvents of Medical Products, PMSB/ELD Notification, 1998, No. 307, pp. 1-11, in particular, p. 5 and Table 3.
Feil et al., "An Orally Available 3-Ethoxybenzisoxazole Capsid Binder with Clinical Activity against Human Rhinovirus," *ACS Med. Chem. Lett.*, 2012, 3 (4), pp. 303-307, published Feb. 13, 2012.

\* cited by examiner

Exemplar Tablet Manufacturing Process

ANHYDROUS CRYSTALLINE FREE BASE FORM OF 6-{2-[1-(6-METHYL-3-PYRIDAZINYL)-4-PIPERIDINYL]ETHOXY}-3-ETHOXY-1,2-BENZISOXAZOLE

CROSS REFERENCE TO RELATED APPLICATIONS

This application claims the benefit of U.S. Provisional Application Ser. No. 62/015,126, filed Jun. 20, 2014, said application incorporated herein by reference.

FIELD OF THE INVENTION

The present invention relates in general to a crystalline free base form of 6-{2-[1-(6-methyl-3-pyridazinyl)-4-piperidinyl]ethoxy}-3-ethoxy-1,2-benzoxazole, and in particular to a novel anhydrous free base crystalline form thereof and its use in the manufacture of pharmaceutical compositions, a method of manufacturing the anhydrous crystalline form, pharmaceutical compositions incorporating the crystalline form, and methods of therapeutic treatments using this form and pharmaceutical compositions thereof.

BACKGROUND OF THE INVENTION

6-{2-[1-(6-Methyl-3-pyridazinyl)-4-piperidinyl]ethoxy}-3-ethoxy-1,2-benzoxazole is disclosed as Compound 35 in Applicant's earlier filed WO 2002/050045 (the '045 publication) and has the following general structure.

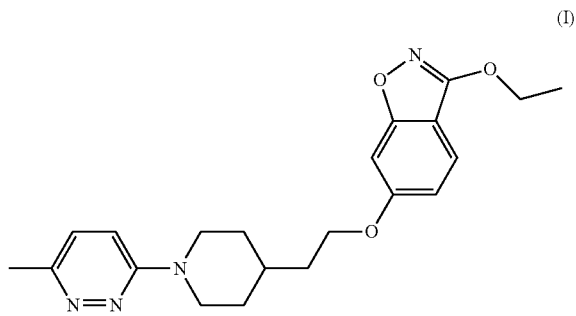 [SMILES: CCOc1noc2cc(OCCC3CCN(c4ccc(C)nn4)CC3)ccc12]

(I)

6-{2-[1-(6-Methyl-3-pyridazinyl)-4-piperidinyl]ethoxy}-3-ethoxy-1,2-benzoxazole is also known by its international non-proprietary Name (INN) as "vapendavir". Vapendavir is an antiviral agent which has been found, as previously described, to be particularly useful in the treatment and/or prevention of picornaviral infections such as human rhinovirus (HRV) and enteroviral infections as well as in the treatment and/or alleviation of symptoms of asthma and/or chronic obstructive pulmonary disease (COPD) and the reduction of the incidence of exacerbations and/or the prevention of exacerbations as asthma and/or COPD (see WO2002/050045, WO2011/127538 and WO2011/160191). Human rhinoviruses are a member of the genus Rhinovirus of the picornavirus family and are believed to be responsible for between 40 and 50% of common cold infections. Human rhinoviruses comprise a group of over 100 serotypically distinct viruses. Vapendavir has thus been shown to be effective against viruses of the Picornaviridae family which is also represented by the Enteroviruses. This genus includes polioviruses 1-3, coxsackieviruses A (23 serotypes) and B (6 serotypes), echoviruses (31 serotypes) and numbered enteroviruses 68-71. The clinical syndromes caused by enteroviruses include poliomyelitis, meningitis, encephalitis, pleurodynia, herpangina, hand foot and mouth disease, conjunctivitis, myocarditis and neonatal diseases such as respiratory illnesses and febrile illnesses. Viruses of the Picornavirus family are characterized by a single stranded (+) RNA genome encapsidated by a protein shell (or capsid) having pseudo icosahedral symmetry. The surface of the capsid contains "canyons" which surround each of the icosahedral fivefold axes, and it is believed that the cellular receptors bind to residues on the canyon floor.

One example in WO2002/050045, Example 6, describes the small-scale synthesis of 6-{2-[1-(6-methyl-3-pyridazinyl)-4-piperidinyl]ethoxy}-3-ethoxy-1,2-benzoxazole via a Mitsunobu coupling using a polymer-supported triphenylphosphine reagent and isolation in milligram quantity as a white powder following gradient elution column chromatography (see Example 6, page 36).

WO 2009/143571 (the '571 PCT publication) discloses particularly preferred salt forms of vapendavir, including a bis-dihydrogenphosphate crystalline salt form of vapendavir which is described as having desirable solubility and/or stability properties. However, following large-scale drug product manufacture, the inventors have discovered that this desirable crystalline salt form of vapendavir bisphosphate suffers from a phenomenon known as "process induced transformation" or "water induced phase changes" whereby the production of a significant amount of at least one other crystalline phase such as sesquiphosphate semihydrate was observed. The inventors also discovered that the square-planar crystal habit of the bis-dihydrogenphosphate salt of vapendavir had poor flow properties and a propensity to form agglomerates during manufacturing that in combination prevented reproducible formulation of the active drug.

In the art of compound formulation, manufacturing specific crystalline forms of compounds is a difficult pursuit and there is much uncertainty regarding the manufacture of a predictable and repeatable crystalline form. For example, the article "From Form to Function: Crystallization of Active Pharmaceutical Ingredients" by Variankaval et al., AIChE Journal, Vol. 54, No. 7, 1682-1688 (2008), herein incorporated by reference, describes the challenges in preparing desirable (pharmaceutical or other formulation) crystallizations with desired formulation properties. Problems that have been difficult to overcome in this field include undesirable qualities or excessive variability with regard to crystal shape and size, particle size distribution, solubility, and numerous other physical attributes necessary for efficient and useful manufacture of crystal forms, particularly as it relates to large scale production. As indicated in the article, most techniques in this field are "far from ready to handle the complexity of drug molecules being crystallized from real process streams in large-scale equipment." See Variankaval et al. at page 1687.

Even further, problems in stability in this field have made it difficult to come up with effective formulations that can be made into suspensions. Primarily with regard to the care of pediatric patients, suspensions are often a necessary avenue of treatment, but problems in developing an active ingredient of the proper stability and solubility has greatly limited the number of effective suspensions that can be prepared from the active ingredients.

In addition, there continues to be an unmet need for an anti-picornavirus compound that is particularly useful to treat and/or prevent infections including picornavirus infections such as those caused by human rhinovirus or enteroviruses and which is also safe and effective. Still further, there is a need to develop new pharmaceutical compositions that can readily be made into solid tablet form and other useful forms such as suspensions that can overcome previous problems with regard to manufacturing and repeatability such as uniform particle size necessary to ensure a safe and stable oral medication. Even further, there is a need for a new and useful form of medication which can be obtained in an efficient manufacturing process that can be used in large scale production while minimizing overall costs.

The present inventors have discovered an anhydrous, i.e. non-hydrate, crystalline form of 6-{2-[1-(6-methyl-3-pyridazinyl)-4-piperidinyl]ethoxy}-3-ethoxy-1,2-benzoxazole in its free base form, i.e. non-salt form, that is considered to possess one or more advantages including, for example, allowing for a more stable, efficient and less expensive large-scale manufacture of pharmaceutical compositions comprising 6-{2-[1-(6-methyl-3-pyridazinyl)-4-piperidinyl]ethoxy}-3-ethoxy-1,2-benzoxazole. In addition, the inventors have developed useful formulations for delivering the active ingredient, including tablets, capsules, suspensions and other forms.

SUMMARY OF THE INVENTION

There is provided an anhydrous, i.e. non-hydrate, free base crystalline form of 6-{2-[1-(6-methyl-3-pyridazinyl)-4-piperidinyl]ethoxy}-3-ethoxy-1,2-benzoxazole (or vapendavir) that will be useful in the treatment of infections including picornavirus infections such as those caused by human rhinovirus or enteroviruses, in treating, alleviating, preventing or reducing the symptoms or exacerbations of asthma or chronic obstructive pulmonary disease (COPD), or in treating, alleviating, preventing or reducing the symptoms of hand, foot and mouth disease.

There is also provided a process for the large-scale manufacture of 6-{2-[1-(6-methyl-3-pyridazinyl)-4-piperidinyl]ethoxy}-3-ethoxy-1,2-benzoxazole wherein the process comprises the step of forming an anhydrous crystalline free base form of 6-{2-[1-(6-methyl-3-pyridazinyl)-4-piperidinyl]ethoxy}-3-ethoxy-1,2-benzoxazole, such as those having the XRPD patterns such as shown in the attached figures. There is also provided a process for preparing anhydrous crystalline freebase 6-{2-[1-(6-methyl-3-pyridazinyl)-4-piperidinyl]ethoxy}-3-ethoxy-1,2-benzoxazole wherein the process includes a step of micronization which allows a more uniform average particle size and which provides a vapendavir in a form being more amenable to pharmaceutical compositions including tablets and suspensions.

There is also provided use of an anhydrous crystalline freebase form of 6-{2-[1-(6-methyl-3-pyridazinyl)-4-piperidinyl]ethoxy}-3-ethoxy-1,2-benzoxazole, such as those having the XRPD patterns as shown in the attached figures, in the manufacture of a pharmaceutical composition comprising 6-{2-[1-(6-methyl-3-pyridazinyl)-4-piperidinyl]ethoxy}-3-ethoxy-1,2-benzoxazole.

In one example, the pharmaceutical composition is a dry powder composition. In another example, the pharmaceutical composition is adapted for oral administration, particularly oral enteral administration. In this regard, the pharmaceutical composition may be formed into a suspension, tablet, caplet, or capsule, or other forms suitable for oral administration. Still other suitable forms will be those for other modes of administration to patients, for example, suppositories which may be preferred in certain pediatric cases, solutions for intravenous administration, and the like. The composition may also be in the form of a resuspendable sachet or powder.

In one example, the anhydrous crystalline form has a needle-like crystal habit. This differs greatly from other previous versions of vapendavir such as the phosphate salt which has a plate-like crystal habit.

In one exemplary embodiment, the XRPD profile of the anhydrous crystalline form of 6-{2-[1-(6-methyl-3-pyridazinyl)-4-piperidinyl]ethoxy}-3-ethoxy-1,2-benzoxazole shows major peaks (2θ) selected from the group consisting of the following approximate values: 4.5, 11.0, 13.6, 20.3, 20.6, 22.1, 23.1, 24.5, and 25.7. In addition, the anhydrous crystalline freebase form of 6-{2-[1-(6-methyl-3-pyridazin7yl)-4-piperidinyl]ethoxy}-3-ethoxy-1,2-benzoxazole may have an XRPD profile with peaks (d-spacing, Å) selected from the group consisting of approximately the following values: 19.5, 8.0, 6.5, 4.4, 4.3, 4.0, 3.8, 3.6, and 3.5.

The XRPD profile of the anhydrous crystalline form of 6-{2-[1-(6-methyl-3-pyridazinyl)-4-piperidinyl]ethoxy}-3-ethoxy-1,2-benzoxazole may also have peaks (2θ) selected from the group consisting of the following approximate values: 4.6, 10.4, 11.1, 13.7, 16.1, 16.7, 17.8, 20.4, 20.8, 21.6, 22.1, 22.3, 22.4, 23.4, and 24.8. The anhydrous crystalline form of 6-{2-[1-(6-methyl-3-pyridazinyl)-4-piperidinyl]ethoxy}-3-ethoxy-1,2-benzoxazole may also have an XRPD profile with peaks (d-spacing, Å) selected from the group consisting of approximately the following values: 19.2, 8.5, 8.0, 6.5, 5.5, 5.3, 5.0, 4.35, 4.27, 4.12, 4.03, 3.99, 3.96, 3.80 and 3.60.

In one exemplary embodiment of the present invention, the XRPD pattern of the present freebase crystalline form of vapendavir is shown in the attached FIG. 1. As indicated in FIG. 1, the following peaks were observed:

| No. | 2-theta (deg) | d (ang.) | Rel. height (a.u.) |
| --- | --- | --- | --- |
| 1 | 4.531 ± 0.003 | 19.487 ± 0.014 | 100.00 |
| 2 | 10.259 ± 0.009 | 8.616 ± 0.014 | 4.48 |
| 3 | 10.995 ± 0.003 | 8.040 ± 0.002 | 30.24 |
| 4 | 13.560 ± 0.004 | 6.5247 ± 0.018 | 48.49 |
| 5 | 15.18 ± 0.02 | 5.831 ± 0.008 | 1.70 |
| 6 | 15.942 ± 0.011 | 5.555 ± 0.004 | 4.74 |
| 7 | 16.59 ± 0.03 | 5.340 ± 0.009 | 1.54 |
| 8 | 17.002 ± 0.018 | 5.211 ± 0.005 | 3.18 |
| 9 | 17.70 ± 0.02 | 5.007 ± 0.006 | 1.80 |
| 10 | 18.33 ± 0.02 | 4.835 ± 0.006 | 1.58 |
| 11 | 20.265 ± 0.017 | 4.379 ± 0.004 | 9.20 |
| 12 | 20.624 ± 0.013 | 4.303 ± 0.003 | 8.52 |
| 13 | 21.43 ± 0.04 | 4.143 ± 0.007 | 1.69 |
| 14 | 22.124 ± 0.009 | 4.0146 ± 0.016 | 12.21 |
| 15 | 23.139 ± 0.012 | 3.8408 ± 0.019 | 8.84 |
| 16 | 23.857 ± 0.017 | 3.727 ± 0.003 | 4.72 |
| 17 | 24.531 ± 0.008 | 3.6259 ± 0.012 | 14.14 |
| 18 | 25.741 ± 0.009 | 3.4581 ± 0.012 | 9.56 |
| 19 | 27.420 ± 0.014 | 3.2501 ± 0.016 | 6.82 |
| 20 | 29.08 ± 0.03 | 3.069 ± 0.003 | 1.81 |
| 21 | 30.082 ± 0.017 | 2.9683 ± 0.016 | 0.89 |
| 22 | 31.86 ± 0.02 | 2.806 ± 0.002 | 1.98 |
| 23 | 32.68 ± 0.03 | 2.738 ± 0.003 | 1.21 |
| 24 | 34.61 ± 0.07 | 2.589 ± 0.005 | 0.57 |
| 25 | 35.64 ± 0.05 | 2.517 ± 0.004 | 0.25 |
| 26 | 37.18 ± 0.03 | 2.4162 ± 0.016 | 0.44 |
| 27 | 42.83 ± 0.02 | 2.1096 ± 0.011 | 1.54 |
| 28 | 43.72 ± 0.04 | 2.0687 ± 0.016 | 0.23 |
| 29 | 44.71 ± 0.05 | 2.025 ± 0.002 | 0.62 |
| 30 | 47.61 ± 0.04 | 1.9083 ± 0.014 | 1.05 |

In another example, the anhydrous crystalline (free base) form of 6-{2-[1-(6-methyl-3-pyridazinyl)-4-piperidinyl]ethoxy}-3-ethoxy-1,2-benzoxazole can be formulated into a pharmaceutical composition with the inclusion of a suitable pharmaceutical carrier. In certain examples, the pharmaceutical composition is a tablet or a suspension which may comprise the anhydrous crystalline form of 6-{2-[1-(6-methyl-3-pyridazinyl)-4-piperidinyl]ethoxy}-3-ethoxy-1,2-benzoxazole in an amount between about 40-60% by weight of the composition.

The pharmaceutical composition may be used to treat viral infections such as picornaviral or enteroviral infections. In addition, the freebase crystalline form of 6-{2-[1-(6-methyl-3-pyridazinyl)-4-piperidinyl]ethoxy}-3-ethoxy-1,2-benzoxazole may be used in the treatment and/or alleviation of symptoms of asthma and/or chronic obstructive pulmonary disease (COPD) and the reduction of the incidence of exacerbations and/or the prevention of exacerbations as asthma and/or COPD. In one example, the crystalline form of 6-{2-[1-(6-methyl-3-pyridazinyl)-4-piperidinyl]ethoxy}-3-ethoxy-1,2-benzoxazole may be used in a therapeutic treatment to be administered to individuals in need of treatment therefrom to treat and/or prevent various viral infections such as but not limited to picornaviruses such as human rhinovirus (HRV) or enteroviruses such as serotypes of one or more of the species Human enterovirus A, Human enterovirus B, Human enterovirus C and Human enterovirus D, including polioviruses and non-polioenteroviruses, which include coxsackieviruses A (such as serotypes 1-22 and 24), coxsackieviruses B (such as serotypes 1-6), echoviruses (such as serotypes 1-7, 9, 11-27, 29-34) and enteroviruses (such as serotypes EV68-71). In still other embodiments, the anhydrous crystalline form of vapendavir may be used in the treatment, alleviation and/or prevention of hand, foot and mouth disease.

The pharmaceutical composition may also be used in the treatment, alleviation, prevention or reduction of symptoms or exacerbations of asthma or chronic obstructive pulmonary disease (COPD), of which reduced lung function is typically symptomatic.

The anhydrous crystalline form of 6-{2-[1-(6-methyl-3-pyridazinyl)-4-piperidinyl]ethoxy}-3-ethoxy-1,2-benzoxazole may also be provided in a recrystallized form using an appropriate recrystallization solvent and conditions as set forth in more detail below. For example, 6-{2-[1-(6-methyl-3-pyridazinyl)-4-piperidinyl]ethoxy}-3-ethoxy-1,2-benzoxazole can be recrystallized from an alcohol, for example, ethanol, or any of a range of suitable slurry or recrystallization solvents as described further below.

The anhydrous crystalline form of 6-{2-[1-(6-methyl-3-pyridazinyl)-4-piperidinyl]ethoxy}-3-ethoxy-1,2-benzoxazole may also be provided in a micronized form with a very small particle sizes that facilitates its use in certain pharmaceutical compositions such as suspensions, as set forth in more detail below. For example, the micronized form of 6-{2-[1-(6-methyl-3-pyridazinyl)-4-piperidinyl]ethoxy}-3-ethoxy-1,2-benzoxazole can have average particle sizes of less than five microns. The micronization process can also employ a suitable wetting agent or surfactant which further enhances dissolution rate of vapendavir.

DETAILED DESCRIPTION

The present invention is directed to an anhydrous, free base crystalline form of 6-{2-[1-(6-methyl-3-pyridazinyl)-4-piperidinyl]ethoxy}-3-ethoxy-1,2-benzoxazole (known as "vapendavir"). The free base crystalline form of the invention may be used in pharmaceutical compositions to treat viral infections and other conditions as set forth in more detail below.

In one exemplary embodiment, the XRPD profile for the free base crystalline form of vapendavir can have the XRPD peaks as shown below:

| No. | 2-theta (deg) | d (ang.) | Rel. height (a.u.) |
|---|---|---|---|
| 1 | 4.531 ± 0.003 | 19.487 ± 0.014 | 100.00 |
| 2 | 10.259 ± 0.009 | 8.616 ± 0.008 | 4.48 |
| 3 | 10.995 ± 0.003 | 8.040 ± 0.002 | 30.24 |
| 4 | 13.560 ± 0.004 | 6.5247 ± 0.018 | 48.49 |
| 5 | 15.18 ± 0.02 | 5.831 ± 0.008 | 1.70 |
| 6 | 15.942 ± 0.011 | 5.555 ± 0.004 | 4.74 |
| 7 | 16.59 ± 0.03 | 5.340 ± 0.009 | 1.54 |
| 8 | 17.002 ± 0.018 | 5.211 ± 0.005 | 3.18 |
| 9 | 17.70 ± 0.02 | 5.007 ± 0.006 | 1.80 |
| 10 | 18.33 ± 0.02 | 4.835 ± 0.006 | 1.58 |
| 11 | 20.265 ± 0.017 | 4.379 ± 0.004 | 9.20 |
| 12 | 20.624 ± 0.013 | 4.303 ± 0.003 | 8.52 |
| 13 | 21.43 ± 0.04 | 4.143 ± 0.007 | 1.69 |
| 14 | 22.124 ± 0.009 | 4.0146 ± 0.016 | 12.21 |
| 15 | 23.139 ± 0.012 | 3.8408 ± 0.019 | 8.84 |
| 16 | 23.857 ± 0.017 | 3.727 ± 0.003 | 4.72 |
| 17 | 24.531 ± 0.008 | 3.6259 ± 0.012 | 14.14 |
| 18 | 25.741 ± 0.009 | 3.4581 ± 0.012 | 9.56 |
| 19 | 27.420 ± 0.014 | 3.2501 ± 0.016 | 6.82 |
| 20 | 29.08 ± 0.03 | 3.069 ± 0.003 | 1.81 |
| 21 | 30.082 ± 0.017 | 2.9683 ± 0.016 | 0.89 |
| 22 | 31.86 ± 0.02 | 2.806 ± 0.002 | 1.98 |
| 23 | 32.68 ± 0.03 | 2.738 ± 0.003 | 1.21 |
| 24 | 34.61 ± 0.07 | 2.589 ± 0.005 | 0.57 |
| 25 | 35.64 ± 0.05 | 2.517 ± 0.004 | 0.25 |
| 26 | 37.18 ± 0.03 | 2.4162 ± 0.016 | 0.44 |
| 27 | 42.83 ± 0.02 | 2.1096 ± 0.011 | 1.54 |
| 28 | 43.72 ± 0.04 | 2.0687 ± 0.016 | 0.23 |
| 29 | 44.71 ± 0.05 | 2.025 ± 0.002 | 0.62 |
| 30 | 47.61 ± 0.04 | 1.9083 ± 0.014 | 1.05 |

Figure 1A:
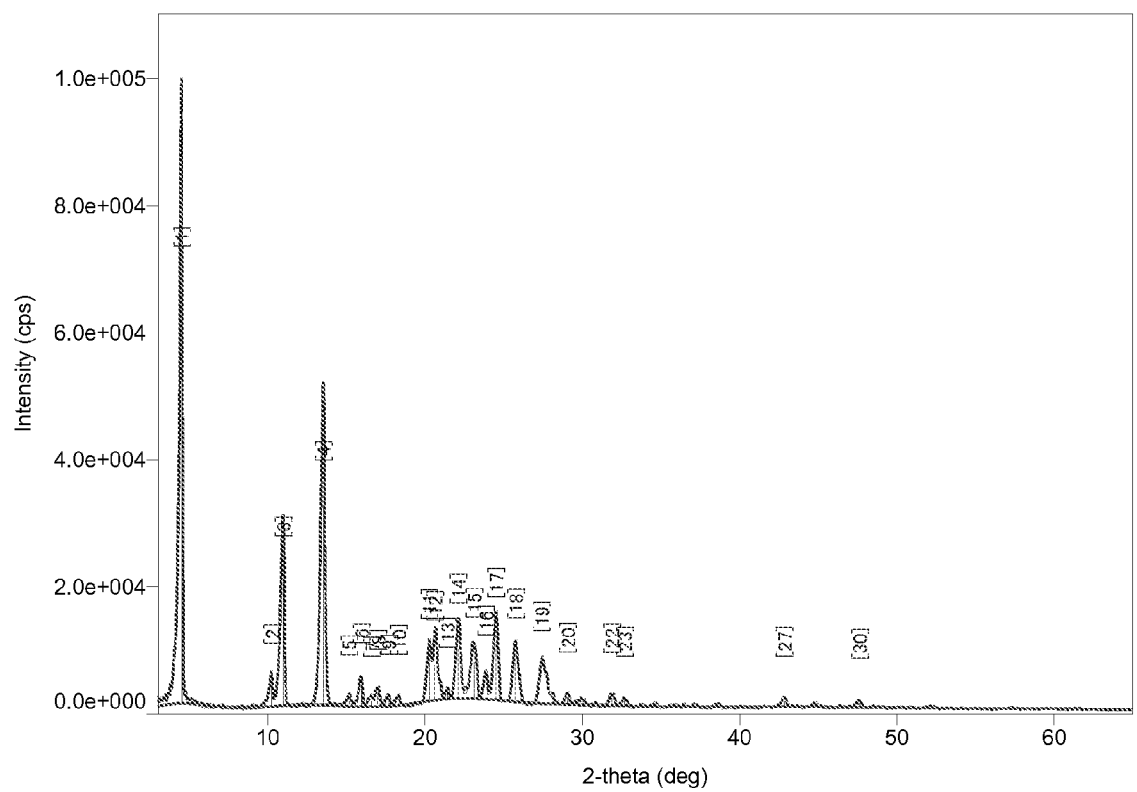
FIGS. 1A and 1B show an exemplary embodiment of the XRPD peaks for the anhydrous crystalline free base 6-{2-[1-(6-methyl-3-pyridazinyl)-4-piperidinyl]ethoxy}-3-ethoxy-1,2-benzoxazole in accordance with the present disclosure.
Figure 1B:
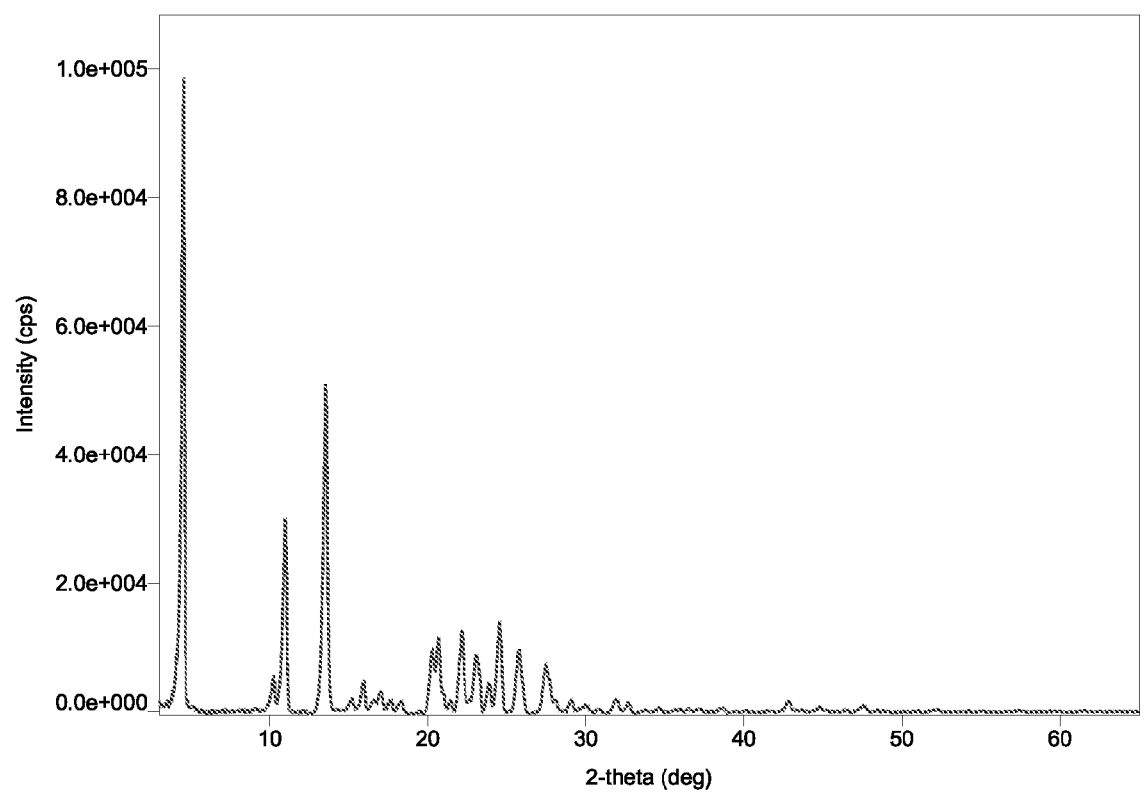

The XRDP pattern for this embodiment is shown in FIGS. 1A and 1B. As reflected therein, this embodiment includes major peaks at least in the approximate (2θ) values: 4.5, 11.0, 13.6, 20.3, 20.6, 22.1, 23.1, 24.5, and 25.7. In this pattern, the anhydrous crystalline form of 6-{2-[1-(6-methyl-3-pyridazinyl)-4-piperidinyl]ethoxy}-3-ethoxy-1,2-benzoxazole also shows a profile wherein the major peaks have the approximate (d-space, Å) following values: 19.5, 8.0, 6.5, 4.4, 4.3, 4.0, 3.8, 3.6, and 3.5.

Figure 2A:
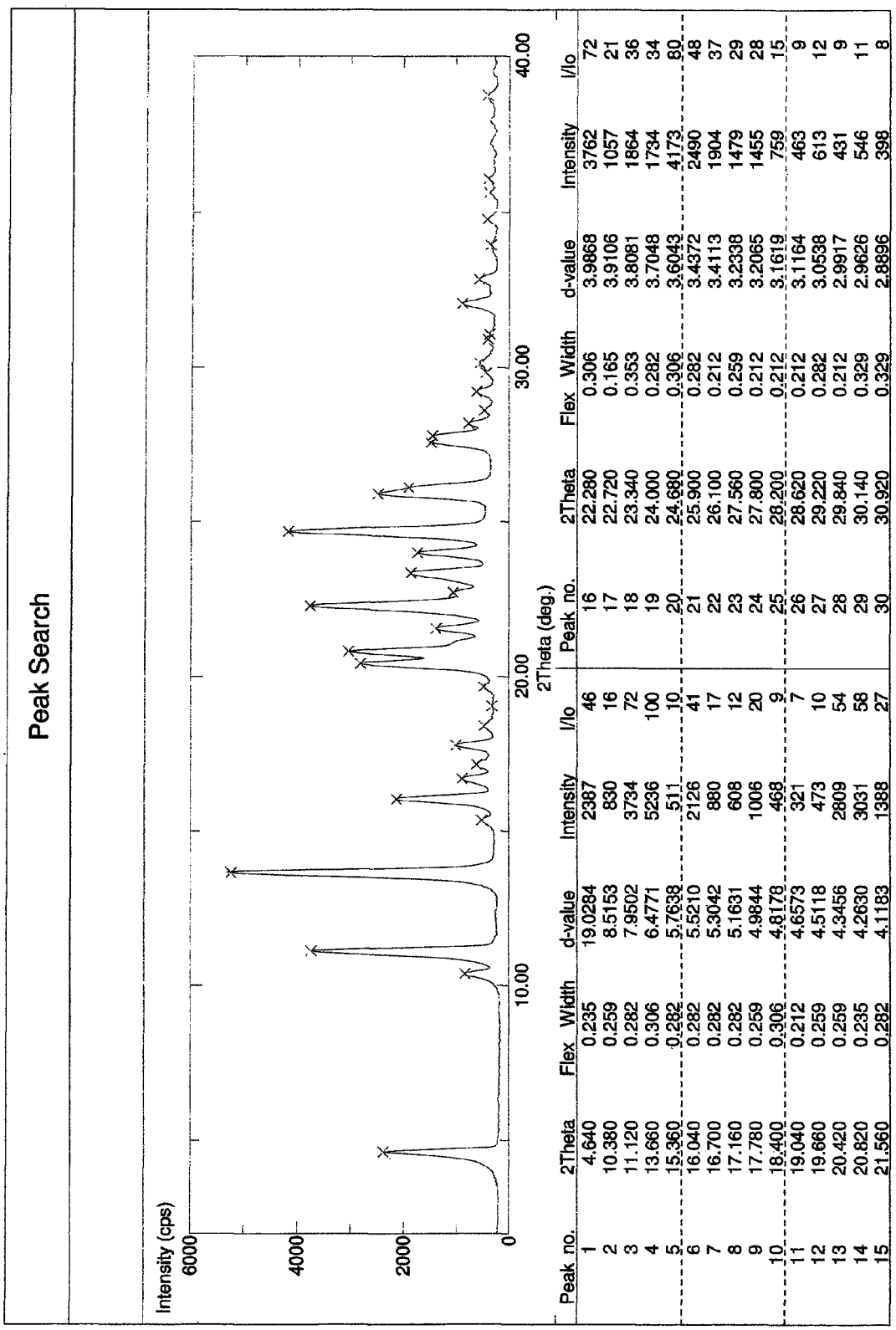
FIGS. 2A and 2B illustrate another exemplary embodiment of the XRPD peaks for the anhydrous crystalline free base 6-{2-[1-(6-methyl-3-pyridazinyl)-4-piperidinyl]ethoxy}-3-ethoxy-1,2-benzoxazole in accordance with the present disclosure.
Figure 2B:
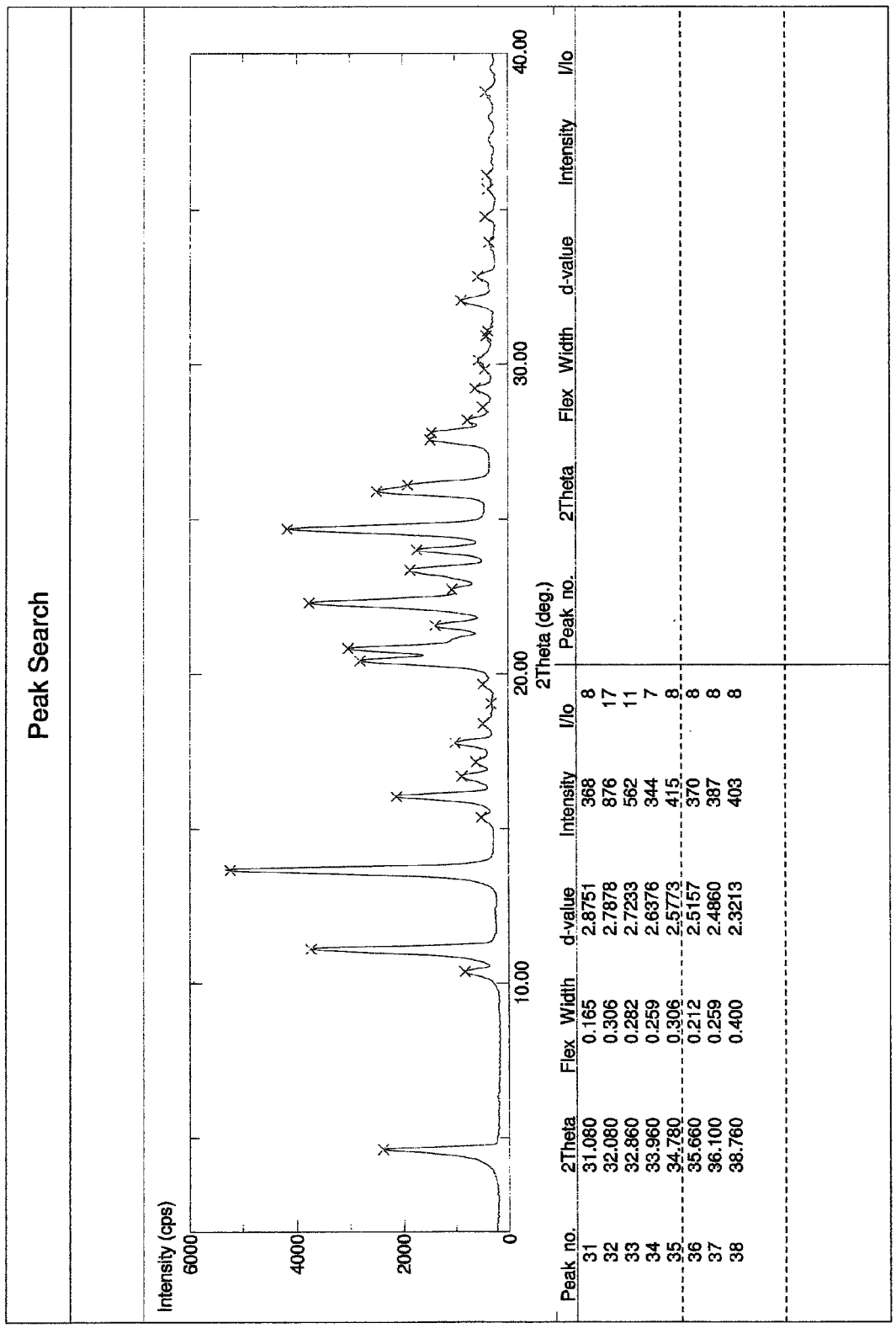
Figure 3:
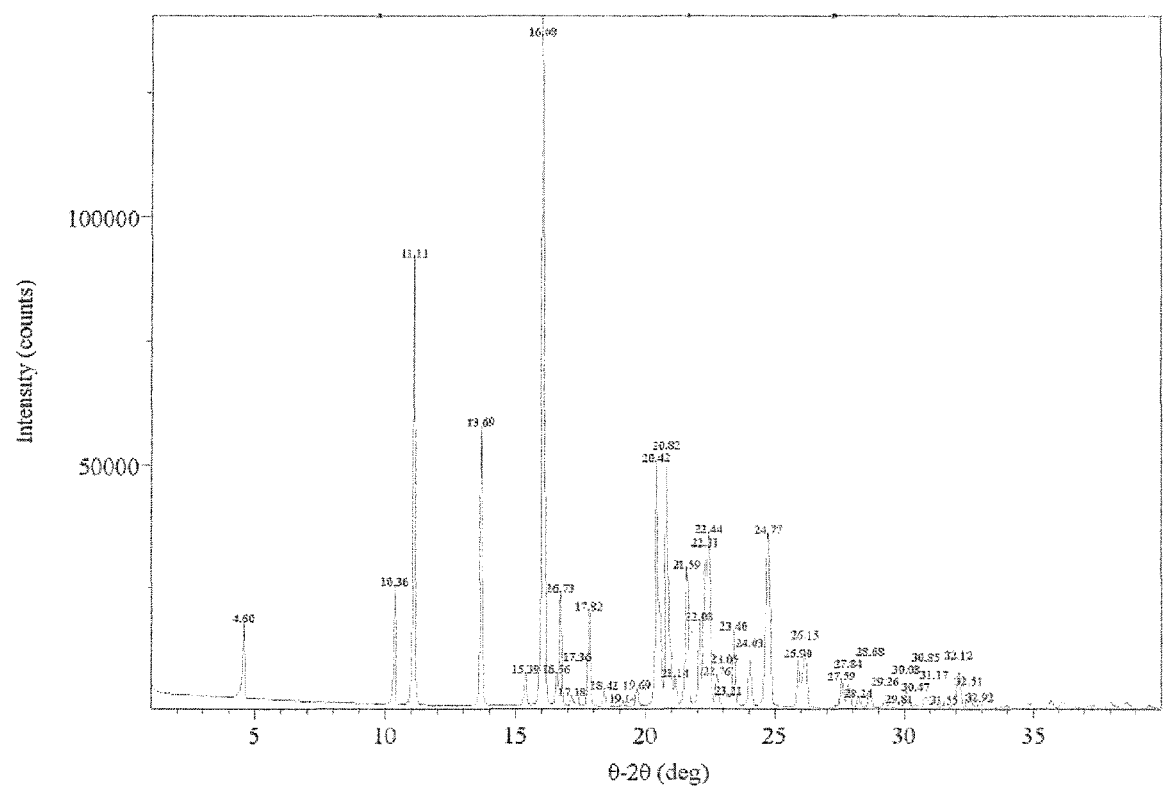
FIG. 3 is another XRPD peak (2θ) profile for the anhydrous crystalline free base 6-{2-[1-(6-methyl-3-pyridazinyl)-4-piperidinyl]ethoxy}-3-ethoxy-1,2-benzoxazole in accordance with the present disclosure.

In another exemplary embodiment, the free base crystalline form of vapendavir may also have the XRPD profile with peaks (d-space, Å) selected from the group consisting of approximately the following values: 19.2, 8.5, 8.0, 6.5, 5.5, 5.3, 5.0, 4.35, 4.27, 4.12, 4.03, 3.99, 3.96, 3.80 and 3.60. In one example, the crystalline 6-{2-[1-(6-methyl-3-pyridazinyl)-4-piperidinyl]ethoxy}-3-ethoxy-1,2-benzoxazole of the invention has the XRPD peaks (d-space, Å) profile as shown in FIGS. 2A, 2B and 3. Major peaks of this embodiment are shown in the Table below and include the approximate values of 19.2, 8.5, 8.0, 6.5, 5.5, 5.3, 5.0, 4.35, 4.27, 4.12, 4.03, 3.99, 3.96, 3.80 and 3.60.

The XRPD profile for the free base crystalline form of vapendavir can also be shown in terms of its 2θ peaks which are selected from the group consisting of approximately the following values: 4.6, 10.4, 11.1, 13.7, 16.1, 16.7, 17.8, 20.4, 20.8, 21.6, 22.1, 22.3, 22.4, 23.4, and 24.8. The crystalline freebase 6-{2-[1-(6-methyl-3-pyridazinyl)-4-piperidinyl]ethoxy}-3-ethoxy-1,2-benzoxazole of the invention may have the XRPD peaks (2θ) profile shown in FIGS. 2A, 2B and 3. Major peaks are shown in the Table below and include the approximate values of 4.6, 11.1, 13.7, 16.1, 20.4, 20.8, 22.3, and 24.8.

| °2θ | d space (Å) | Intensity (%) |
|---|---|---|
| 4.60 ± 0.20 | 19.221 ± 0.874 | 13 |
| 10.36 ± 0.20 | 8.537 ± 0.168 | 18 |
| 11.11 ± 0.20 | 7.961 ± 0.145 | 65 |
| 13.69 ± 0.20 | 6.469 ± 0.095 | 41 |
| 16.08 ± 0.20 | 5.513 ± 0.069 | 100 |
| 16.73 ± 0.20 | 5.299 ± 0.064 | 17 |
| 17.82 ± 0.20 | 4.979 ± 0.056 | 14 |
| 20.42 ± 0.20 | 4.349 ± 0.043 | 36 |
| 20.82 ± 0.20 | 4.266 ± 0.041 | 35 |
| 21.59 ± 0.20 | 4.116 ± 0.038 | 21 |
| 22.08 ± 0.20 | 4.026 ± 0.036 | 13 |
| 22.31 ± 0.20 | 3.985 ± 0.036 | 22 |
| 22.44 ± 0.20 | 3.961 ± 0.035 | 26 |
| 23.40 ± 0.20 | 3.802 ± 0.032 | 12 |
| 24.77 ± 0.20 | 3.595 ± 0.029 | 25 |

6-{2-[1-(6-Methyl-3-pyridazinyl)-4-piperidinyl]ethoxy}-3-ethoxy-1,2-benzoxazole in accordance with the invention has the formula (I) below:

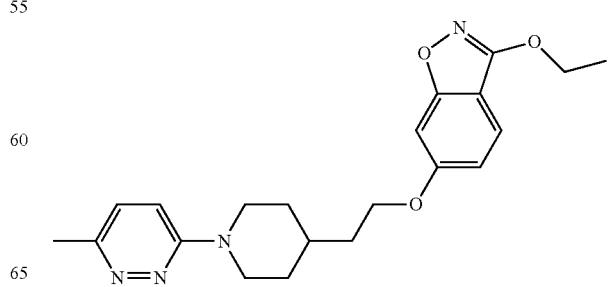

(I)

This compound can be formulated through a number of conventional ways, including those disclosed in WO 02/50045, incorporated herein by reference.

In one suitable method, the vapendavir compound may be formed by combining a compound having the formula:

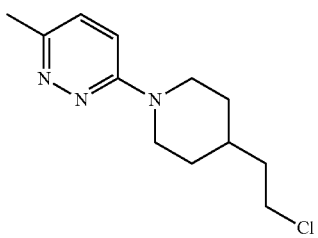 [SMILES: Cc1ccc(N2CCC(CCCl)CC2)nn1]

with a compound having the formula:

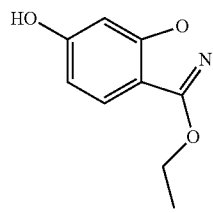

in a suitable reaction medium.

In some embodiments, these reactants can be combined using N-methylpyrolidine as a solvent. Other materials, such as cesium carbonate and potassium iodide, may be added, along with tetrahydrofuran, and water which may also be used as needed. Ethanol may be used to wash the filter cake obtained following the reaction. This reaction can directly produce the desired freebase crystal form of 6-{2-[1-(6-methyl-3-pyridazinyl)-4-piperidinyl]ethoxy}-3-ethoxy-1,2-benzoxazole. In another aspect of the invention, the freebase form of vapendavir, such as obtained above, may also be recrystallized in a number of suitable ways. In a further aspect of the invention, the freebase crystal form of the invention may be micronized to a very small particle size, as set forth in more detail below.

In one exemplary embodiment, the 6-{2-[1-(6-methyl-3-pyridazinyl)-4-piperidinyl]ethoxy}-3-ethoxy-1,2-benzoxazole may also be provided in a recrystallized form using a recrystallization process that includes a suitable solvent such as an alcohol, e.g., ethanol, or other suitable recrystallization solvent. In addition to an alcohol, such as ethanol, the recrystallization solvent may be any appropriate solvent suitable for slurry or recrystallization such as those selected from a group of suitable solvents that includes but is not limited to acetone, acetonitrile, dichloromethane, 1,4-dioxane, methyl ethyl ketone, 1-propanol, 2-propanol, tetrahydrofuran, and toluene. In addition, the crystalline free base form of vapendavir may be isolated from aqueous mixtures of one or more solvents, including acetone, acetonitrile, ethanol, 1-propanol and tetrahydrofuran.

In one exemplary process for recrystallizing the anhydrous crystalline free base form of the compound 6-{2-[1-(6-methyl-3-pyridazinyl)-4-piperidinyl]ethoxy}-3-ethoxy-1,2-benzoxazole in accordance with the present invention, recrystallization of vapendavir is obtained through the use of an active charcoal treatment and a series of solvents including dichloromethane and ethanol.

The procedure of recrystallization may include the steps of charging vapendavir, dichloromethane, and ethanol into a reactor and stirring the mixture at a suitable temperature (e.g., Ta=20° C.) and time. Optionally, active charcoal (which is later removed by filtration) may also be used to assist in impurity control. At the end of the initial steps, the suspension present can be filtered, using for example a nutsche filter and an inline filter (e.g., 0.45 m inline-filter). The filtered suspension may then be transferred to a clean reactor for additional steps. These may include rinse steps with a dichloromethane/ethanol solution (e.g., 1/1 v/v,) and transferring the rinsing solution via filters to the filtered reaction solution. Next, there can be multiple distillation steps including stepwise additions of ethanol and distillation under vacuum. Ultimately, the newly formed suspension may be heated, and the distillation completion can be confirmed, at which point the suspension is cooled and filtered to obtain the solid filter cake. The filter cake may be washed, e.g., with inline-filtered pre-cooled ethanol, then dried under a constant flow of nitrogen or air. Any wet cake is dried such as at maximum bath temperature (e.g., 45° C.) under vacuum until constant mass (e.g., loss of weight <0.5% of net weight in 30 min.).

In another exemplary method, vapendavir can be first prepared by charging 3-[4-(2-chloroethyl)-1-piperidyl]-6-methyl-pyridazine portion wise as a solid to a stirred mixture of 3-ethoxy-6-hydroxy-1,2-benzoxazole, caesium carbonate and potassium iodide in N-methylpyrrolidone at a suitable temperature such as 90° C. The mixture can be stirred at this temperature for an extended period, e.g., at least ten hours. Upon confirmation of reaction completion (>95% conversion by HPLC), the mixture can be cooled to a suitable temperature (e.g., 65° C.). A mixture of water and THF can be added to the suspension at this temperature (e.g., around 65° C., or in any event below 70° C. The mixture can be stirred for a suitable period of time (e.g., at least one hour) and then the mixture can be cooled (e.g., to 5° C.). The cooled suspension may then be filtered to obtain the filter cake, which is washed such as with a mixture of water and THF and then washed again with ethanol before drying to afford vapendavir.

The process to recrystallize the anhydrous free base crystal vapendavir when so desired may be accomplished by adding a mixture of dichloromethane and ethanol to the vapendavir and charcoal. The resulting mixture can be stirred (e.g., at 20° C.) before solids are removed by filtration, e.g., over a bed of filter aid and via an in-line filter. The filter cake can then be subsequently washed with a mixture of dichloromethane and ethanol, and the resulting filtrates can be solvent swapped to ethanol by concentration under reduced pressure until the level of dichloromethane is reduced (e.g., to below 1% w/w). This results in an ethanol suspension of vapendavir which can be heated to reflux before cooling, e.g., to 20° C.

In one suitable embodiment, wet milling is conducted by recirculation through an in-line pump equipped with a wet milling pump head, and then heated (e.g., to 40° C. for at least 10 minutes) before cooling (e.g., to 20° C.) followed by filtration. The resulting crystalline solid vapendavir can then be washed with ethanol or another suitable solvent and dried until the residual solvent content (e.g., of ethanol) is at a desired level, e.g., below around 1000 ppm.

In addition to an alcohol such as ethanol, a number of suitable recrystallization solvents can be used including acetone, acetonitrile, dichloromethane, 1,4-dioxane, methyl ethyl ketone, 1-propanol, 2-propanol, tetrahydrofuran, toluene and water. The crystal free base form of vapendavir in accordance with the invention can also be isolated from aqueous mixtures of acetone, acetonitrile, ethanol, 1-propanol and tetrahydrofuran.

As will be set forth in more detail below, the resulting vapendavir can then be micronized by processed such as wet milling or jet milling in which the particle size is reduced in a manner to ensure a more uniform particle size so as to maximize suitability and consistency of attributes of the drug substance for drug product manufacturing purposes. The micronization breaks the needles down to a smaller aspect ratio which is more suitable for drug product manufacturing, but does not affect the active ingredient and the therapeutic properties of the freebase crystal form.

In certain examples, the free base crystalline vapendavir of the invention may be micronized so as to reduce average particle size. In general, when first manufactured, the needle-like crystals of freebase vapendavir have a particle size of generally about 15 to 100 microns, with more particles falling within a size of about 70 to 100 microns, prior to micronizing. Through the micronization process, the particles are reduced to a smaller size, with average particles sizes being in the range of about 2 to 5 microns, and generally less than 5 microns. Micronization can be carried out using any suitable process such as the jet-milling or wet-milling processes known in the art. For example, the micronized version of the crystalline free base vapendavir may be obtained using conventional jet-milling equipment, such as the NGMP-2 jet mill manufactured by Sturdevant, Inc.

As a result of the above process, a compound comprising an anhydrous crystalline free base form of 6-{2-[1-(6-methyl-3-pyridazinyl)-4-piperidinyl]ethoxy}-3-ethoxy-1,2-benzoxazole, or 3-ethoxy-6-{2-[1-(6-methyl-pyridazin-3-yl)-piperidin-4-yl]-ethoxy}-benzo[d]isoxazole is produced, as shown as formula (I) above. This crystalline free base form is characterized by a needle-like crystal habit and as shown in the attached figures, this crystal form of 6-{2-[1-(6-methyl-3-pyridazinyl)-4-piperidinyl]ethoxy}-3-ethoxy-1,2-benzoxazole may have XRPD peaks (d-space, Å) selected from the group consisting of approximately the following values: 19.5, 8.0, 6.5, 4.4, 4.3, 4.0, 3.8, 3.6, and 3.5. The 2θ XRPD peaks may be selected from the group consisting of approximately the following values: 4.5, 11.0, 13.6, 20.3, 20.6, 22.1, 23.1, 24.5, and 25.7. The crystalline form may thus have the XRPD patterns as shown in FIGS. 1A, 1B, 2A, 2B and 3.

In another exemplary embodiment, the crystalline form of 6-{2-[1-(6-methyl-3-pyridazinyl)-4-piperidinyl]ethoxy}-3-ethoxy-1,2-benzoxazole in accordance with the present invention can be formulated into a pharmaceutical composition with the inclusion of a suitable pharmaceutical carrier. By suitable pharmaceutical carrier is meant any of a series of physical forms in which the active ingredient, in this case the crystalline free base form of 6-{2-[1-(6-methyl-3-pyridazinyl)-4-piperidinyl]ethoxy}-3-ethoxy-1,2-benzoxazole, may be administered in, including any of a wide variety of pharmaceutically acceptable carriers, diluents and/or excipients that are well known in the art.

Accordingly, the suitable pharmaceutical carrier may include solvents, coatings, antibacterial and antifungal agents, isotonic and absorption enhancing or delaying agents and the like. By "pharmaceutically acceptable" is generally understood to mean that said carrier is substantially compatible with the active ingredient and other ingredients in the composition or formulation and is substantially not deleterious to a patient undergoing treatment thereof. General examples of suitable carriers include maltodextrin, magnesium carbonate, magnesium stearate, talc, sugar, lactose, pectin, dextrin, starch, gelatin, tragacanth, cellulose, methylcellulose, silicified microcrystalline cellulose, mannitol, such as mannitol 400, glycolate, such as sodium starch glycolate, carboxymethylcellulose, such as sodium carboxymethylcellulose, a low melting wax, cocoa butter, and the like. Other suitable carriers include those materials by which the vapendavir may be formed as a solution, gel, cream, lotion, ointments, drops, and the like.

In general, the invention contemplates pharmaceutical carriers for delivery of the active vapendavir compound of the invention in any suitable manner, including oral, enteral, parenteral, topical, sublingual, intravenous, subcutaneous, intramuscular, percutaneous, and inhalation.

One suitable form of the pharmaceutical composition of the invention is a suspension. The ability to provide a pharmaceutical composition in the form of a suspension has been very important in particular with regard to pediatric medicine as this form may be necessary to administer the active ingredient to young patients. In this regard, the present inventors determined that a suitable form of crystalline free base vapendavir could be manufactured wherein the needle-like particles of the crystal were micronized to a smaller but more uniform particle size. The ability of the crystalline free base to be micronized and yet continue to maintain its active form was an improvement over previous forms of vapendavir such as the phosphate salt form which formed a plate-like crystal form and could not be micronized and maintain its active properties.

Accordingly, in another exemplary embodiment of the invention, the crystalline freebase vapendavir of the present invention is micronized so as to be formulated into a suspension.

In tests to assess the most favorable pH conditions, the crystalline free base vapendavir of the invention appeared to have the lowest solubility between pH 5.0-8.0 indicating that this pH range was the most desirable for a suspension formulation.

In certain examples, the suspension formulation may be obtained using any conventional ingredients useful in forming a pharmaceutical suspension. For example, in addition to the active ingredient, the suspension may include other materials such as buffers, preservatives and/or a viscosity-enhancer. In one exemplary embodiment, a citric acid buffer is used along with preservatives such as sodium benzoate, or preferably butylparaben, in order to more effectively preserve the composition at the target pH. Additionally, xanthan gum may be added to increase the viscosity of the suspension.

In order to achieve micronization, the crystalline free base vapendavir may be jet-milled using conventional jet-milling equipment, such as the NGMP-2 jet mill manufactured by Sturdevant, Inc. The resulting micronized crystalline free base vapendavir will have a more uniform particle size distribution, and the resulting form can have average particle sizes of less than 5 microns. Such smaller particle sizes can provide greater surface area to enhance dissolution and to give a free-base form that is stable to processing such as would be involved in a large scale operation.

As a result of the above processes, a pediatric suspension containing micronized crystalline freebase vapendavir may be obtained including desirable characteristics with regards to appearance, viscosity, pH, drug suspendability, and organoleptic properties. The following is an example of a suspension that will be useful in accordance with the invention:

| Sample | Formulation |
| --- | --- |
| BTA-798 Free Base (Micronized) | 2-3% |
| Microcrystalline Cellulose and Carboxymethylcellulose Sodium | 1-2% |
| Xanthan Gum | 0.01-1% |
| Polysorbate 80 | 0.01-1% |
| Propylene Glycol | 0.1-2% |
| Butylparaben | 0.001-0.05% |
| Glycerin | 1-10% |
| Flavor | 0.01-.50% |
| Sucrose | 30-50% |
| 0.1M Citric Acid | 40-60% |

As would be understood by one of ordinary skill in the art, a suitable suspension could be prepared using some or all of the ingredients in the above formulation, and ranges of these ingredients can vary beyond the exemplary examples provided above.

In another exemplary embodiment, the crystalline free base of the invention may be provided in the form of a resuspendable sachet or powder.

In another exemplary embodiment of the present invention, there is provided a solid pharmaceutical dosage form such as a tablet which could be suitably used for oral administration of the crystalline free base vapendavir of the invention. In such an embodiment, a micronized crystalline free base vapendavir is utilized in the preparation of the solid pharmaceutical dosage form. In preparing the dosage form, it was shown that replacing materials such as mannitol with a wetting agent or surfactant such as lauryl sulfate improved drug wetting and overall solubility. As would be understood by one of ordinary skill in the art, a wetting agent or surfactant is generally known as a chemical that can be added to a liquid to reduce its surface tension and make it more effective in spreading over and penetrating surfaces.

In this regard, the following formulations were tested for dissolution properties to assess the role of a wetting agent in preparation of a solid pharmaceutical dosage form:

TABLE 1

API Micronization and Dosage form Comparison:

| Sample | CU05-129-01 | CU05-129-12 | CU05-128-01 | CU05-128-12 |
| --- | --- | --- | --- | --- |
| Vapendavir Free Base (Non-Micronized) | — | — | 52.8% | 52.8% |
| Vapendavir Free Base (Micronized) | 52.8% | 52.8% | — | — |
| Sodium Lauryl Sulfate | 2.0% | 2.0% | 2.0% | 2.0% |
| Maltodextrin | 18.0% | 18.0% | 18.0% | 18.0% |
| Sodium Starch Glycolate (Explotab) | 6.0% | 6.0% | 6.0% | 6.0% |
| Silicified Microcrystalline Cellulose (Prosolv SMCC 90) | 20.5% | 20.5% | 20.5% | 20.5% |
| Magnesium Stearate | 0.8% | 0.8% | 0.8% | 0.8% |

The dissolution results showed negligible differences in the dissolution rates between the micronized and non-micronized vapendavir freebase formulations. Accordingly, in order to further improve surface wetting of the drug, formulations, a variety of surfactants/wetting agents were evaluated.

TABLE 2

Wetting Agent Comparison:

| Sample | CU05-095(4) | CLF13-113 | CLF13-112 | CLF13-114 | CU05-093 | CLF13-115 | CU05-128-12 |
| --- | --- | --- | --- | --- | --- | --- | --- |
| Vapendavir Free Base (Non-Micronized) | — | 67.0% | 67.0% | 67.0% | 44.5% | 67.0% | 52.8% |
| Vapendavir Phosphate Salt | 68.1% | — | — | — | — | — | — |
| Poloxamer (Kolliphor P188) | — | 25.4% | — | — | — | — | — |
| Sodium Lauryl Sulfate | — | — | — | — | — | — | 2.0% |
| Soluplus | — | — | — | 25.4% | — | — | — |
| Providone K29/32 | — | — | — | — | — | 25.4% | — |
| Polysorbate 80 | — | — | 2.5% | — | — | — | — |
| Maltodextrin | — | — | 22.8% | — | — | — | 18.0% |
| Sodium Starch Glycolate (Explotab) | — | 7.6% | 7.6% | 7.6% | — | 7.6% | 6.0% |
| SMCC 90 | — | — | — | — | — | — | 20.5% |
| Magnesium Stearate | — | — | — | — | — | — | 0.8% |
| Dextrose, Anhydrous | 31.9% | — | — | — | 55.5% | — | — |

The testing showed that the formulations with poloxamer and polysorbate 80 had the most dramatic effect on dissolution rate. Soluplus provided a modest improvement on the dissolution rate and povidone K29/32 did not improve the dissolution rate. This was most likely due to slow disintegration caused by the formation of a hydrogel inside the dissolution basket. The infinity point data supports the theory that the slow dissolution profile observed for the povidone formulation was caused by slow disintegration because the drug release at the infinity point was comparable to other wetting agents. The increased basket speed expedited the disintegration of the hydrogel and allowed the drug to release into solution.

One of the wetting agents that was evaluated was poloxamer, and formulations in accordance with the present invention prepared to evaluate the use of poloxamer with micronized and non-micronized crystal free base vapendavir. In addition, formulations were prepared to evaluate various levels of poloxamer, as set forth in the table below

TABLE 3

Micronized API and Poloxamer Level Comparison

| Sample | CU05-095(4) | CLF13-113 | PS01-08 | PS01-12 |
|---|---|---|---|---|
| Vapendavir Free Base (Non-Micronized) | — | 67.0% | — | 76.7% |
| Vapendavir Free Base (Micronized) | — | — | 67.0 % | — |
| Vapendavir Phosphate Salt | 68.1% | — | — | — |
| Poloxamer (Kolliphor P188) | — | 25.4% | 25.4% | 14.5% |
| Sodium Starch Glycolate (Explotab) | — | 7.6% | 7.6% | 8.7% |
| Dextrose, Anhydrous | 31.9% | — | — | — |

Figure 4:
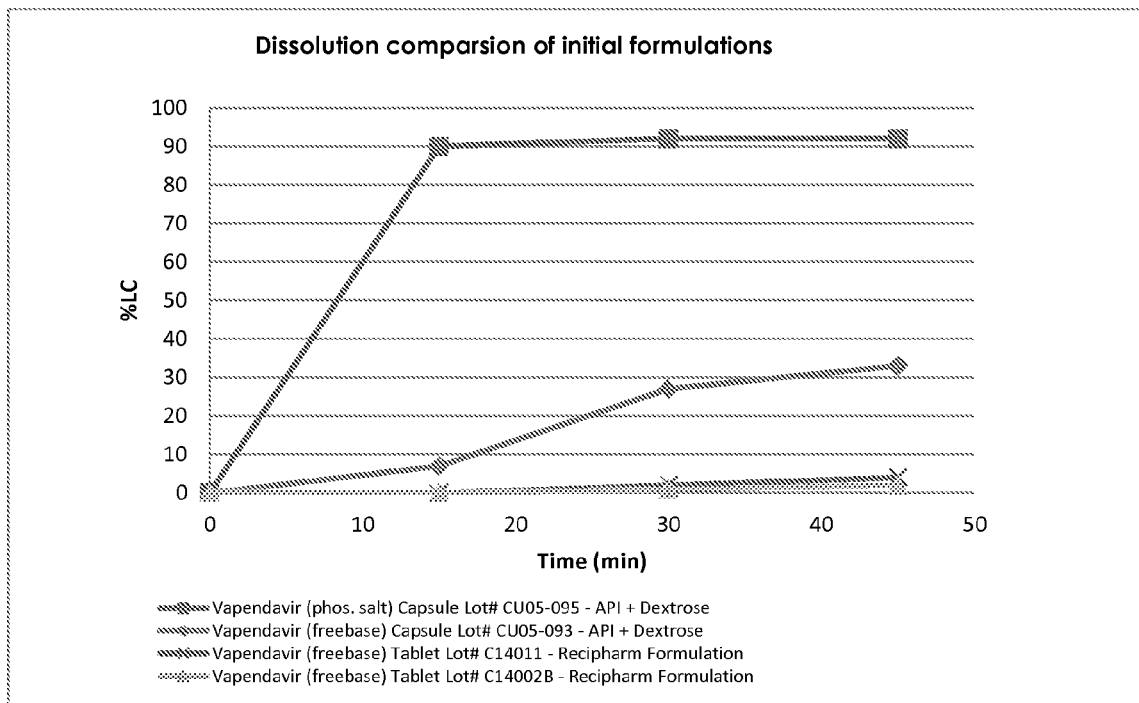
FIG. 4 is a graph showing a dissolution comparison of initial formulations.
Figure 5:
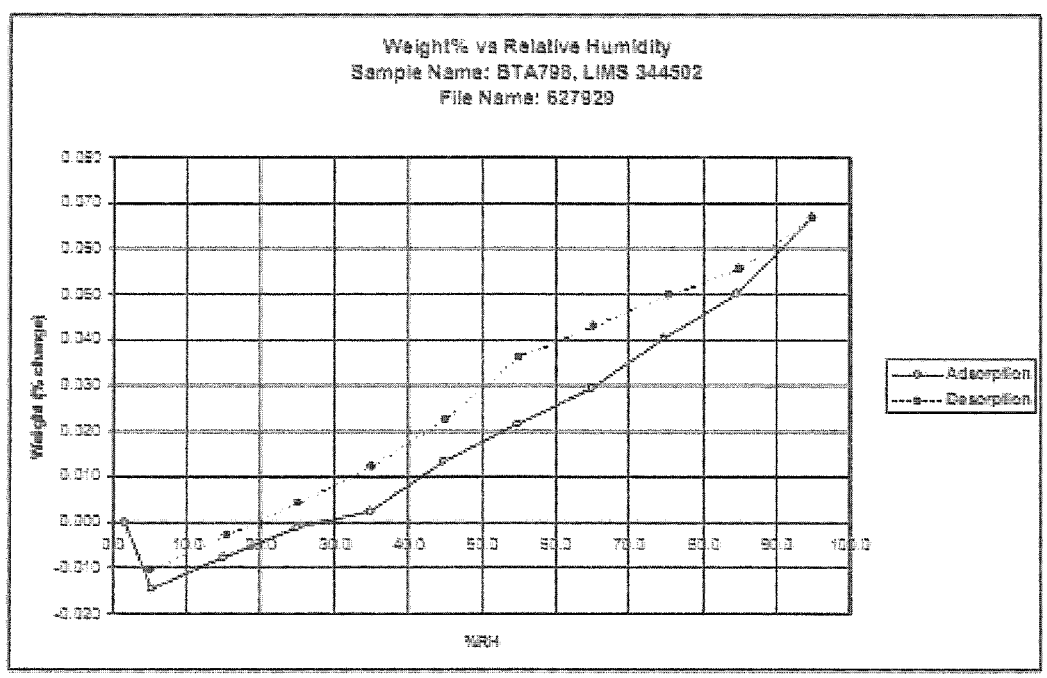
FIG. 5 is a dynamic vapor sorption plot graph showing weight percent change with relative humidity characteristics of the anhydrous crystalline free base 6-{2-[1-(6-methyl-3-pyridazinyl)-4-piperidinyl]ethoxy}-3-ethoxy-1,2-benzoxazole in accordance with the present disclosure.
Figure 6:
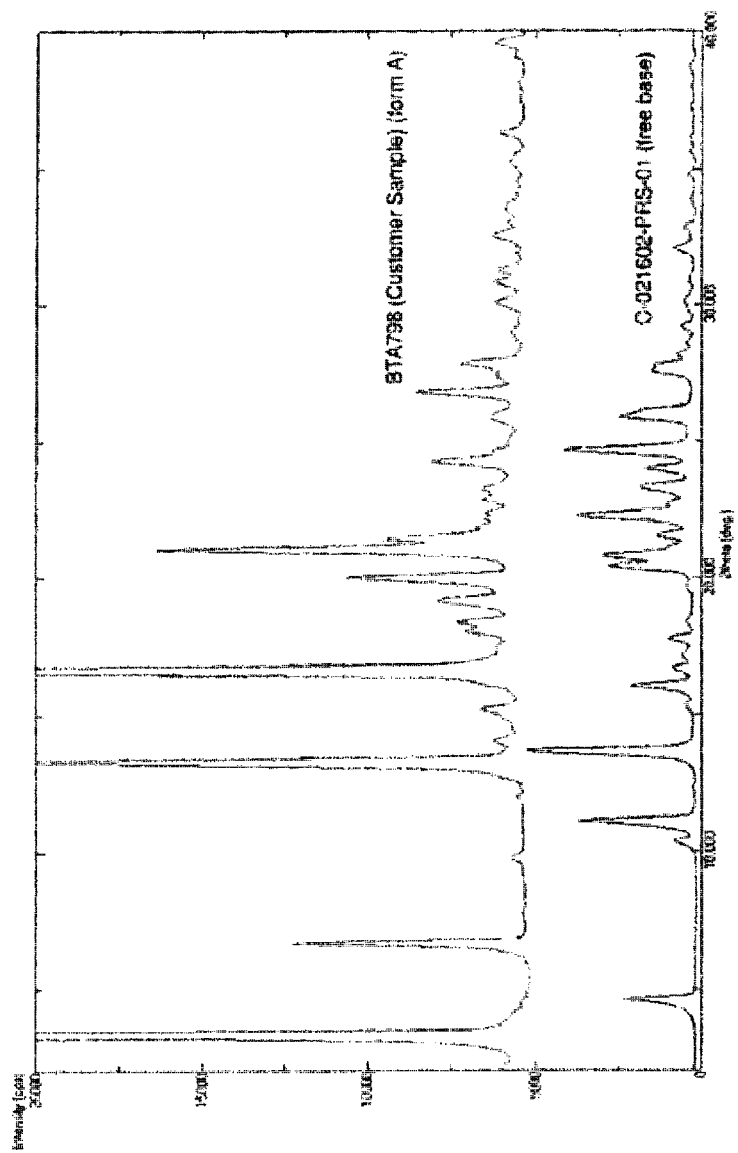
FIG. 6 is a chart showing an XRPD comparison between the anhydrous crystalline free base 6-{2-[1-(6-methyl-3-pyridazinyl)-4-piperidinyl]ethoxy}-3-ethoxy-1,2-benzoxazole in accordance with the present disclosure and the prior bis-dihydrogen phosphate salt form of vapendavir.

A dissolution comparison based on micronized and poloxamer level is shown in the accompanying FIG. 4.

There was no difference in the dissolution profiles between the different levels of poloxamer indicated the poloxamer use level can be reduced in the formulation. Thus, one can minimize the size of the final dosage form to assist in potential compliance with drug regulations. Further, an infinity point determination showed the formulation using the micronized vapendavir freebase releases to a greater extent than the formulation contain non-micronized material.

The dissolution rate and extent of vapendavir freebase solid oral formulations has been significantly increased over previously manufactured tablet formulations. Exemplary lead and back-up granulation formulations are listed below:

| Sample | Lead formulation | Backup formulation |
|---|---|---|
| Vapendavir freebase (micronized) | 70-80% | 60-70% |
| Poloxamer (Kolliphor P188) | 10-20% | — |
| Sodium Starch Glycolate (Explotab) | 5-10% | 5-10% |
| Polysorbate 80 | — | 1-4% |
| Maltodextrin | — | 15-25% |

In accordance with the above tests, it was thus shown that the addition of a wetting agent in the micronization process further assisted in obtaining a suitable pharmaceutical composition with the crystalline free base vapendavir of the present invention and is another useful step in developing a suitable tablet form of the invention.

Another exemplary advantage of the present crystalline form of 6-{2-[1-(6-methyl-3-pyridazinyl)-4-piperidinyl]ethoxy}-3-ethoxy-1,2-benzoxazole is that the physical size or mass of a tablet containing this new crystal form is less than that of the bis-phosphate form due to the present crystalline form having a lower molecular weight than the phosphate salt form. Accordingly, as indicated above, one exemplary embodiment of the invention is one wherein 6-{2-[1-(6-methyl-3-pyridazinyl)-4-piperidinyl]ethoxy}-3-ethoxy-1,2-benzoxazole is formed into a tablet.

In one exemplary example, the pharmaceutical composition of anhydrous crystalline fee base vapendavir is a dry powder composition. In another example, the pharmaceutical composition is adapted for oral administration, particularly oral enteral administration. In this regard, once again the pharmaceutical composition may be formed into a tablet or capsule. The composition may also be in the form of a resuspendable sachet or powder.

Figure 8:
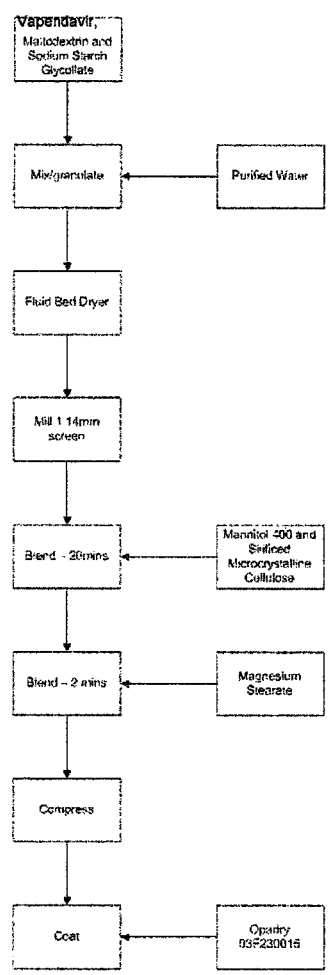
FIG. 8 shows one exemplar tablet manufacturing process which may be used to produce a pharmaceutical composition, a composition including the active ingredient of crystalline 6-{2-[1-(6-methyl-3-pyridazinyl)-4-piperidinyl]ethoxy}-3-ethoxy-1,2-benzoxazole free base with a suitable pharmaceutical carrier.

In another exemplary example, the anhydrous free base crystal form of vapendavir may be formed into a tablet suitable for oral administration to a patient in need thereof. An exemplary process for forming the tablet is shown in the schematic drawing of FIG. 8. In this exemplary process, the free base crystal vapendavir is combined with maltodextrin, sodium starch and suitable glycolates into a mixture to which purified water is added, and the ingredients are mixed and granulated and then fed into a fluid bed dryer to be dried. Following drying, the components are milled by passage through a screen, followed by blending of the screened ingredients with suitable agents such as mannitol 400 and silicified microcrystalline cellulose. Next, the components are further blended with magnesium stearate for a suitable time and then compressed and coated to produce the final tablet. The tablet may be coated with any suitable pharmaceutically acceptable coating well known in the industry including the poly(vinyl alcohol) or PVA coatings such as the Opadry coatings, e.g., Opadry 03F2300015. These suitable polymeric coatings generally include PVA and polyethylene glycol (PEG) which is used as a plasticizer to enhance film flexibility of PVA.

The tablet in accordance with the invention will have a dosage of the active ingredient in an amount generally prepared for oral administration, e.g., 100 mg, 200 mg, 300 mg, 500 mg, etc. In an exemplary embodiment, such a tablet may have vapendavir in the range of 20 to 80 percent by weight, or 40 to 70 percent by weight, or 54 to 60 percent by weight, with the balance being formed by suitable pharmaceutically acceptable vehicles, excipients and/or carriers. One suitable tablet with a 300 mg dosage of vapendavir may have the following ingredients:

| Excipient | % w/w |
|---|---|
| Vapendavir free base | 56 |
| Maltodextrin | 20 |
| Silicified Microcrystailine cellulose | 14 |
| Mannitol 400 | 6 |
| Sodium Starch glycolate | 1.5 |
| Mag Stearate | 0.7 |
| Opadry (Orange) | qs |

Further, an additional advantage of the present crystalline form is that since it is in an anhydrous form, the new crystalline 6-{2-[1-(6-methyl-3-pyridazinyl)-4-piperidinyl]ethoxy}-3-ethoxy-1,2-benzoxazole does not absorb water and resists changing form during pharmaceutical formulation as observed when using the bis-dihydrogenphosphate form.

Because of the novel crystalline free base form, the 6-{2-[1-(6-methyl-3-pyridazinyl)-4-piperidinyl]ethoxy}-3-ethoxy-1,2-benzoxazole of the present invention can provide improved properties in terms of stability and flowability. It also may provide a form of 6-{2-[1-(6-methyl-3-pyridazinyl)-4-piperidinyl]ethoxy}-3-ethoxy-1,2-benzoxazole that is easy to manufacture and has suitable characteristics to be incorporated into a solid tablet form or a suspension more efficiently and effectively than the prior art. Still further, benefits and advantages of the invention may include improved treatment of a picornavirus such as HRV because of the potential improved patient adherence due to smaller tablet sizes for the equivalent dose of the freebase vapendavir of the present invention versus the bis dihydrogenphosphate form used in the prior art.

The new crystalline form of the free base of vapendavir constitutes the lowest energy/most thermodynamically stable form of vapendavir and shows no hydrate formation when recrystallization is performed in the aqueous solvent systems. This form is thus a non-hydratable, i.e., anhydrous crystalline form of the vapendavir free base. The form was determined to have low hygroscopicity (DVS <0.1% wt gain), and since there was no hydrate formation observed under aqueous conditions, the new crystalline form of the free base vapendavir will be advantageous during formulation as an oral tablet, suspension, or similar form suitable for oral administration, a process which typically involves wet-granulation/for manufacturing robustness and safety of powder handling. As such, in the absence of hydrate formation, the new crystal form will not have a propensity to undergo water induced/form changes ("process induced changes") during manufacture/formulation which has been a problem with prior art tablet manufacturing, such as those associated with the previous bis-dihydrogen phosphate crystalline salt form of vapendavir. The new crystalline form of the present invention also possesses a needle-like crystal habit in contrast to the plate-like crystal habit of the prior bis-dihydrogen phosphate salt.

Further, there will be manufacturing advantages associated with the needle-like crystal habit in terms of flowability in that the crystal habit can influence the ease of compression of a powder and the flow properties of the drug in the solid state. The plate-like crystals of tolbutamide, for example, cause powder bridging in the hopper of the tablet machine and also capping problems during tableting. Neither of these problems occurs with tolbutamide in other crystal habits. In addition, particle shape also influences flow properties and particles of similar sizes but different shapes can have markedly different flow properties because of differences in interparticulate contact areas.

It is thus an important advantage of the new crystalline form of the present invention that it is far more suitable than the prior art for large-scale drug product manufacturing because it is a non-hydrate i.e. anhydrous, and therefore not expected to suffer from "process-induced transformations" or "water-induced phase changes". As indicated above, this is in contrast to prior experience with tablet manufacture via wet-granulation/spray drying process steps involving previous forms of active ingredients, such as the bis-dihydrogen phosphate salt of vapendavir as discussed above. In addition, the anhydrous free-base crystalline form of vapendavir in accordance with the present invention has shown chemical stability and has been shown to be the thermodynamically most stable form.

The pharmaceutical composition in accordance with the present invention can be used to treat viral infections, for example a picornavirus such as Human rhinovirus (HRV). In one of the preferred embodiments, the pharmaceutical composition of the present invention may be administered to a patient in need thereof in a form suitable for oral administration. Such a composition may be in the form of a solid tablet, but other forms, such as filled capsules or caplets, and still other forms such as suspensions for oral administration and other suitable forms are also contemplated. Such unit dosage forms will normally contain an effective amount of the crystalline active ingredient 6-{2-[1-(6-methyl-3-pyridazinyl)-4-piperidinyl]ethoxy}-3-ethoxy-1,2-benzoxazole commensurate with the intended daily dosage range to be employed as described further below. In addition, the compounds and compositions of the invention may also be used in treating, alleviating, preventing or reducing the symptoms or exacerbations of asthma or chronic obstructive pulmonary disease (COPD). Still further, the compounds and compositions of the invention may be used to treat hand, foot and mouth disease. In these methods, a therapeutically effective amount of the compound or compositions according to the invention is administered to a patient in need of said treatment.

An exemplary dose for administration of a crystalline 6-{2-[1-(6-methyl-3-pyridazinyl)-4-piperidinyl]ethoxy}-3-ethoxy-1,2-benzoxazole composition and a pharmaceutical composition in accordance with the present invention is that amount which will be effective in preventing or treating a condition afflicting a patient including a viral infection, such as, but not limited to, rhinovirus or hand, foot and mouth disease, or in treating, alleviating, preventing or reducing the symptoms or exacerbations of asthma or chronic obstructive pulmonary disease (COPD). As the skilled artisan would readily recognize, this amount will vary greatly depending on the nature of the infection and the condition of a patient.

An "effective amount" or "therapeutically effective amount" of crystalline 6-{2-[1-(6-methyl-3-pyridazinyl)-4-piperidinyl]ethoxy}-3-ethoxy-1,2-benzoxazole or pharmaceutical agent/composition containing 6-{2-[1-(6-methyl-3-pyridazinyl)-4-piperidinyl]ethoxy}-3-ethoxy-1,2-benzoxazole to be used in accordance with the invention is thus intended to mean any non-toxic but sufficient amount of the compound, composition or agent that produces the desired prophylactic or therapeutic effect. Thus, as one skilled in the art would readily understand, the exact amount of the composition or a particular agent that is required will vary from subject to subject, depending on the species of virus the subject is infected with, age, and general condition of the subject, the severity of the condition being treated, the particular carrier or adjuvant being used and its mode of administration, and the like. Similarly, the dosing regimen should also be adjusted to suit the individual to whom the composition is administered and will once again vary with age, weight, metabolism, etc. of the individual. Accordingly, the "effective amount" of any particular compound, composition or agent will vary based on the particular circumstances, and an appropriate effective amount may be determined in each case of application by one of ordinary skill in the art using only routine experimentation.

For example, formulations in accordance with the invention may contain 0.1 to 500 milligrams of active ingredient per dosage unit, and total dosage per day may be in the range of 100 to 1500 mg per day. In other embodiments, the crystalline 6-{2-[1-(6-methyl-3-pyridazinyl)-4-piperidinyl]ethoxy}-3-ethoxy-1,2-benzoxazole may be administered in a dosage amount of from 300 mg to 1200 mg per day, or from 600 to 1000 mg per day. In an exemplary dosage unit, a tablet can be obtained containing 6-{2-[1-(6-methyl-3-pyridazinyl)-4-piperidinyl]ethoxy}-3-ethoxy-1,2-benzoxazole in an amount of 200 to 400 mg, for example, 300 mg. In another exemplary dosage unit, the 6-{2-[1-(6-methyl-3-pyridazinyl)-4-piperidinyl]ethoxy}-3-ethoxy-1,2-benzoxazole may be included in the composition in an amount of from about 40-60 percent by weight of the total weight of the pharmaceutical composition. As indicated above, the actual dosage regimen will be one that administers an effective amount of the active compound to a patient in need as indicated above.

In accordance with the present invention, a method is also provided for treating a viral infection such as a picornavirus comprising administering a therapeutically effective amount of the crystalline free base form of 6-{2-[1-(6-methyl-3-pyridazinyl)-4-piperidinyl]ethoxy}-3-ethoxy-1,2-benzoxazole as described above to a patient in need of said treatment. As indicated above, this crystalline free base form of 6-{2-[1-(6-methyl-3-pyridazinyl)-4-piperidinyl]ethoxy}-3-ethoxy-1,2-benzoxazole has a needle-like crystal habit and has the XRPD pattern shown in FIGS. 1A, 1B, 2A, 2B and 3. The method can be administered to treat or prevent a picornavirus such as human rhinovirus (HRV). As indicated above, the compound may be administered in any one of a number of solid forms such as a tablet, and in exemplary embodiments may be administered in an amount of 300 to 1500 mg per day. In other exemplary treatment regimes, the 6-{2-[1-(6-methyl-3-pyridazinyl)-4-piperidinyl]ethoxy}-3-ethoxy-1,2-benzoxazole may be administered in amounts of 100 to 1500 mg per day, from 300 mg to 1200 mg per day, or from 600 mg to 1000 mg per day.

In another embodiment, the 6-{2-[1-(6-methyl-3-pyridazinyl)-4-piperidinyl]ethoxy}-3-ethoxy-1,2-benzoxazole may be administered in a pharmaceutical composition that comprises 6-{2-[1-(6-methyl-3-pyridazinyl)-4-piperidinyl]ethoxy}-3-ethoxy-1,2-benzoxazole and a suitable pharmaceutical carrier.

Still further, a method in accordance with the invention is provided for treating, alleviating, preventing or reducing the symptoms or exacerbations of asthma or chronic obstructive pulmonary disease (COPD), of which reduced lung function is typically symptomatic, comprising administering a therapeutically effective amount of the anhydrous crystalline free base form of 6-{2-[1-(6-methyl-3-pyridazinyl)-4-piperidinyl]ethoxy}-3-ethoxy-1,2-benzoxazole as described above to a patient in need of said treatment.

The compound of the present invention can also provide benefits, including improved asthma control, during presumed symptomatic rhinovirus infection which may be measured by, e.g., ACQ-5, reduction in the frequency of β-agonists use, reduced frequency of exacerbation, improved lung function (FEV$_1$), and a quality of life questionnaire completed by patients. Other improved therapeutic results include reduced patient hospitalizations, reduction in the severity and duration of cold symptoms and reduced complications such as otitis media, secondary infections and associated reduced use of antibiotics.

In summary, as a result of the present invention, one can achieve an effective therapeutic dose in a tablet with a smaller size than in previous forms of vapendavir. In addition, the invention is advantageous because the new crystal form will not have a propensity to undergo water induced/form changes ("process induced changes") during manufacture/formulation which has been a problem in the prior art, and the needle-like crystal habit offers advantages in terms of flowability in that the crystal habit can influence the ease of compression of a powder and the flow properties of the drug in the solid state.

It will be understood that various details of the presently disclosed subject matter can be changed without departing from the scope of the subject matter disclosed herein. Furthermore, the foregoing description, and the examples that follow, are for the purpose of illustration only, and not for the purpose of limitation.

EXAMPLES

The present invention will now be described with regard to specific examples, experimental data including figures and results which provide for a more in depth understanding of the present invention. The examples, experimental data and results are provided for exemplary purposes only and are not intended to limit the scope of the invention. Further, one of ordinary skill in the art will readily understand that additional methods of manufacturing, pharmaceutical formulation and treatment may be arrived at through routine experimentation and known/or conventional techniques.

Example 1: Process for Manufacture of Crystal Free Base Form of 6-{2-[1-(6-methyl-3-pyridazinyl)-4-piperidinyl]ethoxy}-3-ethoxy-1,2-benzoxazole An exemplary process of manufacturing the anhydrous crystalline free base form of vapendavir in accordance with the invention can be shown in the reaction overview below:

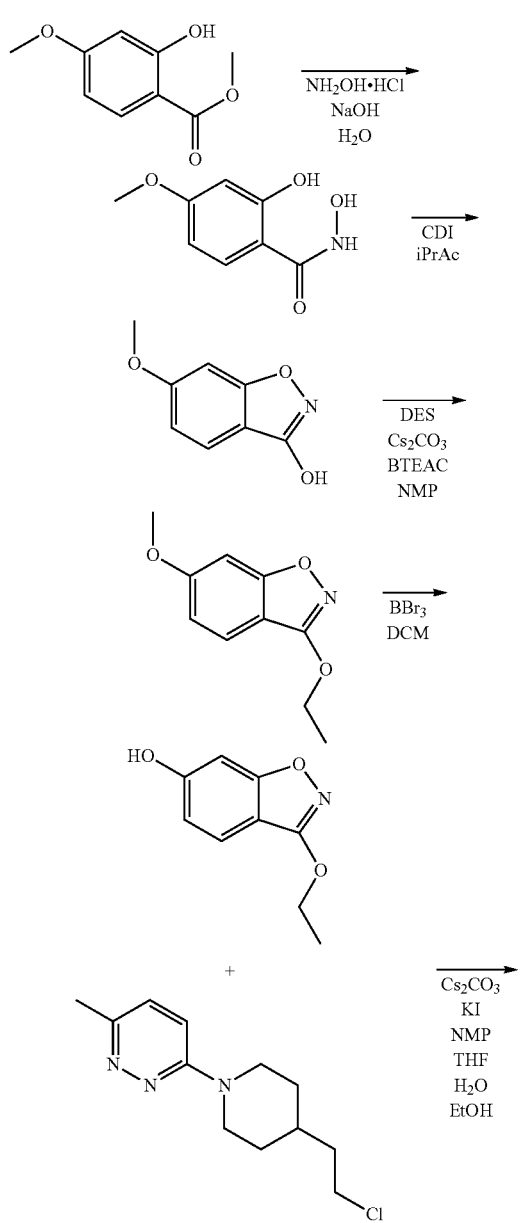

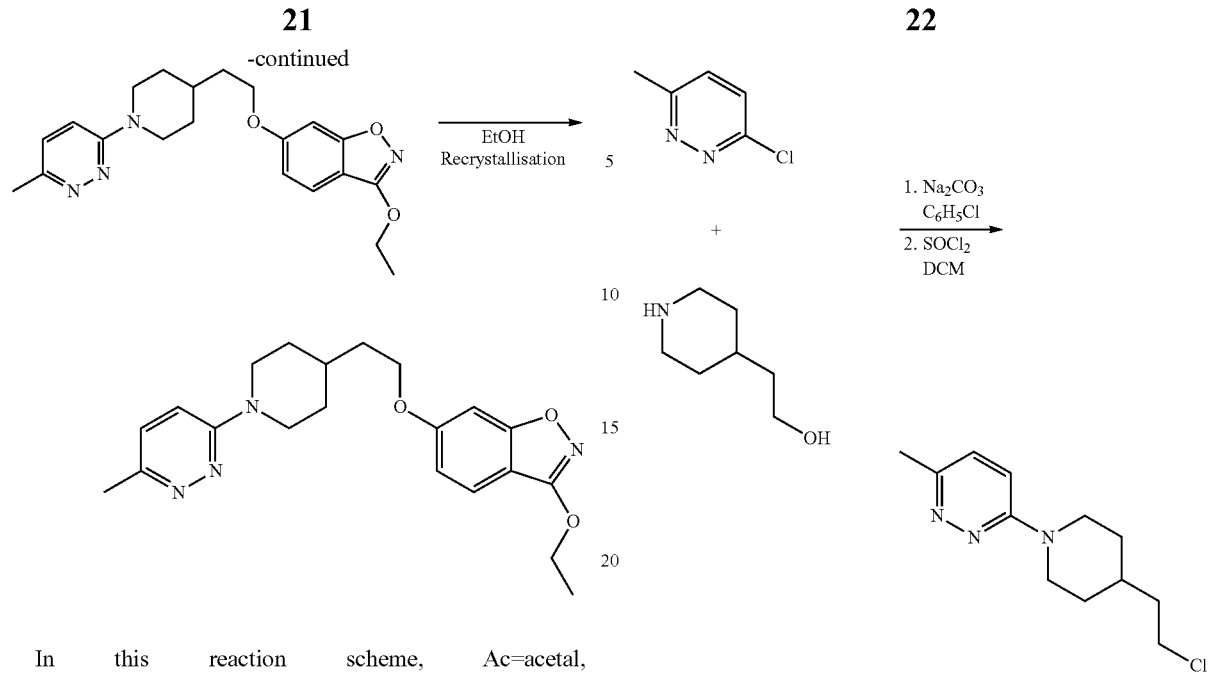

In this reaction scheme, Ac=acetal, BTEAC=benzyltriethylammonium chloride, CDI=1,1'-carbonyldiimidazole, DCM=dichloromethane, DES=diethylsulfate, Et=ethyl, iPr=isopropyl, NMP=N-methylpyrolidine and THF=tetrahydrofuran. In short, the production of vapendavir is obtained by reacting a compound having the formula (II):

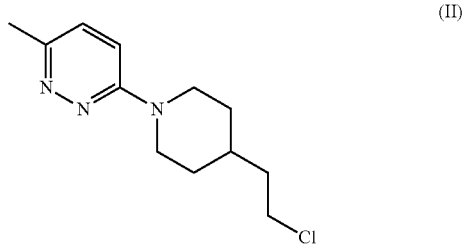 [SMILES: Cc1ccc(N2CCC(CCCl)CC2)nn1]

with a compound having the formula (III):

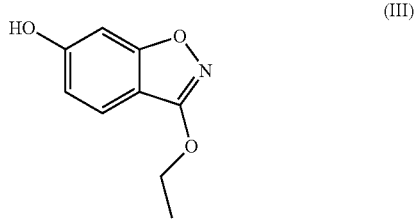

in a suitable reaction medium. The reaction medium may be a solution that may comprise cesium carbonate, potassium iodide, and N-methylpyrolidine. Tetrahydrofuran, ethanol and water may also be used for the work up of the freebase crystals obtained in the reaction. The reaction produces the free base form of 6-{2-[1-(6-methyl-3-pyridazinyl)-4-piperidinyl]ethoxy}-3-ethoxy-1,2-benzoxazole in accordance with the present invention. The compound identified as formula (II) above may be produced in the following reaction:

As further shown in the above exemplary reaction, a process for manufacturing the anhydrous crystalline free base form of the compound 6-{2-[1-(6-methyl-3-pyridazinyl)-4-piperidinyl]ethoxy}-3-ethoxy-1,2-benzoxazole in accordance with the present invention may also involve a step of recrystallization with a suitable solvent. In one example, the recrystallization of the anhydrous free base crystalline form of 6-{2-[1-(6-methyl-3-pyridazinyl)-4-piperidinyl]ethoxy}-3-ethoxy-1,2-benzoxazole of the invention is carried out using active charcoal treatment to remove impurities and a series of solvents to produce the recrystallized 6-{2-[1-(6-methyl-3-pyridazinyl)-4-piperidinyl]ethoxy}-3-ethoxy-1,2-benzoxazole anhydrous free base crystalline form.

Example 2: Alternative Process for Manufacture of Crystal Free Base Form of 6-{2-[1-(6-methyl-3-pyridazinyl)-4-piperidinyl]ethoxy}-3-ethoxy-1,2-benzoxazole Another exemplary process of manufacturing the anhydrous crystalline free base form of vapendavir in accordance with the invention is provided below.

In this example, 3-[4-(2-chloroethyl)-1-piperidyl]-6-methyl-pyridazine (14.6 kg) was charged portion wise as a solid to a stirred mixture of 3-ethoxy-6-hydroxy-1,2-benzoxazole (10.9 kg), caesium carbonate (29.7 kg) and potassium iodide (2.0 kg) in N-methylpyrrolidone (87 L) at 90° C. The mixture was stirred at 90° C. for at least ten hours. Upon confirmation of reaction completion (>95% conversion by HPLC), the mixture was cooled to 65° C. A mixture of water and THF (4/1 v/v, 240 L) was then added to the suspension whilst maintaining the temperature below 70° C. The mixture was stirred for at least 1 hour before cooling to 5° C. The cooled suspension was filtered, and the filter cake washed with a mixture of water and THF (4/1 v/v, 2×55 L) and washed with ethanol (2×27 L) before drying to afford vapendavir (19.4 kg, 83% yield).

A mixture of dichloromethane (100 L) and ethanol (73 L) were added to the vapendavir obtained above (18.2 kg) and charcoal (1.8 kg). The mixture was stirred at 20° C. for at least 10 hours before removal of the solids by filtration over a bed of filter aid and via an in-line filter. The filter cake was subsequently washed with a mixture of dichloromethane and ethanol (1/1 v/v, 2×18 L). The resulting filtrates were solvent swapped to ethanol by concentration under reduced pressure until the level of dichloromethane was below 1% w/w.

The resulting ethanol suspension of vapendavir was heated to reflux before cooling to 20° C. The resulting suspension was wet milled by recirculation through an in-line pump equipped with a wet milling pump head. The suspension was heated to 40° C. for at least 10 minutes before cooling to 20° C. followed by filtration. The resulting crystalline solid was washed with ethanol (2×28 L) and dried until the residual ethanol content was below 1000 ppm (16.6 kg, 91% yield).

Example 3: Solid State Characterization and Aqueous Solubility Determination of Crystalline Freebase Versus Phosphate Salt Forms of Vapendavir Tests were conducted in order to assess the solid state characterization and aqueous solubility determination of the crystalline free base vapendavir of the present invention (also identified as BTA-798) as well as prior art versions of vapendavir including the phosphate salt form of the drug substances. These tests also summarize comparative dissolution profiles of these drug substances formulated into drug products.

I. Samples Tested:
  A. BTA-798 freebase drug substance lot #NE-021602-BATCH-01-2013
  B. BTA-798 phosphate salt substance lot #DB330701.2
  C. 300 mg BTA-798 freebase tablet lot#C14011
  D. 200 mg BTA-798 phosphate salt capsules lot#PPP.14.098
  E. 300 mg BTA-798 freebase tablets lot#C14002B
  F. 132 mg BTA-798 freebase capsule lot#CU05-087 & CU05-093

II. Equipment:
  A. X-ray diffractometer: Rigaku Miniflex 600 with copper x-ray source
  B. Particle size analyzer: Malvern Mastersizer 3000
  C. Scanning Electron Microscope: JEOL JCM-6000 NeoScope Benchtop
  D. Dissolution Bath: Distek Dissolution System Evolution 6100
  E. Dissolution Auto Sampler: Distek Autosampler Evolution 4300

Figure 9:
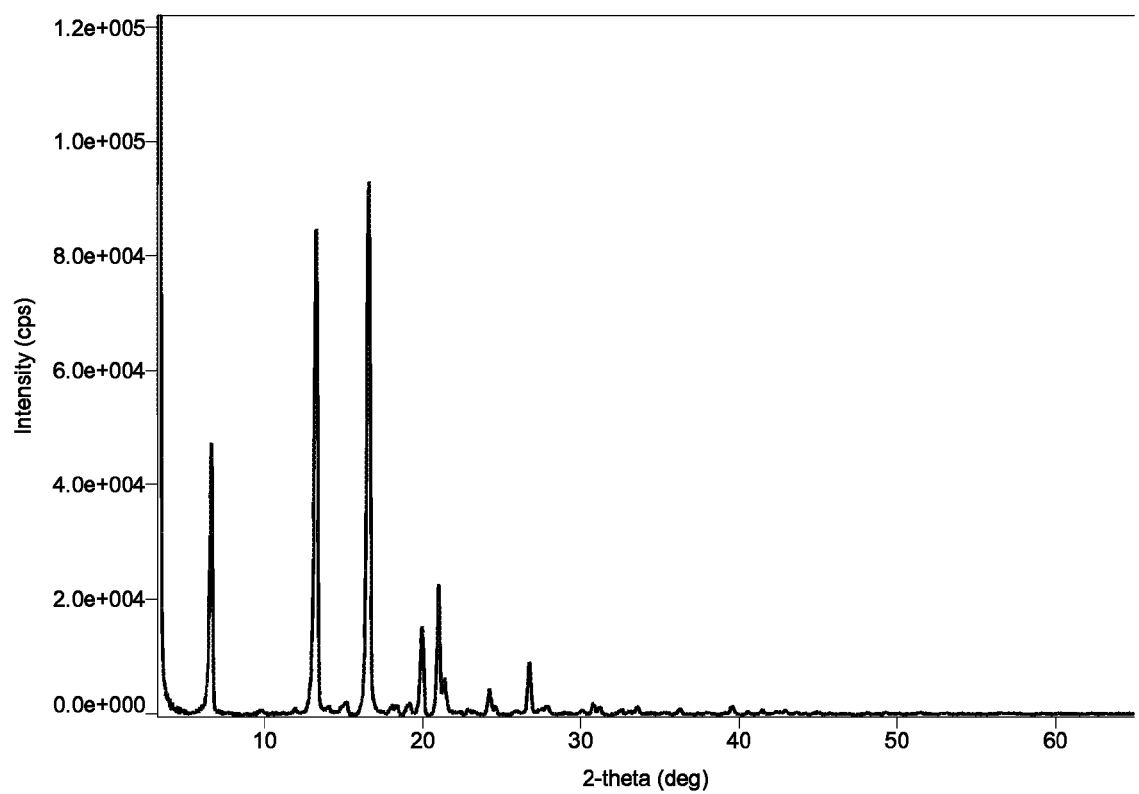
FIG. 9 shows the XRPD peak (2θ) profile for the prior phosphate salt form of 6-{2-[1-(6-methyl-3-pyridazinyl)-4-piperidinyl]ethoxy}-3-ethoxy-1,2-benzoxazole.
Figure 10:
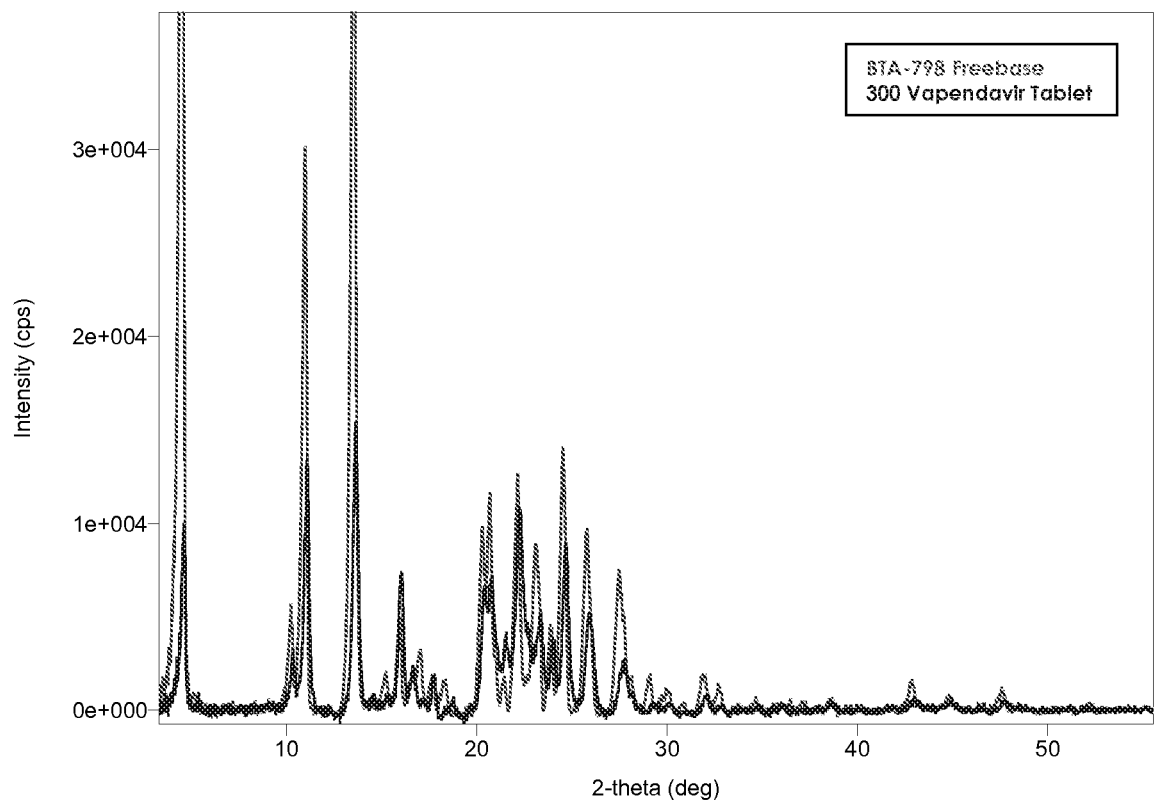
FIG. 10 is a graph of a comparison of the XRPD patterns of the micronized crystalline freebase vapendavir with a Vapendavir 300 mg tablet as set forth in more detail below.
Figure 11:
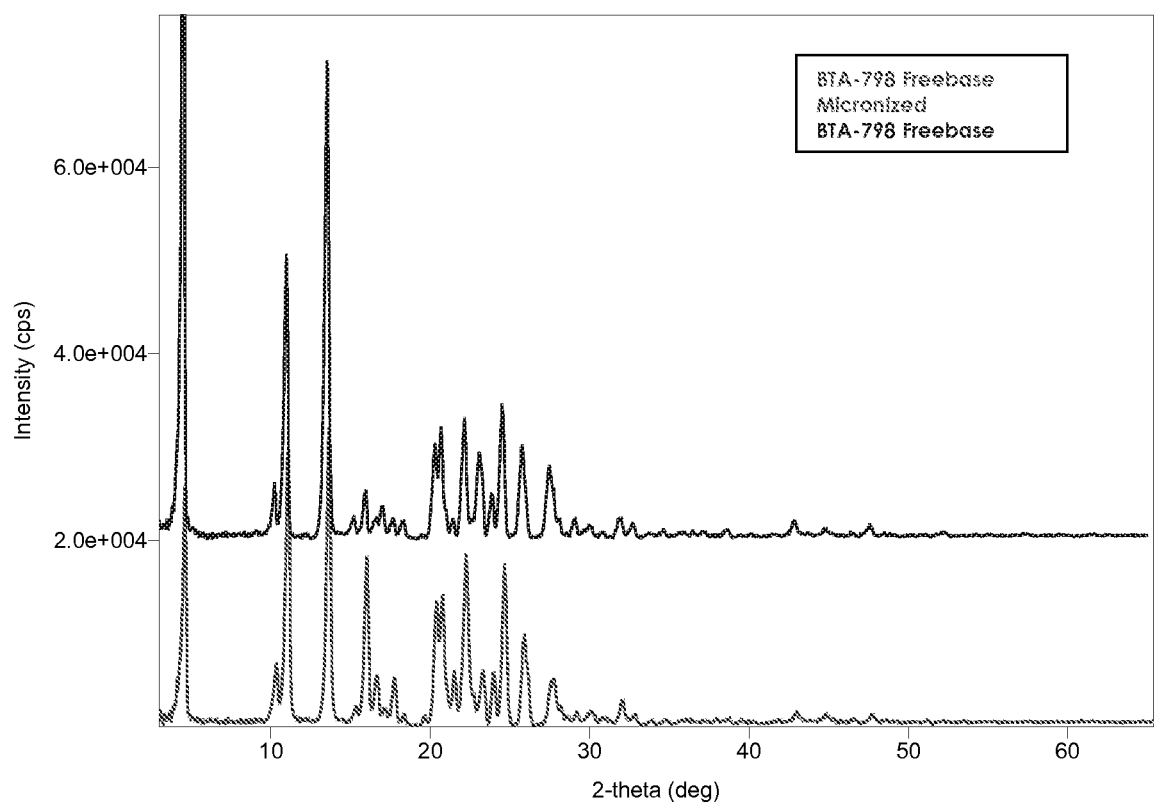
FIG. 11 is a graph of a comparison of the XRPD patterns of the micronized crystalline freebase vapendavir with a non-micronized crystalline freebase vapendavir as set forth in more detail below.

III. Procedure:
  A. Powder X-ray Diffraction
  1. BTA-798 freebase (FIGS. 1A and 1B) and BTA-798 phosphate salt (FIG. 9) were applied to separate sampler holders and analyzed as is.
  2. One tablet was ground in a mortar and pestle (Lot#C14011). The powder from the ground tablet was applied to sample holder and analyzed. The tablet was compared with BTA-798 freebase API (FIG. 10).
  3. BTA-798 freebase drug substance lot #NE-021602-BATCH-01-2013 was sent to Micron Technologies for Micronization. This micronized drug substance was compared with non-micronized BTA-798 freebase drug substance (FIG. 11).

4. Instrument Parameters:

| | | |
|---|---|---|
| a. | X-Ray | 40 kV, 15 mA |
| b. | Goniometer | MiniFlex 300/600 |
| c. | Attachment | Standard |
| d. | Filter | None |
| e. | CBO selection slit | — |
| f. | Diffracted beam mono. | None |
| g. | Detector | SC-70 |
| h. | Scan mode | Continuous |
| i. | Scan speed/Duration | 10.0000 deg/min |
| j. | Step width | 0.0200 deg |
| k. | Scan axis | Theta/2-Theta |
| l. | Scan range | 3.0000-65.0000 deg |
| m. | Incident slit | 1.250 deg |
| n. | Length limiting slit | 10.0 mm |
| o. | Receiving slit #1 | 1.250 deg |
| p. | Receiving slit #2 | 0.3 mm |

Figure 12:
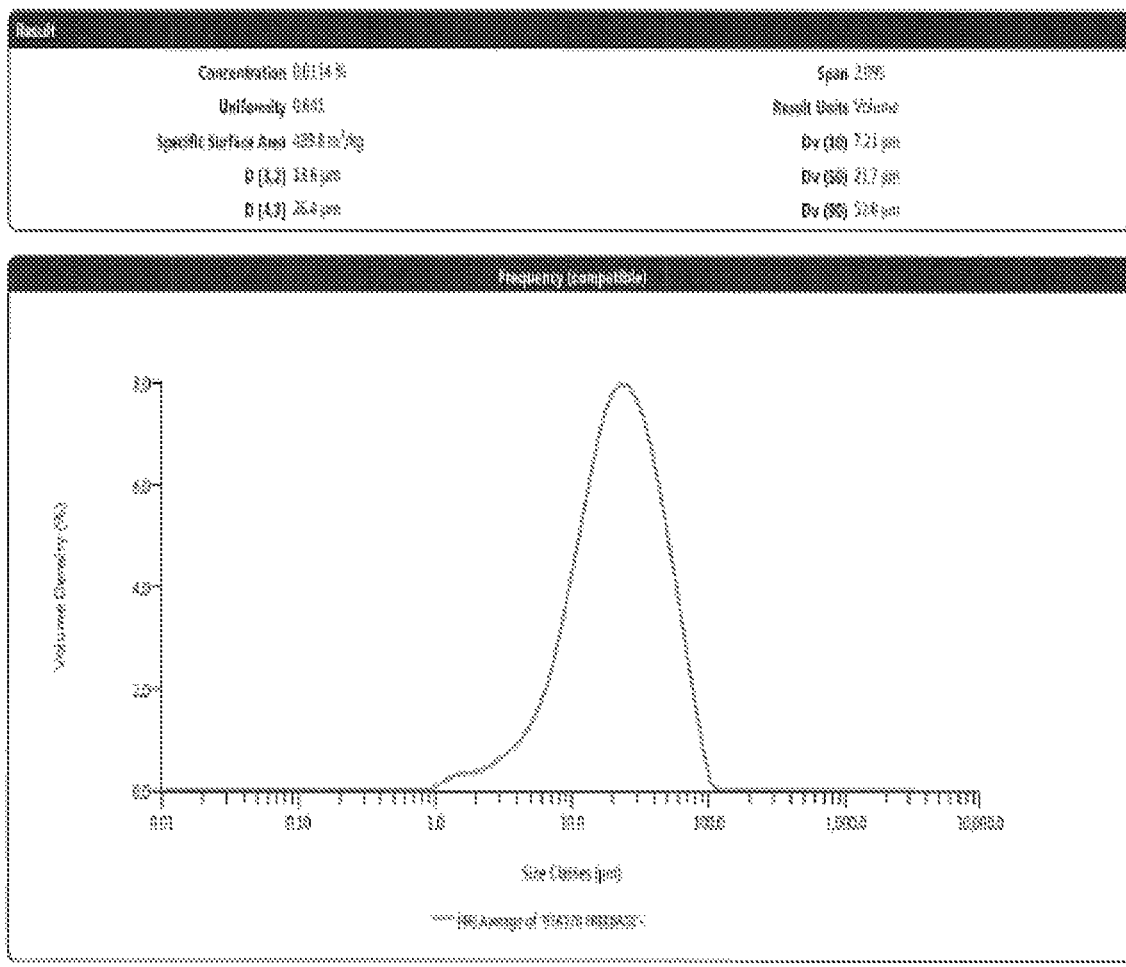
FIG. 12 is a graph of particle size analysis as described further herein.
Figure 13:
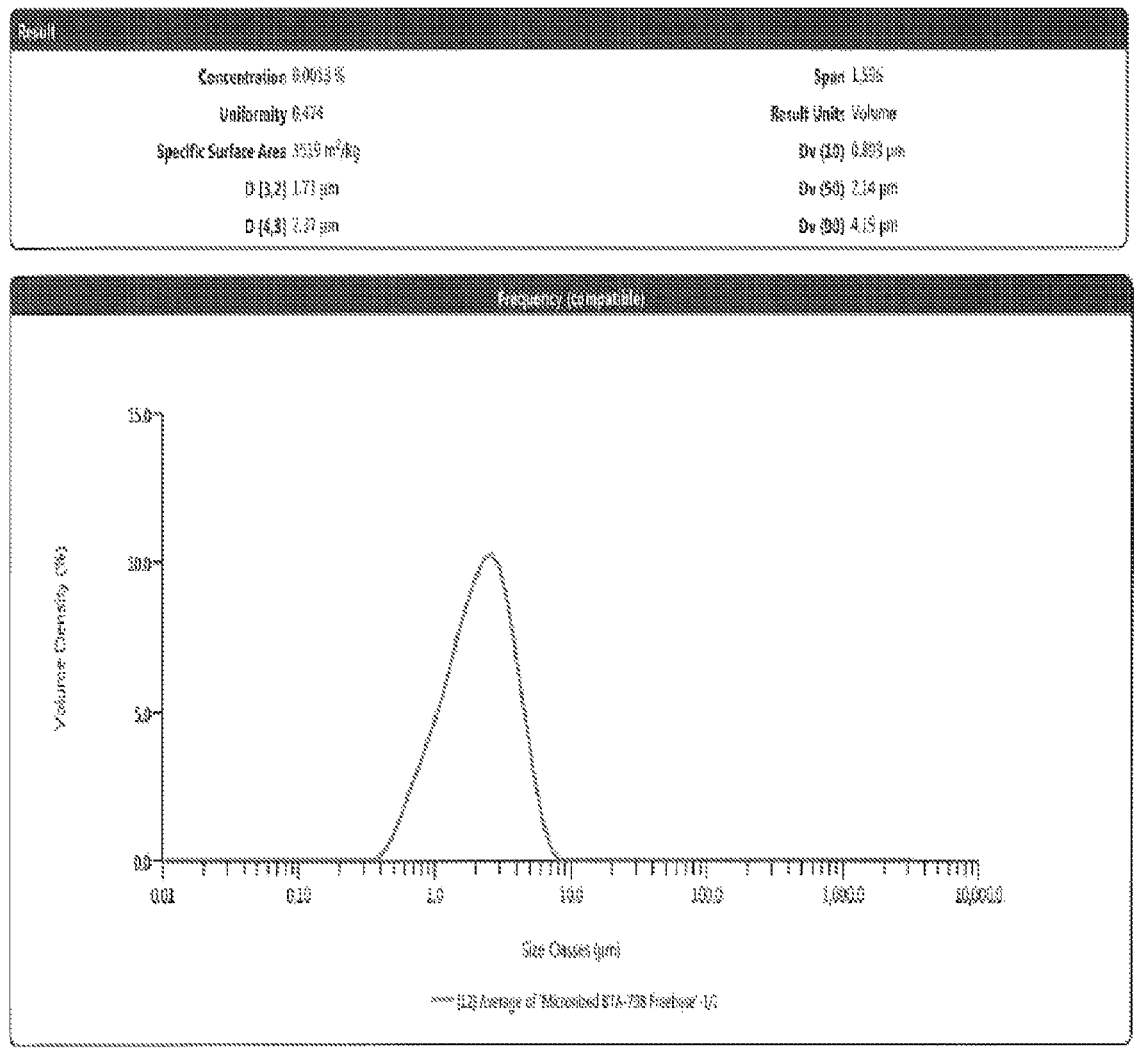
FIG. 13 is a graph of particle size analysis as described further herein.
Figure 14:
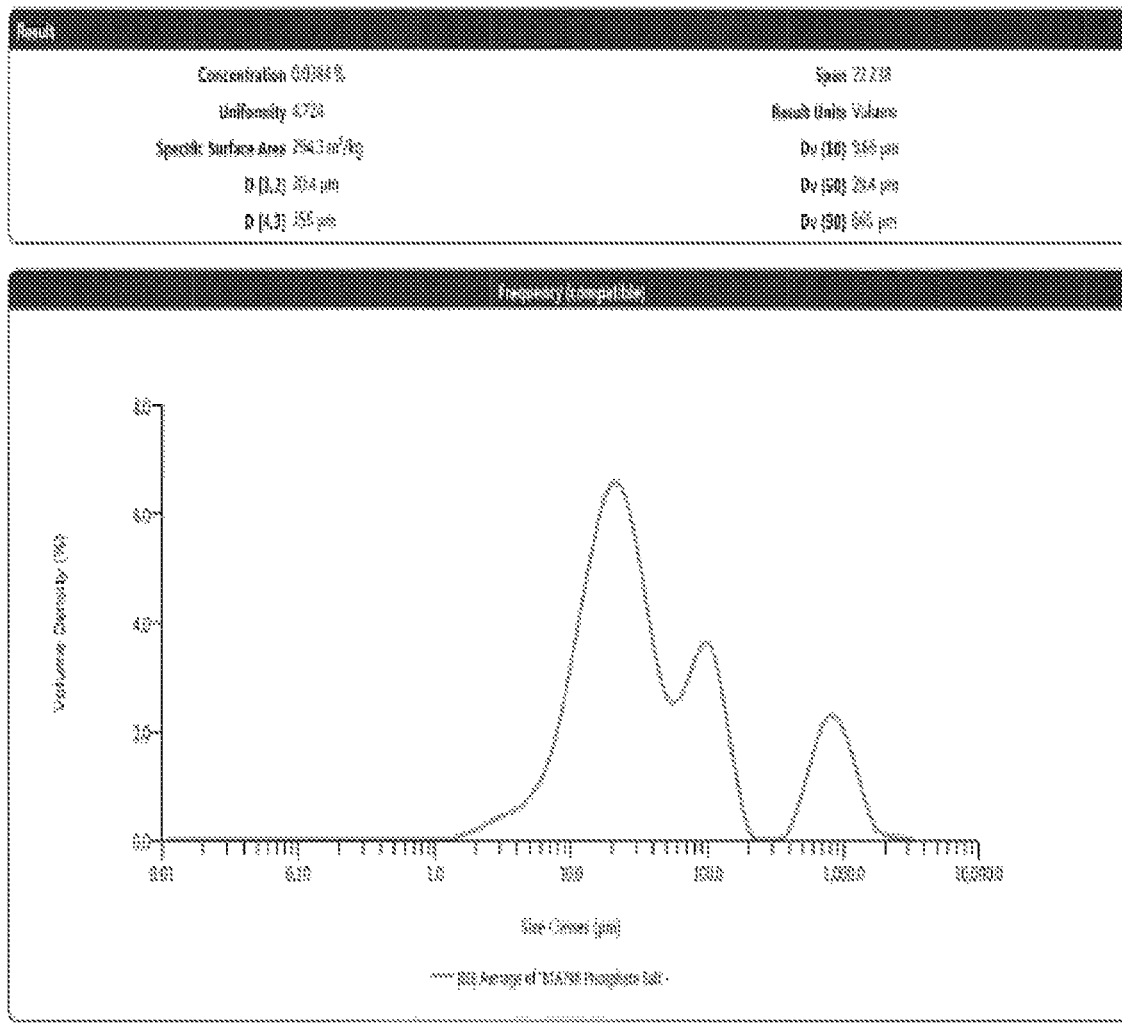
FIG. 14 is a graph of particle size analysis as described further herein.

B. Particle Size Analysis
1. The drug substances were dispersed in ~400 mL of water. Particle size analysis results are shown in FIGS. 12, 13, and 14 and Table 4.

TABLE 4

Drug Substance Particle Size Analysis Summary

| Sample | $D_{10}$ | $D_{50}$ | $D_{90}$ |
|---|---|---|---|
| BTA-798 freebase Lot# NE-021602-BATCH-01-2013 | 7.21 μm | 21.7 μm | 52.8 μm |
| BTA-798 freebase Lot# NE-021602-BATCH-01-2013 (micronized) | 0.893 μm | 2.14 μm | 4.19 μm |
| BTA-798 phosphate salt lot # DB330701.2 | 9.69 μm | 29.4 μm | 665 μm |

2. Instrument Parameters:

| | |
|---|---|
| a. Particle RI | 1.680 |
| b. Dispersant RI | 1.330 |
| c. Absorption Index | 0.010 |
| d. Scattering Model | Mie |

Figure 15:
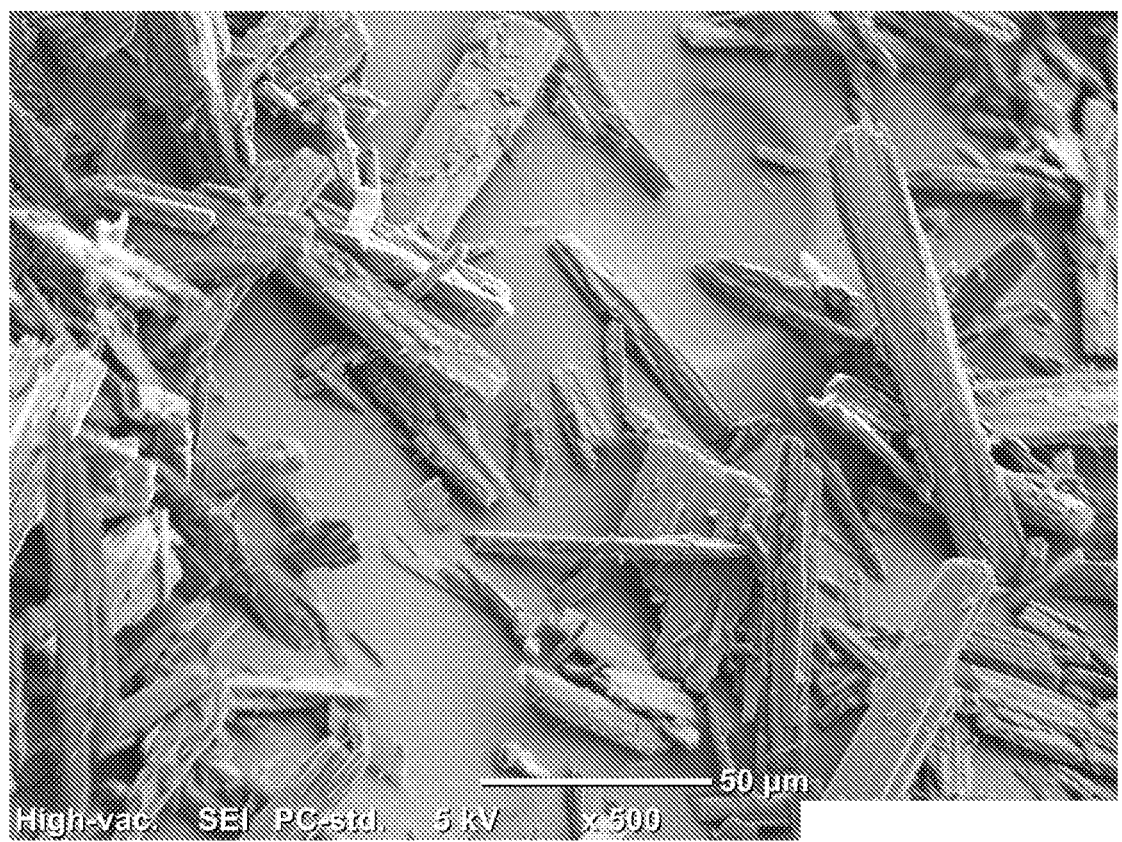
FIG. 15 is a micrograph showing particles from the compound of the invention with the needle-like crystal habit prior to micronization.
Figure 16:
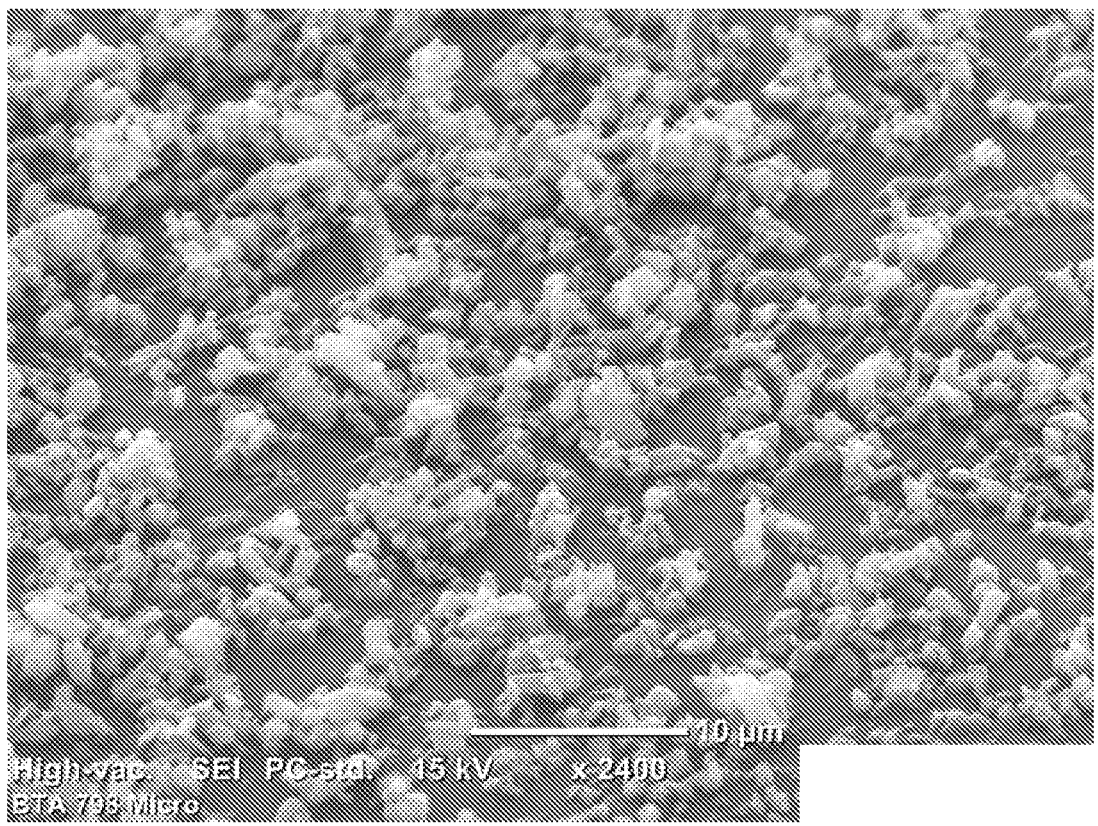
FIG. 16 is a micrograph showing particles from the compound of the invention after micronization.
Figure 17:
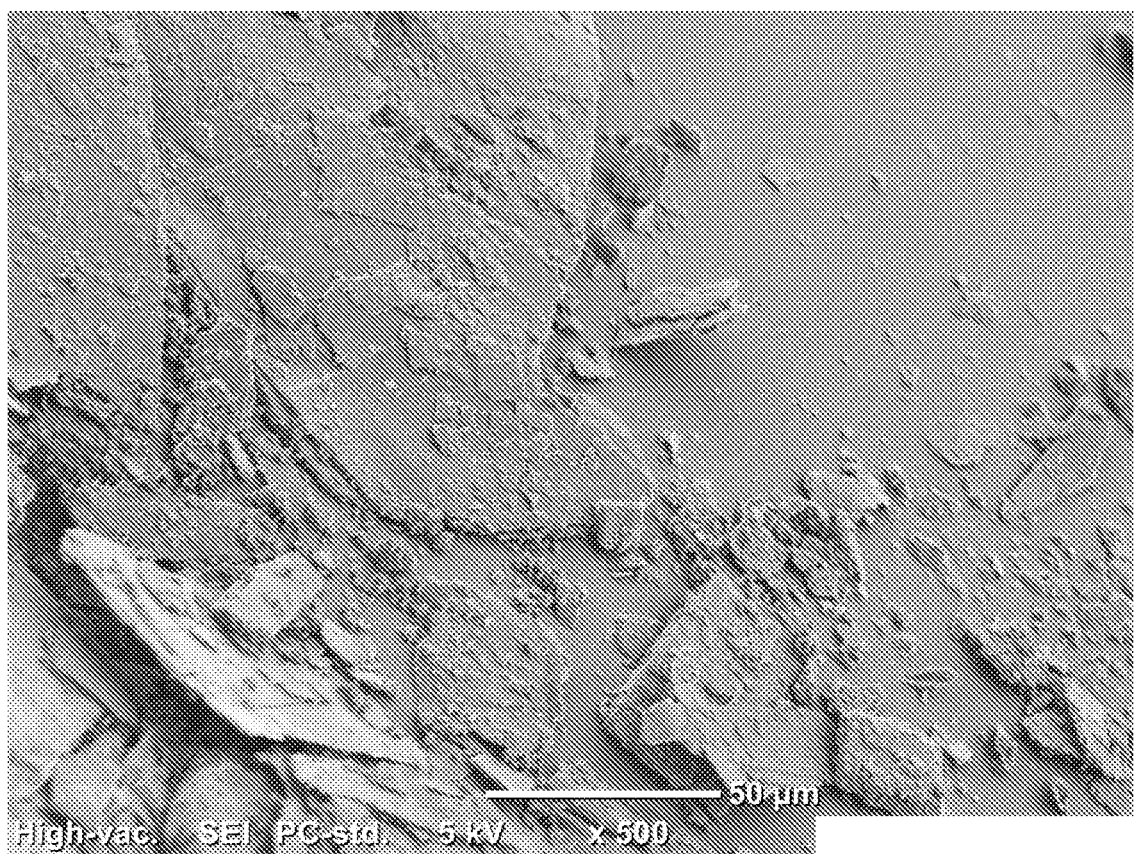
FIG. 17 is a micrograph showing particles from the prior phosphate salt of vapendavir having a plate-like crystal habit.
Figure 18A:
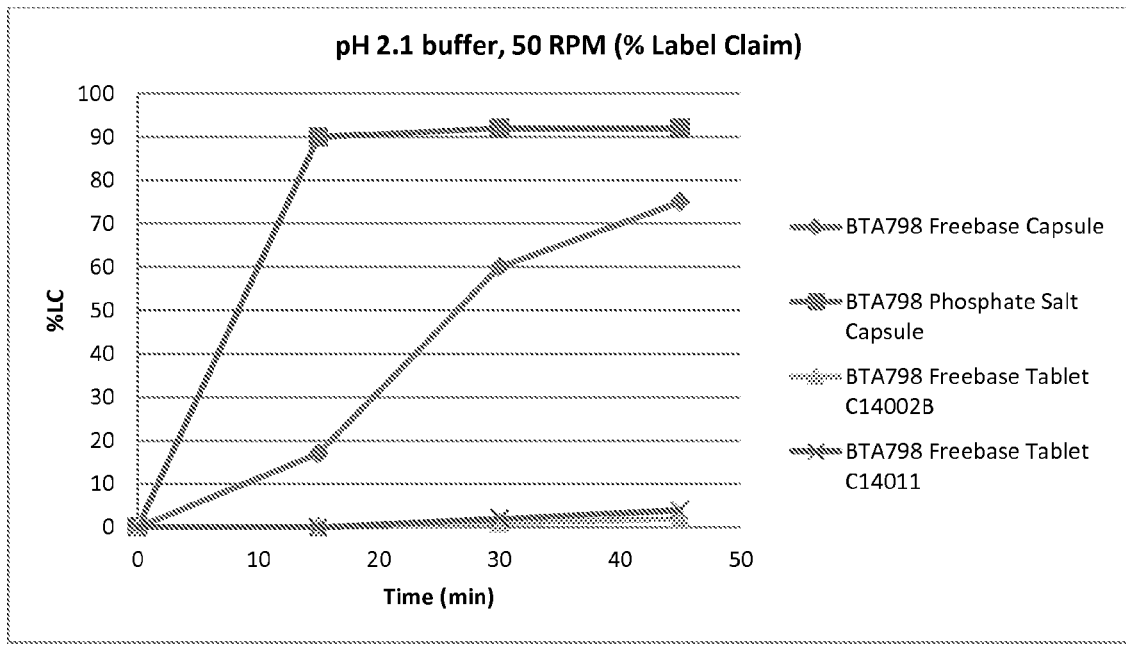
FIG. 18A is a graph showing dissolution rate as described further herein.
Figure 18B:
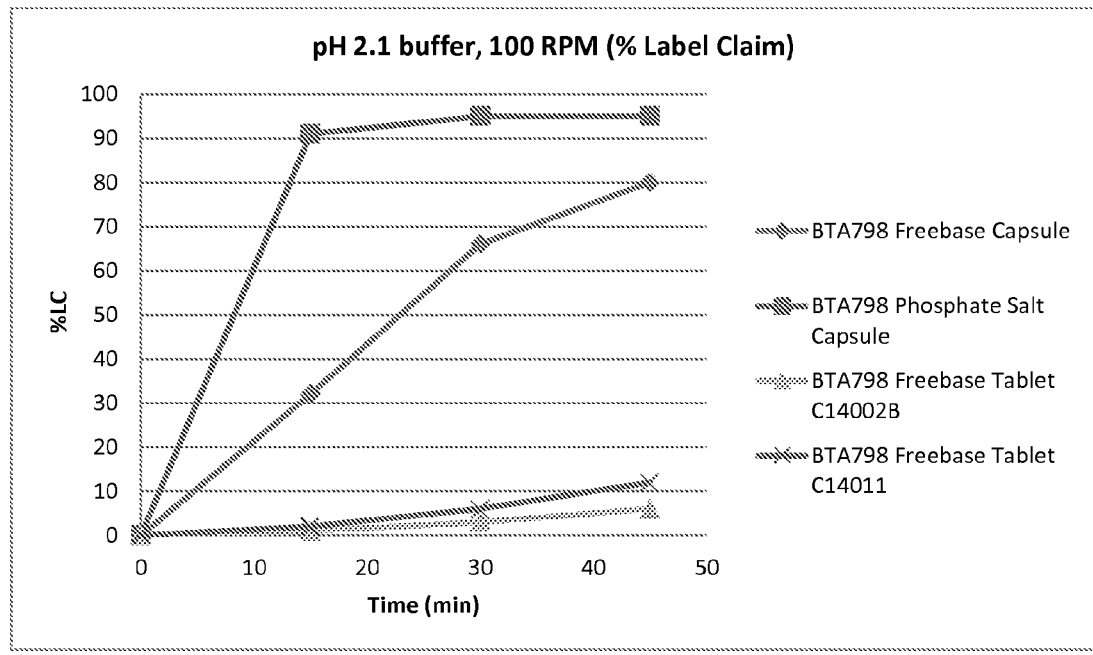
FIG. 18B is a graph showing dissolution rate as described further herein.
Figure 18C:
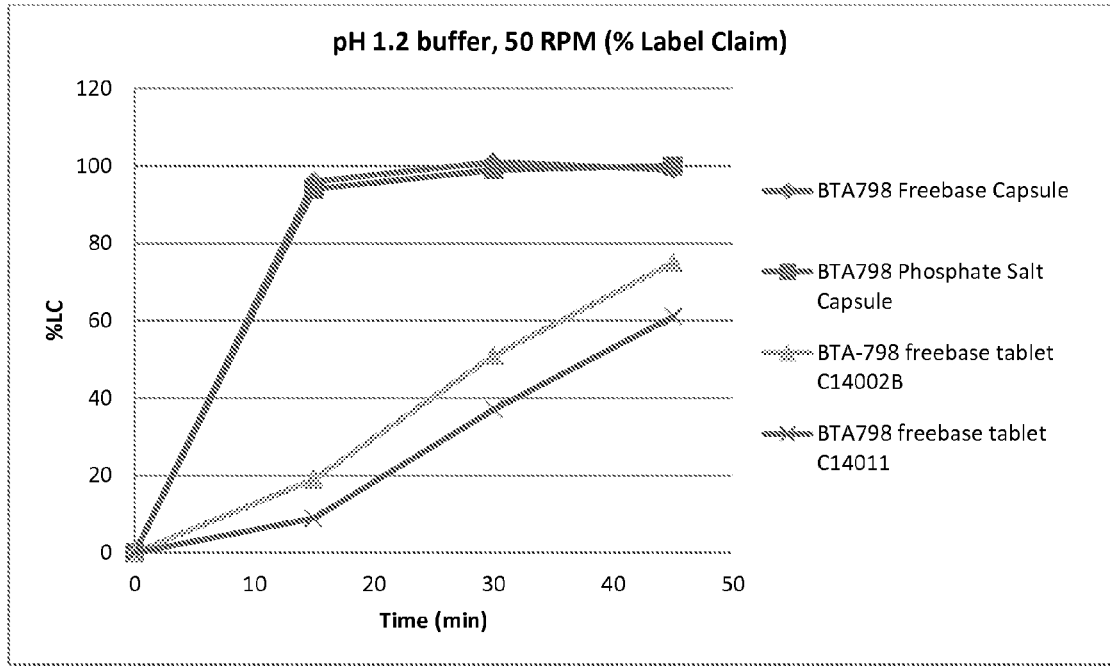
FIG. 18C is a graph showing dissolution rate as described further herein.
Figure 18D:
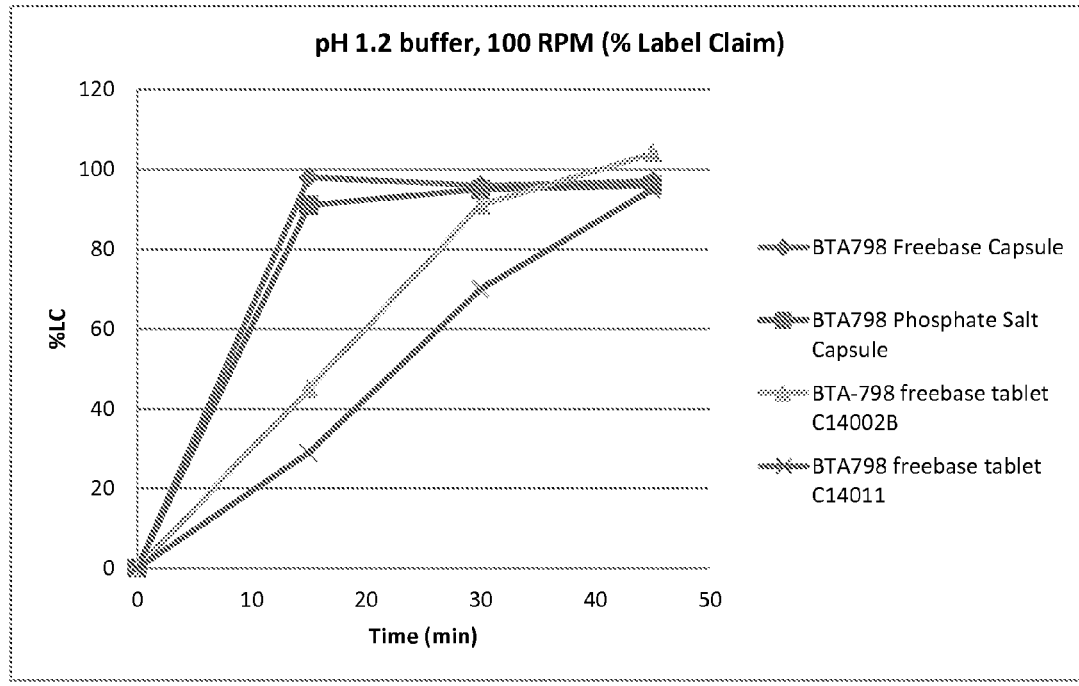
FIG. 18D is a graph showing dissolution rate as described further herein.

C. Scanning Electron Microscopy (SEM)
1. A small amount of BTA-798 freebase (FIGS. 15 and 16) and BTA-798 phosphate salt (FIG. 17) were applied to separate pin mounts.
2. The samples were sputter coated with gold until a thin coat was evenly applied.
3. Pin mounts were mounted at a 45 angle.

D. Solubility Study
1. Several 0.6 mg/mL of BTA-798 freebase solutions were prepared in various buffer systems (Table 5). Solutions were placed into a 37° C. water bath for approximately 24 hours.

TABLE 5

Buffer Systems

| Buffer | pH |
|---|---|
| 0.1M HCl | 1.2 |
| 0.1M Sodium Phosphate Monobasic | 2.1 |
| 0.1M Citric Acid | 3.0 |
| 0.1M Acetic Acid | 4.0 |
| 0.1M Citric Acid | 5.0 |
| 0.1M Potassium Phosphate Monobasic | 6.0 |

TABLE 5-continued

| Buffer Systems | |
| --- | --- |
| Buffer | pH |
| 0.1M Potassium Phosphate Monobasic | 7.0 |
| 0.1M Potassium Phosphate Monobasic | 8.0 |

2. A portion of each solution was filtered and assay by HPLC.

3. Instrument Parameters (HPLC):

| | |
| --- | --- |
| a. Column | X-Bridge C18 3.5 μm, 4.6 × 150 mm |
| b. Flow Rate | 1.0 mL/min |
| c. Column Rate | 35° C. |
| d. Injection Volume | 2.5 μL |
| e. Detection | 252 nm |
| f. Run Time | 32 minutes |
| g. Mobile Phase A | 10 mM Phosphate Buffer pH 3.0 |
| h. Mobile Phase B | Methanol |
| i. Diluent | 50% 0.1M HCl in Methanol |

| j. Gradient | Time (min) | % MPB |
| --- | --- | --- |
| | 0 | 40 |
| | 25 | 85 |
| | 27 | 85 |
| | 28 | 40 |
| | 32 | 40 |

4. This study was repeated for BTA-798 phosphate salt.

The results of the solubility studies are summarized in Table 6 below.

TABLE 6

| Drug Substance Solubility Summary | | |
| --- | --- | --- |
| pH | BTA-798 freebase (mg/mL) | BTA-798 phosphate salt (mg/mL) |
| Lot | NE-021602-BATCH-01-2013 | DB330701.2 |
| 1.2 | ≥0.6 | ≥0.6 |
| 2.1 | 0.37 | ≥0.6 |
| 3.0 | 0.11 | 0.20 |
| 4.0 | 0.01 | 0.02 |
| 5.0 | ND | 0.004 |
| 6.0 | ND | ND |
| 7.0 | ND | ND |
| 8.0 | ND | ND |

ND = Not Detected

E. Dissolution

1. To determine the dissolution rate of various tablets and capsules in pH 1.2 and 2.1 dissolution medium by HPLC.

2. Dissolution Parameters:

| | |
| --- | --- |
| a. Apparatus | USP 1, Baskets |
| b. Agitation Rate | 50 and 100 RPM |
| c. Vessel Temp | 37° C. ± 0.5° C. |
| d. Sample Times | 15, 30, and 45 min |
| e. Medium | 0.1M Phosphate Buffer pH 2.1 or 0.1 M HCl pH 1.2 |
| f. Medium Volume | 900 mL |
| g. Filter | 45 μm in-line |

3. Instrument Parameters (HPLC):

| | |
| --- | --- |
| a. Column | X-Bridge C18 3.5 μm, 4.6 × 150 mm |
| b. Flow Rate | 1.0 mL/min |
| c. Column Rate | 35° C. |
| d. Injection Volume | 5 μL |
| e. Detection | 252 nm |
| f. Run Time | 7 minutes |
| g. Mobile Phase A | 30% 10 mM Phosphate Buffer pH |
| h. Mobile Phase B | 70% Methanol |
| i. Diluent | 50% 0.1M HCl in Methanol |

The results of the dissolution studies are shown in FIGS. 18A-18D and are summarized in the following Tables 7-10 below.

TABLE 7

(See FIG. 18A)
Dissolution Rate in pH 2.1 buffer at 50 RPMs (% Label Claim)

| Sample | 0 min | 15 min | 30 min | 45 min |
| --- | --- | --- | --- | --- |
| BTA-798 freebase capsule CU05-087 | 0 | 17 | 60 | 75 |
| BTA-798 phosphate salt capsule PPP.14.098 | 0 | 90 | 92 | 92 |
| BTA-798 freebase tablet C14002B | 0 | 0 | 1 | 2 |
| BTA798 freebase tablet C14011 | 0 | 0 | 2 | 4 |

TABLE 8

(See FIG. 18B)
Dissolution Rate at pH 2.1 buffer at 100 RPMs (% Label Claim)

| Ave of 3 vessels | 0 min | 15 min | 30 min | 45 min |
| --- | --- | --- | --- | --- |
| BTA798 freebase capsule CU05-087 | 0 | 32 | 67 | 81 |
| BTA798 phosphate salt capsule PPP.14.098 | 0 | 91 | 95 | 95 |
| BTA798 freebase tablet C14002B | 0 | 1 | 3 | 6 |
| BTA798 freebase tablet C14011 | 0 | 2 | 6 | 12 |

TABLE 9

(See FIG. 18C)
Dissolution Rate in pH 1.2 buffer at 50 RPMs (% Label Claim)

| Ave of 3 vessels | 0 min | 15 min | 30 min | 45 min |
| --- | --- | --- | --- | --- |
| BTA-798 freebase capsule MJD01-35 | 0 | 96 | 101 | 99 |
| BTA-798 phosphate salt capsule PPP.14.098 | 0 | 94 | 99 | 100 |
| BTA-798 freebase tablet C14002B | 0 | 19 | 51 | 75 |
| BTA798 freebase tablet C14011 | 0 | 9 | 37 | 61 |

TABLE 10

(See FIG. 18D)
Dissolution Rate at pH 1.2 buffer at 100 RPMs (% Label Claim)

| Ave of 3 vessels | 0 min | 15 min | 30 min | 45 min |
| --- | --- | --- | --- | --- |
| BTA798 freebase capsule MJD01-35 | 0 | 98 | 96 | 97 |
| BTA-798 phosphate salt capsule PPP.14.098 | 0 | 91 | 95 | 96 |
| BTA-798 freebase tablet C14002B | 0 | 45 | 91 | 104 |
| BTA798 freebase tablet C14011 | 0 | 29 | 70 | 95 |

IV. Results and Conclusions:

The XRDP pattern of the freebase crystalline vapendavir of the present invention was shown to have the following peaks as observed in FIGS. 1A and 1B:

| No. | 2-theta (deg) |
|---|---|
| 1 | 4.531 |
| 2 | 10.259 |
| 3 | 10.995 |
| 4 | 13.560 |
| 5 | 15.18 |
| 6 | 15.942 |
| 7 | 16.59 |
| 8 | 17.002 |
| 9 | 17.70 |
| 10 | 18.33 |
| 11 | 20.265 |
| 12 | 20.624 |
| 13 | 21.43 |
| 14 | 22.124 |
| 15 | 23.139 |
| 16 | 23.857 |
| 17 | 24.531 |
| 18 | 25.741 |
| 19 | 27.420 |
| 20 | 29.08 |
| 21 | 30.082 |
| 22 | 31.86 |
| 23 | 32.68 |
| 24 | 34.61 |
| 25 | 35.64 |
| 26 | 37.18 |
| 27 | 42.83 |
| 28 | 43.72 |
| 29 | 44.71 |
| 30 | 47.61 |

A more detailed analysis of the XRDP pattern of the present freebase crystalline vapendavir showed the following pattern details:

| No. | 2-theta (deg) | d (ang.) | Rel. height (a.u.) |
|---|---|---|---|
| 1 | 4.531 ± 0.003 | 19.487 ± 0.014 | 100.00 |
| 2 | 10.259 ± 0.009 | 8.616 ± 0.008 | 4.48 |
| 3 | 10.995 ± 0.003 | 8.040 ± 0.002 | 30.24 |
| 4 | 13.560 ± 0.004 | 6.5247 ± 0.018 | 48.49 |
| 5 | 15.18 ± 0.02 | 5.831 ± 0.008 | 1.70 |
| 6 | 15.942 ± 0.011 | 5.555 ± 0.004 | 4.74 |
| 7 | 16.59 ± 0.03 | 5.340 ± 0.009 | 1.54 |
| 8 | 17.002 ± 0.018 | 5.211 ± 0.005 | 3.18 |
| 9 | 17.70 ± 0.02 | 5.007 ± 0.006 | 1.80 |
| 10 | 18.33 ± 0.02 | 4.835 ± 0.006 | 1.58 |
| 11 | 20.265 ± 0.017 | 4.379 ± 0.004 | 9.20 |
| 12 | 20.624 ± 0.013 | 4.303 ± 0.003 | 8.52 |
| 13 | 21.43 ± 0.04 | 4.143 ± 0.007 | 1.69 |
| 14 | 22.124 ± 0.009 | 4.0146 ± 0.016 | 12.21 |
| 15 | 23.139 ± 0.012 | 3.8408 ± 0.019 | 8.84 |
| 16 | 23.857 ± 0.017 | 3.727 ± 0.003 | 4.72 |
| 17 | 24.531 ± 0.008 | 3.6259 ± 0.012 | 14.14 |
| 18 | 25.741 ± 0.009 | 3.4581 ± 0.012 | 9.56 |
| 19 | 27.420 ± 0.014 | 3.2501 ± 0.016 | 6.82 |
| 20 | 29.08 ± 0.03 | 3.069 ± 0.003 | 1.81 |
| 21 | 30.082 ± 0.017 | 2.9683 ± 0.016 | 0.89 |
| 22 | 31.86 ± 0.02 | 2.806 ± 0.002 | 1.98 |
| 23 | 32.68 ± 0.03 | 2.738 ± 0.003 | 1.21 |
| 24 | 34.61 ± 0.07 | 2.589 ± 0.005 | 0.57 |
| 25 | 35.64 ± 0.05 | 2.517 ± 0.004 | 0.25 |
| 26 | 37.18 ± 0.03 | 2.4162 ± 0.016 | 0.44 |
| 27 | 42.83 ± 0.02 | 2.1096 ± 0.011 | 1.54 |
| 28 | 43.72 ± 0.04 | 2.0687 ± 0.016 | 0.23 |
| 29 | 44.71 ± 0.05 | 2.025 ± 0.002 | 0.62 |
| 30 | 47.61 ± 0.04 | 1.9083 ± 0.014 | 1.05 |

It was observed that the XRDP pattern of the freebase crystalline vapendavir of the present invention was shown to be different from the prior version of vapendavir in the form of a dihydrogen phosphate salt. The phosphate salt has the form as observed in FIG. 9 and had the following peaks:

| No. | 2-theta (deg) |
|---|---|
| 1 | 3.350 |
| 2 | 6.656 |
| 3 | 13.285 |
| 4 | 14.07 |
| 5 | 15.14 |
| 6 | 16.626 |
| 7 | 17.99 |
| 8 | 18.368 |
| 9 | 19.16 |
| 10 | 19.968 |
| 11 | 21.029 |
| 12 | 21.371 |
| 13 | 22.83 |
| 14 | 24.219 |
| 15 | 24.60 |
| 16 | 25.81 |
| 17 | 26.738 |
| 18 | 27.818 |
| 19 | 30.08 |
| 20 | 30.781 |
| 21 | 31.220 |
| 22 | 32.575 |
| 23 | 33.01 |
| 24 | 33.60 |
| 25 | 36.24 |
| 26 | 38.02 |
| 27 | 39.540 |
| 28 | 41.47 |
| 29 | 42.36 |
| 30 | 42.92 |

Accordingly, with regard to Powder X-ray Diffraction, the freebase crystal of the present invention was found to have distinctly different crystal structures than the previous phosphate salt form of vapendavir.

In comparative testing to assess the maintenance of the crystallography, a 300 mg Vapendavir was compared with the BTA-798 freebase, and the diffraction pattern of the tablet and API suggest the crystallography did not change during the manufacturing of the tablet. In addition, a micronized BTA-798 crystalline freebase vapendavir was compared with non-micronized BTA-798 freebase. The diffraction patterns of the micronized and non-micronized suggest the crystallography did not change during micronization.

With regard to particle size, the BTA-798 freebase crystal of the present invention had a much more uniform particle size distribution than the previous bis-phosphate form. The crystalline freebase vapendavir had a unimodal particle size distribution with a $D_{50}$ of 21.7 µm and a $D_{90}$ of 52.8 µm and the micronized BTA-798 freebase had a unimodal particle size distribution with a $D_{50}$ of 2.14 µm and a $D_{90}$ of 4.19 µm. On the other hand, the BTA-798 phosphate salt has a trimodal particle size distribution with a $D_{50}$ of 29.4 µm and a $D_{90}$ of 665 µm.

With regard to the microscopic patterns, the SEM micrographs included herein show that the BTA-798 freebase has a needle-like crystal structure that ranges in size from approximately 25 µm to 100 µm before micronization. After micronization, the micronized BTA-798 freebase drug substance has a crystal structure that ranges in size from approximately 2 µm to 5 µm. Once again, in sharp contrast to the crystalline freebase vapendavir of the present invention, the previous phosphate salt form of vapendavir has a plate-like crystal structure with a multi-modal particle size distribution having a much greater range than the crystalline freebase form of the invention. The testing showed that the phosphate salt form of vapendavir had particle sizes that range from approximately 2 μm to 150 μm.

With regard to solubility, while the solubility of the BTA-798 phosphate salt appeared to be greater than the solubility of the BTA-798 freebase at pH 5.0 and below, the solubility for the freebase at pH 5.0 and both drug substances at pH 6.0 to 8.0 are below the limit of detection of the HPLC assay method. The LOD of the HPLC method is 0.00006 mg/mL.

With regard to dissolution, the dissolution rate of four finished products were tested at pH 2.1 at two different basket speeds (50,100 RPM).
 a. 200 mg BTA-798 phosphate salt capsules
  i. At 15 minutes the drug is close to or completely released at both basket speeds.
 b. 132 mg BTA-798 freebase capsule
  i. After 45 minutes the drug has not fully released (33 to 35% LC). The profiles are similar at both basket speeds.
 c. 300 mg BTA-798 freebase tablet
  i. Two lots of tablets were tested. Both lots where less than % released after 45 minutes at both basket speeds. Since the freebase capsule exhibited significantly greater release than the freebase tablets after 45 minutes, it can be concluded that drug product formulation has a significant effect on the drug release profiles.

This dissolution experiment with repeated with dissolution media at pH 1.2, which was previously used for quality control testing.
 d. 200 mg BTA-798 phosphate salt capsules
  i. At 15 minutes the drug is close to or completely released at both basket speeds.
 e. 132 mg BTA-798 freebase capsule
  i. At 15 minutes the drug is close to or completely released at both basket speeds.
 f. 300 mg BTA-798 freebase tablet
  i. Two lot numbers of tablets were tested.

The dissolution profiles of both lots were similar at each basket speeds. At the 100 RPM basket speed, both tablets lagged behind the capsule formulations, but release completely after 45 minutes. At the 50 RPM basket speed, the tablet formulations did not fully release after 45 minutes. The pH 1.2 dissolution media did not differentiate between the freebase capsule and the phosphate salt capsule.

Example 4A: XRPD Analysis of Anhydrous Crystal Free Base Form of 6-{2-[1-(6-methyl-3-pyridazinyl)-4-piperidinyl]ethoxy}-3-ethoxy-1,2-benzoxazole As previously noted, the present crystalline form of 6-{2-[1-(6-methyl-3-pyridazinyl)-4-piperidinyl]ethoxy}-3-ethoxy-1,2-benzoxazole is composed of crystals which have a needle-habit. The present crystalline form is distinguishable from prior forms of 6-{2-[1-(6-methyl-3-pyridazinyl)-4-piperidinyl]ethoxy}-3-ethoxy-1,2-benzoxazole such as the bis-dihydrogen phosphate salt form of vapendavir which has a plate-like crystal habit. Further, the present crystalline 6-{2-[1-(6-methyl-3-pyridazinyl)-4-piperidinyl]ethoxy}-3-ethoxy-1,2-benzoxazole is an anhydrous compound which makes it extremely beneficial for use in a pharmaceutical composition since the anhydrous compound is stable (e.g. it is resistant to absorbing water) and does not change form upon wetting and milling. As a result, the present crystal 6-{2-[1-(6-methyl-3-pyridazinyl)-4-piperidinyl]ethoxy}-3-ethoxy-1,2-benzoxazole form is an extremely beneficial and advantageous form of 6-{2-[1-(6-methyl-3-pyridazinyl)-4-piperidinyl]ethoxy}-3-ethoxy-1,2-benzoxazole for incorporation into a pharmaceutical composition.

In addition to the tests described above, the anhydrous crystalline 6-{2-[1-(6-methyl-3-pyridazinyl)-4-piperidinyl]ethoxy}-3-ethoxy-1,2-benzoxazole was also analyzed using X-ray crystal powder diffraction, using the following equipment and method:

Equipment: Miniflx by Rigaku Corporation using silicon low background sample holders (diameter 24 mm, pit 0.2 mm). The Tube was Cu, λ=1.54056 Å, 15 kV Method: Angle 2θ=2° to 2θ=40° and sampling width 0.02 [2θ]

As a result of these tests, the anhydrous crystalline 6-{2-[1-(6-methyl-3-pyridazinyl)-4-piperidinyl]ethoxy}-3-ethoxy-1,2-benzoxazole of the invention was shown to have an XRPD peaks (2θ) profile shown in FIGS. 2A and 2B.

Major XRPD peaks (d-space, Å) shown below are selected from the group consisting of approximately the following values: 19.2, 8.5, 8.0, 6.5, 5.5, 5.3, 5.0, 4.35, 4.27, 4.12, 4.03, 3.99, 3.96, 3.80 and 3.60. The 2θ XRPD peaks may be selected from the group consisting of approximately the following values: 4.6, 10.4, 11.1, 13.7, 16.1, 16.7, 17.8, 20.4, 20.8, 21.6, 22.1, 22.3, 22.4, 23.4, and 24.8.

| °2θ | d space (Å) | Intensity (%) |
| --- | --- | --- |
| 4.60 ± 0.20 | 19.221 ± 0.874 | 13 |
| 10.36 ± 0.20 | 8.537 ± 0.168 | 18 |
| 11.11 ± 0.20 | 7.961 ± 0.145 | 65 |
| 13.69 ± 0.20 | 6.469 ± 0.095 | 41 |
| 16.08 ± 0.20 | 5.513 ± 0.069 | 100 |
| 16.73 ± 0.20 | 5.299 ± 0.064 | 17 |
| 17.82 ± 0.20 | 4.979 ± 0.056 | 14 |
| 20.42 ± 0.20 | 4.349 ± 0.043 | 36 |
| 20.82 ± 0.20 | 4.266 ± 0.041 | 35 |
| 21.59 ± 0.20 | 4.116 ± 0.038 | 21 |
| 22.08 ± 0.20 | 4.026 ± 0.036 | 13 |
| 22.31 ± 0.20 | 3.985 ± 0.036 | 22 |
| 22.44 ± 0.20 | 3.961 ± 0.035 | 26 |
| 23.40 ± 0.20 | 3.802 ± 0.032 | 12 |
| 24.77 ± 0.20 | 3.595 ± 0.029 | 25 |

Example 4B: XRPD Analysis of Anhydrous Crystal Free Base Form of 6-{2-[1-(6-methyl-3-pyridazinyl)-4-piperidinyl]ethoxy}-3-ethoxy-1,2-benzoxazole The anhydrous crystalline 6-{2-[1-(6-methyl-3-pyridazinyl)-4-piperidinyl]ethoxy}-3-ethoxy-1,2-benzoxazole was again analyzed using X-ray powder diffraction (XRPD), and the resulting observed peaks are shown in FIG. 3. The tables below provide a list of observed peaks and a list of prominent peaks. Peaks within the range of up to about 30° 2θ were selected, and rounding algorithms were used to round each peak to the nearest 0.01° 2θ.

The XRPD patterns were collected using a PANalytical X'Pert PRO MPD diffractometer using an incident beam of Cu radiation produced using an Optix long fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3 μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitize detector (X'Celerator) located 240 mm from the specimen and Data Collector software v. 2.2b.

TABLE 1

Observed peaks for BTA798 Form A, Lot NE-021602-E-5-33 crude 2-1, XRPD file 627932

| °2θ | d space (Å) | Intensity (%) |
|---|---|---|
| 4.60 ± 0.20 | 19.221 ± 0.874 | 13 |
| 10.36 ± 0.20 | 8.537 ± 0.168 | 18 |
| 11.11 ± 0.20 | 7.961 ± 0.145 | 65 |
| 13.69 ± 0.20 | 6.469 ± 0.095 | 41 |
| 15.39 ± 0.20 | 5.757 ± 0.075 | 6 |
| 16.08 ± 0.20 | 5.513 ± 0.069 | 100 |
| 16.56 ± 0.20 | 5.353 ± 0.065 | 6 |
| 16.73 ± 0.20 | 5.299 ± 0.064 | 17 |
| 17.18 ± 0.20 | 5.161 ± 0.060 | 2 |
| 17.36 ± 0.20 | 5.107 ± 0.059 | 3 |
| 17.82 ± 0.20 | 4.979 ± 0.056 | 14 |
| 18.42 ± 0.20 | 4.817 ± 0.052 | 3 |
| 19.14 ± 0.20 | 4.638 ± 0.049 | 1 |
| 19.69 ± 0.20 | 4.509 ± 0.046 | 3 |
| 20.42 ± 0.20 | 4.349 ± 0.043 | 36 |
| 20.82 ± 0.20 | 4.266 ± 0.041 | 35 |
| 21.14 ± 0.20 | 4.202 ± 0.040 | 5 |
| 21.59 ± 0.20 | 4.116 ± 0.038 | 21 |
| 22.08 ± 0.20 | 4.026 ± 0.036 | 13 |
| 22.31 ± 0.20 | 3.985 ± 0.036 | 22 |
| 22.44 ± 0.20 | 3.961 ± 0.035 | 26 |
| 22.76 ± 0.20 | 3.907 ± 0.034 | 5 |
| 23.05 ± 0.20 | 3.859 ± 0.033 | 4 |
| 23.21 ± 0.20 | 3.832 ± 0.033 | 3 |
| 23.40 ± 0.20 | 3.802 ± 0.032 | 12 |
| 24.03 ± 0.20 | 3.703 ± 0.031 | 8 |
| 24.77 ± 0.20 | 3.595 ± 0.029 | 25 |
| 25.90 ± 0.20 | 3.440 ± 0.026 | 8 |
| 26.15 ± 0.20 | 3.407 ± 0.026 | 9 |
| 27.59 ± 0.20 | 3.233 ± 0.023 | 5 |
| 27.84 ± 0.20 | 3.204 ± 0.023 | 4 |
| 28.24 ± 0.20 | 3.160 ± 0.022 | 2 |
| 28.68 ± 0.20 | 3.113 ± 0.021 | 3 |
| 29.26 ± 0.20 | 3.052 ± 0.021 | 2 |
| 39.81 ± 0.20 | 2.997 ± 0.020 | 1 |
| 30.08 ± 0.20 | 2.971 ± 0.019 | 3 |
| 30.47 ± 0.20 | 2.934 ± 0.019 | 1 |
| 30.85 ± 0.20 | 2.898 ± 0.018 | 2 |
| 31.17 ± 0.20 | 2.870 ± 0.018 | 2 |
| 31.55 ± 0.20 | 2.836 ± 0.018 | 1 |
| 32.12 ± 0.20 | 2.787 ± 0.017 | 6 |
| 32.51 ± 0.20 | 2.755 ± 0.017 | 2 |
| 32.92 ± 0.20 | 2.721 ± 0.016 | 2 |
| 4.60 ± 0.20 | 19.221 ± 0.874 | 13 |
| 10.36 ± 0.20 | 8.537 ± 0.168 | 18 |
| 11.11 ± 0.20 | 7.961 ± 0.145 | 65 |
| 13.69 ± 0.20 | 6.469 ± 0.095 | 41 |
| 16.08 ± 0.20 | 5.513 ± 0.069 | 100 |
| 16.73 ± 0.20 | 5.299 ± 0.064 | 17 |
| 17.82 ± 0.20 | 4.979 ± 0.056 | 14 |
| 20.42 ± 0.20 | 4.349 ± 0.043 | 36 |
| 20.82 ± 0.20 | 4.266 ± 0.041 | 35 |
| 21.59 ± 0.20 | 4.116 ± 0.038 | 21 |
| 22.08 ± 0.20 | 4.026 ± 0.036 | 13 |
| 22.31 ± 0.20 | 3.985 ± 0.036 | 22 |
| 22.44 ± 0.20 | 3.961 ± 0.035 | 26 |
| 23.40 ± 0.20 | 3.802 ± 0.032 | 12 |
| 24.77 ± 0.20 | 3.595 ± 0.029 | 25 |

Example 4C: Crystal Hygroscopicity and Chemical Stability Studies

Studies were also undertaken to assess the properties of the free base 6-{2-[1-(6-methyl-3-pyridazinyl)-4-piperidinyl]ethoxy}-3-ethoxy-1,2-benzoxazole of the invention. As reflected in FIG. 3, the weight of the free base crystalline vapendavir was measured (in terms of % change) versus % relative humidity. These results showed that Dynamic vapor sorption (DVS) was <0.1% of weight gain which thus reflected low hygroscopicity.

In tests conducted with regard to the chemical stability of the free base 6-{2-[1-(6-methyl-3-pyridazinyl)-4-piperidinyl]ethoxy}-3-ethoxy-1,2-benzoxazole of the invention, samples were placed in an LDPE bag, inside laminated foil bag, and HDPE keg and were monitored for appearance, water content (KF), assay ($^1$H-NMR), purity and related Substances (HPLC). This study showed no significant change in measured attributes over 25° C./60% rH over 36 months and over 40° C./75% rH over 6 months.

One advantage of the present crystalline form of 6-{2-[1-(6-methyl-3-pyridazinyl)-4-piperidinyl]ethoxy}-3-ethoxy-1,2-benzoxazole by virtue of these properties is that the physical size or mass of a tablet containing this new crystal form is less than that of the bis-dihydrogen phosphate form due to the present crystalline form can be made into effective compositions or tablets having lesser amounts than the equivalent prior art bisphosphate salt form.

Further, as shown in these tests, an additional advantage of the present crystalline form is that since it is in an anhydrous form, the new crystalline 6-{2-[1-(6-methyl-3-pyridazinyl)-4-piperidinyl]ethoxy}-3-ethoxy-1,2-benzoxazole does not absorb water and resists changing form during pharmaceutical formulation as observed when using the bis-dihydrogen phosphate form.

Example 5: Additional Studies of Physical Characteristics and Comparative Studies of Crystalline Free Base Vapendavir and the Bis-Dihydrogen Phosphate Salt Form of Vapendavir Additional physical and chemical characteristics of the present free base 6-{2-[1-(6-methyl-3-pyridazinyl)-4-piperidinyl]ethoxy}-3-ethoxy-1,2-benzoxazole form were determined including certain studies regarding comparative data.

A further analysis of the anhydrous crystalline free base vapendavir of the invention as prepared above including HPLC and NMR data. Both the HPLC (relative retention time) and the NMR data were able to confirm correlation to the reference standard. The specific 1H NMR details of the obtained NMR data were as follows:

$^1$H NMR (CDCl$_3$): δ7.47 (d, 1H, J=9 Hz), 7.06 (d, 1H, J=9 Hz), 6.88-6.85 (m, 2H), 6.84 (s, 1H), 4.47 (q, 2H, J=7 Hz), 4.33 (d, 2H, J=13 Hz), 4.08 (t, 2H, J=6 Hz), 2.92 (t, 2H, J=13 Hz), 2.53 (s, 3H), 1.75-1.90 (m, 5H), 1.50 (t, 3H, J=7 Hz), 1.34-1.38 (m, 2H).

As a result of the anhydrous free base crystalline form of the invention, improved treatment of a picornavirus such as HRV will be possible because of the potential improved patient adherence due to smaller tablet sizes for the equivalent dose of the freebase vapendavir of the present invention versus the bis phosphate form used in the prior art.

Figure 7A:
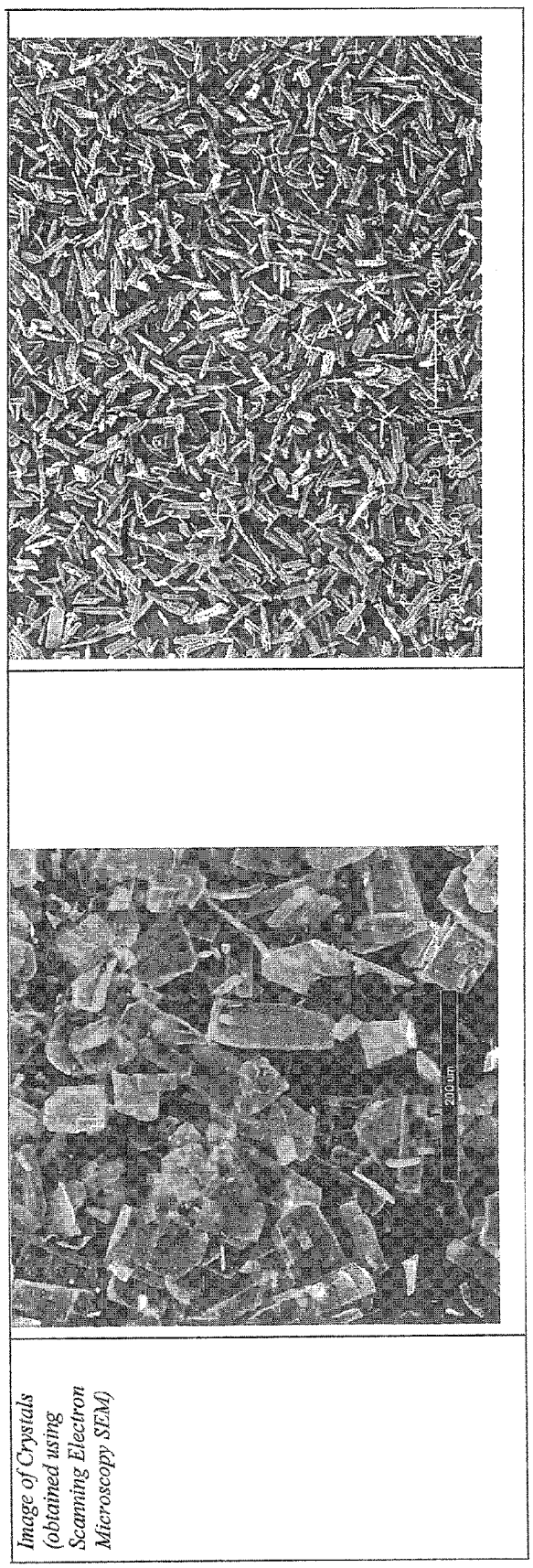
FIGS. 7A through 7C show a series of scanning electron microscope (SEM) images at various scales showing the anhydrous free base crystalline form of 6-{2-[1-(6-methyl-3-pyridazinyl)-4-piperidinyl]ethoxy}-3-ethoxy-1,2-benzoxazole, with XRPD characterization defined elsewhere herein, in a needle-like crystal habit after wet milling in accordance with one example of the present disclosure (right side) and the plate-like crystal habit of 6-{2-[1-(6-methyl-3-pyridazinyl)-4-piperidinyl]ethoxy}-3-ethoxy-1,2-benzoxazole bis-dihydrogenphosphate salt with XRPD characterization according to WO2009/143571.
Figure 7B:
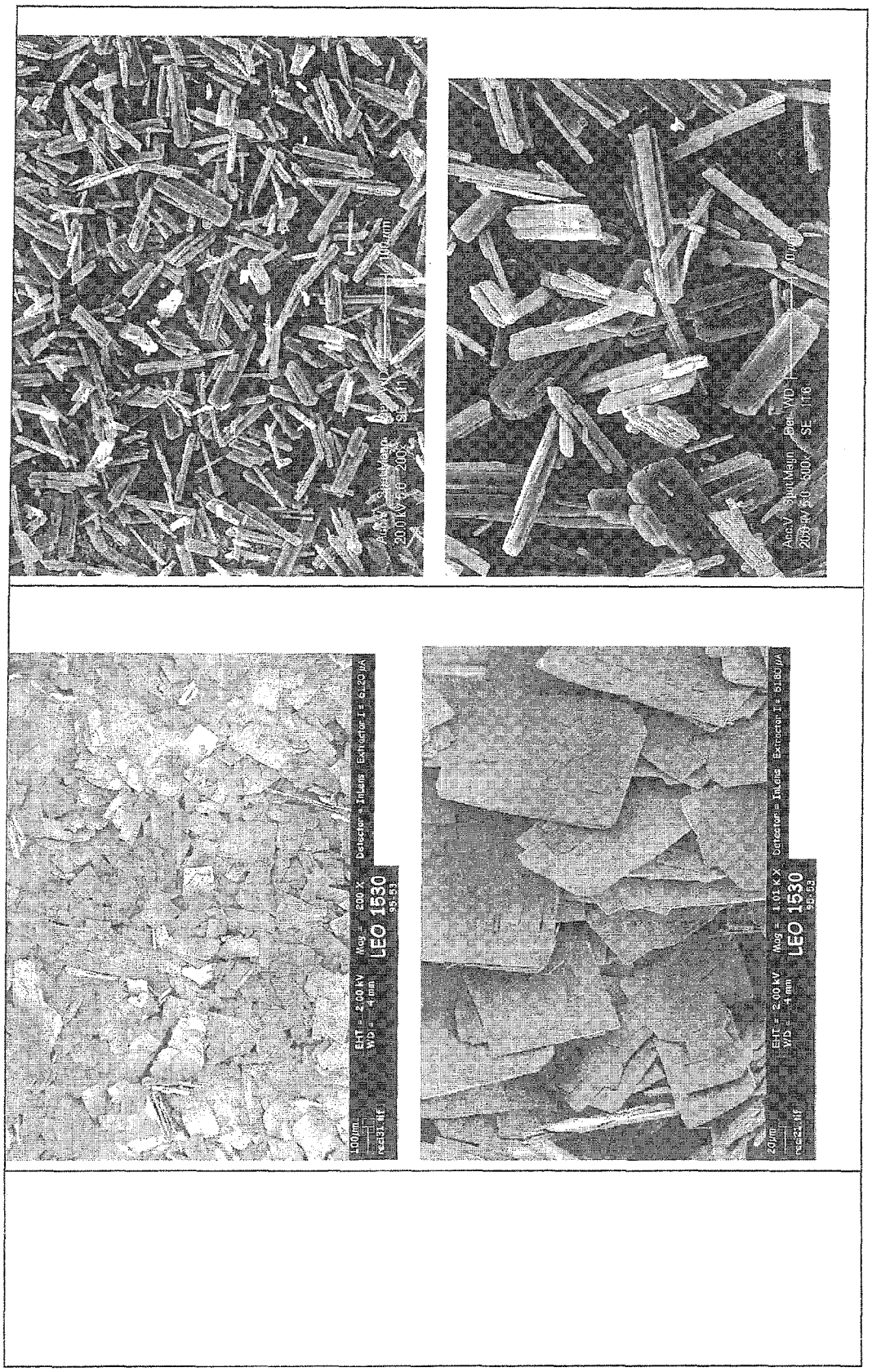
Figure 7C:
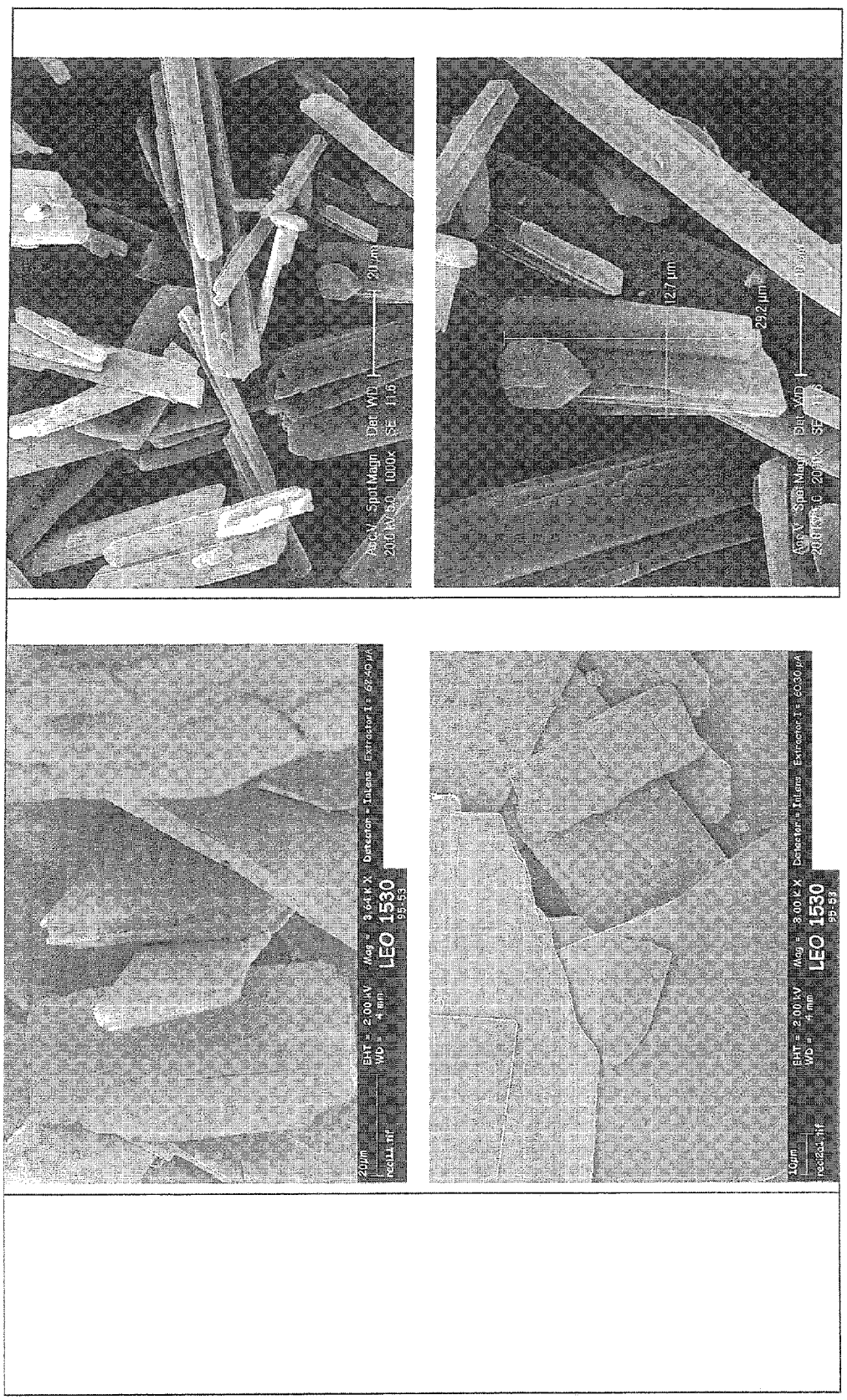

Additional testing further confirmed the difference between the anhydrous crystalline free base vapendavir of the present invention and the prior bis-dihydrogen phosphate salt form of vapendavir. Differences were shown in XPRD data between the two (see FIG. 4), and scanning electronic micrograph photographs confirmed that the prior bis-dihydrogen phosphate vapendavir had a plate-like crystal form (see FIGS. 7A-7C, left side), whereas the anhydrous free base crystalline vapendavir of the present invention had a needle-like form (see FIGS. 7A-7C, right side)

Example 6: Process for Tablet Manufacture of Crystal Free Base Form of 6-{2-[1-(6-methyl-3-pyridazinyl)-4-piperidinyl]ethoxy}-3-ethoxy-1,2-benzoxazole In accordance with the present invention, the anhydrous free base crystal form of vapendavir was formed into a tablet suitable for oral administration to a patient in need thereof. The schematic of this procedure is included as FIG. 8. In this exemplary process, the free base crystal vapendavir is combined with maltodextrin, and sodium starch glycolate into a mixture to which purified water is added, and the ingredients are mixed and granulated and then fed into a fluid bed dryer to be dried. Following drying, the components are milled by passage through a 1.14 millimeter screen, followed by blending for 20 minutes of the screen ingredients with mannitol 400 and silicified microcrystalline cellulose. Next, the components are further blended with magnesium stearate and then compressed and coated to produce the final tablet. The tablet was coated with PVA coating Opadry 03F2300015. The tablets can be manufactured to any suitable size, for examples, a tablet with a 300 mg dose.

In one exemplary embodiment, the free base anhydrous crystalline vapendavir was formed into a 300 mg dose tablet with the formulation as follows:

| Excipient | % w/w |
| --- | --- |
| Vapendavir free base | 56 |
| Maltodextrin | 20 |
| Silicified Microcrystalline cellulose | 14 |
| Mannitol 400 | 6 |
| Sodium Starch glycolate | 1.5 |
| Mag Stearate | 0.7 |
| Opadry (Orange) | qs |

Example 7: Polymorphism Studies

Polymorphism studies of the anhydrous free base 6-{2-[1-(6-methyl-3-pyridazinyl)-4-piperidinyl]ethoxy}-3-ethoxy-1,2-benzoxazole form of the invention were also conducted. Experiments included tests such as fast evaporation, crash cooling, hot/cold slurries, and melt and freeze. The collected data indicated that the preferred single polymorph (Form A) of the anhydrous crystalline free base vapendavir was obtained from solvent based experiments, and no solvates or hydrates were observed. Competitive slurry testing of Form A with an alternative, but not fully characterized polymorph, also confirms Form A to be the most stable thermodynamic form.

Example 8: Suspension of Crystalline Freebase Vapendavir

The ability to provide a pharmaceutical composition in the form of a suspension has been very important in particular with regard to pediatric medicine as this form may be necessary to administer the active ingredient to young patients. In this regard, the present inventors determined that a suitable form of crystalline free base vapendavir could be manufactured wherein the needle-like particles of the crystal were micronized to a smaller but more uniform particle size. The ability of the crystalline free base to be micronized and yet continue to maintain its active form was an improvement over previous forms of vapendavir such as the phosphate salt form which formed a plate-like crystal form and could not be micronized and maintain its active properties.

The following materials as set forth in Table 11 were used in formulation development:

TABLE 11

Raw Material Identification

| Sample | Trade Name | Manufacturer | Lot |
| --- | --- | --- | --- |
| BTA-798 Free Base (Non-Micronized) | Vapendavir | Carbogen Amcis | NE-D21602-Batch-01-2013 |
| BTA-798 Free Base (Micronized) | Vapendavir | Carbogen Amcis | NE-D21602-Batch-01-2013 |
| Sodium Lauryl Sulfate | Sodium Lauryl Sulfate | Fisher | 140277 |
| Microcrystalline Cellulose and Carboxymethylcellulose Sodium | Avicel RC-591 | FMC | DM14827246 |
| Sucralose | Splenda | Tate & Lyle | XM2M036301 |
| Polysorbate 80 | Polysorbateor 80 | Spectrum | 2DH0335 |
| Glycerin | Glycerin | Spectrum | 214072447B |
| Sucrose | Sucrose | Fisher | 121768 |
| Xanthan Gum | Xantural 11k | CP Kelco | 330308K |
| Propylene Glycol | Propylene Glycol | Spectrum | 2GH0075 |
| Butylparaben | Butylparaben | Spectrum | 2EA0365 |
| Mixed Berry | Mixed Berry | Wild Flavors | 14072447B |
| DI Water | Water | Emerson Resources | In-House |
| Citric Acid Monohydrate | Citric Acid Monohydrate | BDH | 95097 |
| Trisodium Salt Dihydrate | Trisodium Salt Dihydrate | Acros | B0137689B |

Prior to formulation development, the solubility of the crystalline freebase form of vapendavir (or "BTA-798") API was determined in several pH buffers. Detailed solubility determination results are shown herein including in Table 12 below:

TABLE 12

Drug Substance Solubility Summary

| pH | BTA-798 freebase (mg/mL) NE-021602-BATCH-01-2013 |
| --- | --- |
| 1.2 | ≥0.6 |
| 2.1 | 0.37 |
| 3.0 | 0.11 |
| 4.0 | 0.01 |
| 5.0 | ND |
| 6.0 | ND |
| 7.0 | ND |
| 8.0 | ND |

ND = Not Detected

In these tests, the crystalline free base vapendavir (BTA-798) had the lowest solubility between pH 5.0-8.0 indicating that this pH range was the most desirable for a suspension formulation.

An initial placebo formulation not containing vapendavir was assessed for physical appearance and viscosity.

| Sample | CLF13-106 (Placebo) |
| --- | --- |
| BTA-798 Free Base (Non-Micronized) | — |
| Sodium Lauryl Sulfate | — |
| Microcrystalline Cellulose and Carboxymethylcellulose Sodium | 1.30% |
| Xanthan Gum | — |
| Polysorbate 80 | 0.10% |
| Sodium Benzoate | 0.20% |
| Propylene Glycol | — |
| Butylparaben | — |
| Glycerin | 5.00% |
| Flavor | 0.10% |
| Sucralose | — |
| Sucrose | 40.00% |
| 0.1M Citric Acid | — |
| DI Water | 50.90% |

TABLE 13

Appearance:

| Sample | Lot# | Appearance |
| --- | --- | --- |
| BTA-798 Freebase Suspension Placebo | CLF13-106 | A translucent homogeneous suspension |

TABLE 14

Viscosity (@ 25° C. Spindle S18):

| Sample | Lot# | Viscosity (cP) |
| --- | --- | --- |
| Suspension Placebo | CLF13-106-23 | 18.1 |

For the following formulations, a 0.1M citric acid buffer was added to the suspension to achieve a pH of 5.5. The pH of the placebo suspensions were taken to determine if the suspension would remain 5.5 after processing. The preservative was changed from sodium benzoate to butylparaben, which is a more effective preservative for the target pH. Additionally, xanthan gum was added to increase the viscosity of the suspension.

After determining the 0.1M citric acid buffer provided sufficient buffering, but determining that the viscosity needed to be reduced, a micronized version of the crystalline free base vapendavir was assessed. The vapendavir was jet-milled using conventional jet-milling equipment, in this case an NGMP-2 jet mill manufactured by Sturdevant, Inc. using a flexible containment unit.

Figure 19:
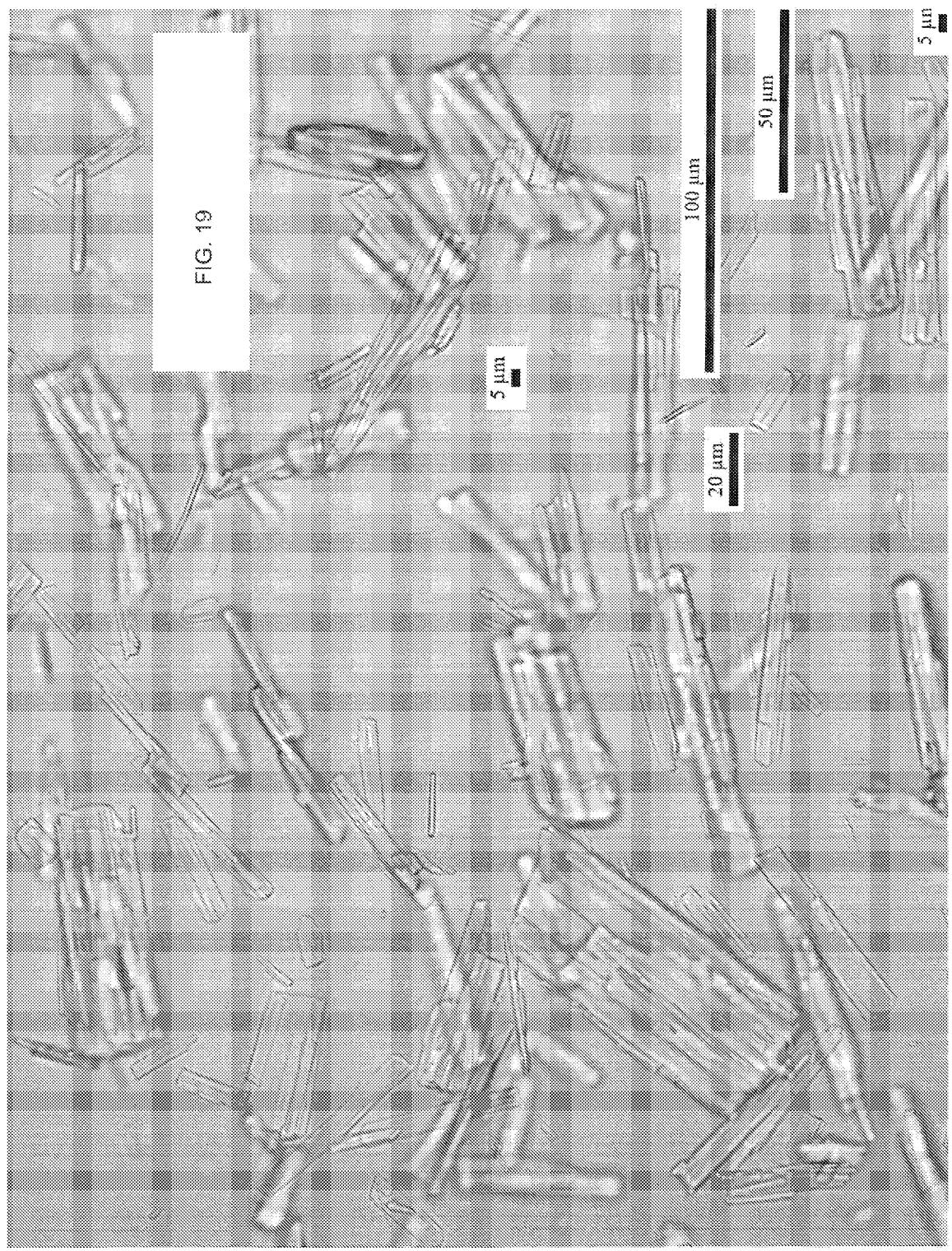
FIG. 19 is a micrograph showing particles from the compound of the invention with the needle-like crystal habit prior to micronization.
Figure 20:
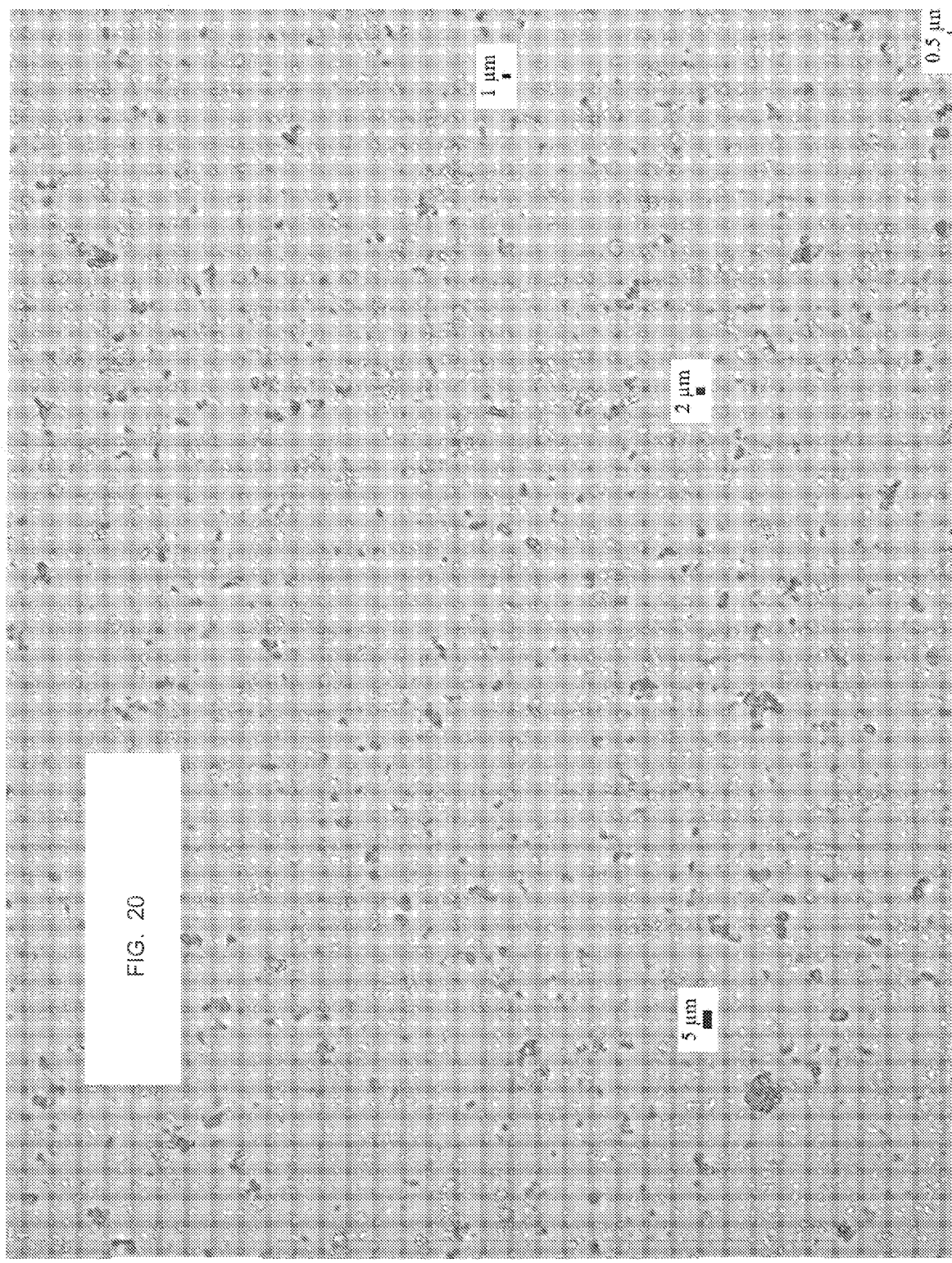
FIG. 20 is a micrograph showing particles from the compound of the invention after micronization.

These tests showed the successful micronization of crystalline free base vapendavir, and the resulting form had an average particle size of less than 5 microns which produced a smaller particle, with greater surface area to enhance dissolution. The free-base form was stable to this processing. A micrograph of the crystalline free base form prior to micronization is shown in FIG. 19, and a micrograph of the micronized version showing average particle sizes under 5 microns is shown in FIG. 20.

Prior to micronization, particle sizes ranged from roughly 15 to 100 microns.

However, after micronization, particle sizes ranged from roughly 2 to 5 microns.

This micronized version of crystalline free base vapendavir was then tested for physical appearance, viscosity, particle size, pH, and dispersibility/settling rate, as shown below

TABLE 15

Formulations Comparison:

| Sample | PS01-06 (Placebo) | PS01-10 |
| --- | --- | --- |
| BTA-798 Free Base (Micronized) | — | 2.40% |
| Microcrystalline Cellulose and Carboxymethylcellulose Sodium | 1.50% | 1.50% |
| Xanthan Gum | 0.34% | 0.34% |
| Polysorbate 80 | 0.20% | 0.20% |
| Propylene Glycol | 1.00% | 1.00% |
| Butylparaben | 0.02% | 0.02% |
| Glycerin | 5.00% | 5.00% |
| Flavor | 0.10% | 0.10% |
| Sucrose | 40.00% | 40.00 |
| 0.1M Citric Acid | 49.76% | 49.44 |

TABLE 16

Process Procedure lot # PS01-06/PS01-10:

1. Dispense the required quantity of 0.1M citric acid buffer.
2. Begin mixing the 0.1M citric acid buffer with a moderate shear mixing blade. Disperse the required quantity of Avicel RC-591 in the 0.1M citric acid buffer.
3. Add the sucrose, glycerin, PS80 and mix until dissolved.
4. While the sucrose solution is mixing, dispense the propylene glycol into a small beaker.
5. Dispense the butylparaben and add to the propylene glycol. Mix until dissolved.
6. Add the flavor to the paraben solution and continue to mix until dissolved.
7. Add the paraben solution to the sucrose solution.
8. Add the xanthan and mix until dispersed.
9. Dilute to 500 mL with 0.1M citric acid buffer. Record weight of additional 0.1M citric acid buffer required.
10. Screen the BTA798 free base through a US 20 mesh and dispense the required amount into suspension with continuous mixing.[1]

[1]This process step was only for PS01-10

TABLE 17 pH Analysis:

| Sample | #190 | pH |
| --- | --- | --- |
| BTA-798 Freebase Suspension Placebo | PS01-06 | 5.55 |
| BTA-798 Freebase Suspension | PS01-10 | 5.54 |

TABLE 18

Appearance:

| Sample | Lot# | Appearance |
| --- | --- | --- |
| BTA-798 Freebase Suspension Placebo | PS01-06 | A translucent homogeneous suspension |
| BTA-798 Freebase Suspension | PS01-10 | A white homogeneous suspension |

TABLE 19

Viscosity (@ 25° C. Spindle S18):

| Sample | Lot# | Viscosity (cP) |
|---|---|---|
| BTA-798 Freebase Suspension Placebo | PS01-06 | 50.7 |
| BTA-798 Freebase Suspension | PS01-10 | 46.6 |

Figure 21:
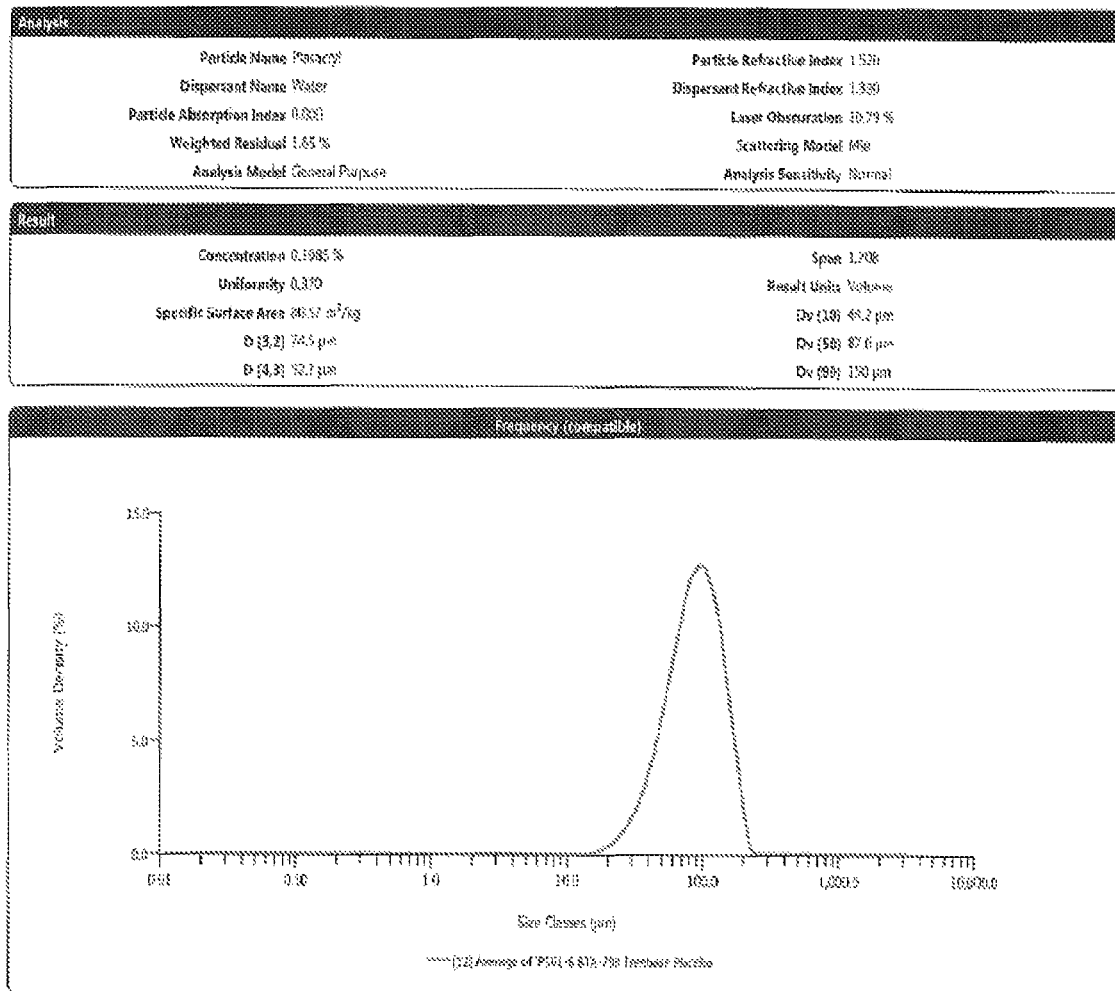
FIG. 21 is a graph of particle size analysis of a suspension placebo as described further herein.
Figure 22:
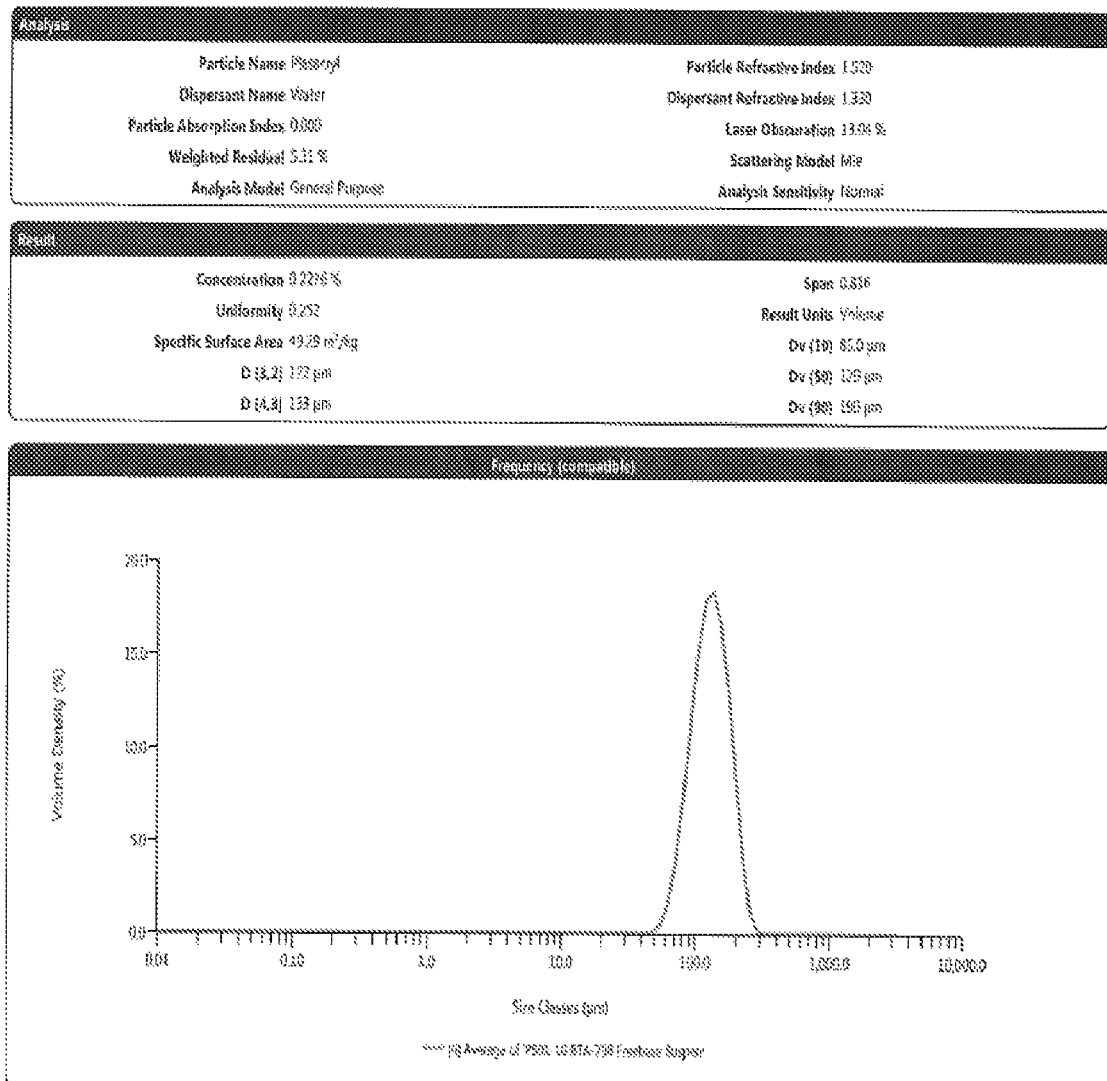
FIG. 22 is a graph of particle size analysis of a suspension in accordance with the invention as described further herein.

A comparison of particle size between the active and placebo was performed using a Mastersizer™ 3000 laser diffraction particle size analyzer. The particle size analysis can be observed in FIGS. 21 and 22. As indicated in the attached drawing figures, the freebase suspension of the micronized vapendavir has a much more uniform particle size than the placebo.

The D10/50/90 observed for the BTA-798 freebase suspension were slightly higher (85.0/129/190 μm) than was observed in the placebo suspension (44.2/87.6/150 μm). This observation may indicate API aggregation within the suspension. If API aggregation is occurring, it is not considered to have a negative impact on the product based on the dispersibility/settling rate data.

A dispersibility/settling rate evaluation was performed on the BTA-798 freebase suspension. This test examined the uniformity of the API in the suspension after shaking and the subsequent settling rate of the API in the suspension. Samples were taken from the top and bottom of the suspension bottle immediately after shaking (T=0), and then again after 1 hour and 4 days. All samples were assayed via HPLC.

TABLE 20

HPLC Parameters

| Column: | Waters X Bridge C 18, 3.5 1 Jm, 150 × 46 mm |
|---|---|
| Column Temperature: | 35° C. |
| UV Detection: | 252 nm |
| Flow Rate: | 1.0 mL/minute |
| Mobile Phases: | A: 10 mM Phosphate buffer, pH 3.0<br>B: MeOH |

| Gradient: | Time (min) | % A | % B |
|---|---|---|---|
| | 0.0 | 60 | 40 |
| | 25.0 | 15 | 85 |
| | 27.0 | 15 | 85 |
| | 28.0 | 60 | 40 |
| | 32.0 | 60 | 40 |

TABLE 21

Dispersibility/Settling Rate Evaluation

| Sample | Sampling Location | % LC | % LC Ave. |
|---|---|---|---|
| PS01-10 t = 0 | Top | 98.7 | 100.6 |
| | Bottom | 102.6 | |
| PS01-10 1 hour | Top | 100.2 | 99.9 |
| | Bottom | 99.6 | |
| PS01-10 4 days | Top | 98.4 | 100.9 |
| | Bottom | 103.4 | |

The T=0 assay results of the top and bottom samples were in close agreement indicating that the suspension was uniform after shaking. Additionally, the samples taken after 1 hour and 4 days were in close agreement indicating that significant settling of the API did not occur over a 4 day period.

As a result of the above processes, a pediatric suspension containing micronized crystalline freebase vapendavir was developed providing desirable characteristics with regards to appearance, viscosity, pH, drug suspendability, and organoleptic properties. The following is an example of a suspension that will be useful in accordance with the invention:

| Sample | Lead Formulation |
|---|---|
| BTA-798 Free Base (Micronized) | 2.40% |
| Microcrystalline Cellulose and Carboxymethylcellulose Sodium | 1.50% |
| Xanthan Gum | 0.34% |
| Polysorbate 80 | 0.20% |
| Propylene Glycol | 1.00% |
| Butylparaben | 0.02% |
| Glycerin | 5.00% |
| Flavor | 0.10% |
| Sucrose | 40.00 |
| 0.1M Citric Acid | 49.44 |

Example 9: Vapendavir Freebase Solid Oral Dosage Form

In accordance with the present invention, it was desired to obtain additional solid pharmaceutical dosage forms such as a tablet which could be suitably used for oral administration of the crystalline free base vapendavir of the invention. In this regard, both non-micronized and micronized crystal free base vapendavir were tested in an effort to develop suitable oral dosage forms with sufficient solubility properties which could maintain the properties of the active ingredient. Tests were conducted using the following materials:

TABLE 22

Raw Material Identification

| Sample | Trade Name | Manufacturer | Lot |
|---|---|---|---|
| Vapendavir Free Base (Non-Micronized) | Vapendavir | Carbogen Amcis | NE-D21602-Batch-01-2013 |
| Vapendavir Free Base (Micronized) | Vapendavir | Carbogen Amcis | NE-D21602-Batch-01-2013 |
| Vapendavir Phosphate Salt | Vapendavir | Institute of Drug Technology | NE-022743-Batch-01-2010 |
| Vapendavir 300 mg Tablets | Vapendavir 300 mg Tablets | Biota | C14011 |
| Vapendavir 300 mg Tablets | Vapendavir 300 mg Tablets | Biota | C14002B |
| Sodium Lauryl Sulfate | Sodium Lauryl Sulfate | Fisher | 140277 |
| Polysorbate 80 | Polysorbate 80 | Spectrum | 2DH0335 |
| Poloxamer | Kolliphor P188 | BASF | WPWI625C |
| Soluplus | Soluplus | BASF | 84414368E0 |
| PVP k29/32 | Plasdone K-29/32 | ISP | 052299950 |
| Maltodextrin | Maltrin | GPC | M1031332 |
| Sodium Starch Glycolate | Explotab | JRS Pharma | 4111012087 |
| SMCC 90 | Prosolv | JRS Pharma | P9B0L62X |
| Magnesium Stearate | Magnesium Stearate | Mallinckrodt | J35596 |

TABLE 22-continued

Raw Material Identification

| Sample | Trade Name | Manufacturer | Lot |
|---|---|---|---|
| Dextrose, Anhydrous | Dextrose, Anhydrous | Avantor | 0000083939 |
| Size 0 Gelatin Swedish Orange Capsules | Swedish Orange Capsules | Capsugel | 71121481 |

Prior to formulation development, a dissolution method was developed to provide better discrimination between dissolution profiles of vapendavir formulations than was previously observed using a method designed for standard quality control purposes. The dissolution parameters used in the tests are summarized below:

TABLE 23

Dissolution Parameters

| | |
|---|---|
| Dissolution Apparatus: | Apparatus 1 (Basket) |
| Dissolution Media: | pH 2.1 buffer |
| Dissolution Volume: | 900 mL |
| RPMs | 50 |
| Time Point | 15, 30, and 45 minutes |

The following formulations were tested for dissolution to provide an initial comparison of previously manufactured formulations using the discriminating dissolution parameters. Formulation lot# CU05-095(4) was representative of the vapendavir phosphate salt capsule formulation that was previously studied in human clinical studies. Formulation lot# CU05-093 was prepared to evaluate the vapendavir phosphate salt formulation against a comparable vapendavir freebase formulation. Formulation lots# C14011 and C14002B were vapendavir freebase tablet batches that were previously manufactured for human clinical trials.

Lots CU05-093 and CU05-095(4) are formulations with two components. These two components were mixed in a V-blender and filled into 00EL gelatin capsules.

TABLE 24

Initial Formulations Comparison:

| Sample | CU05-095(4) | CU05-093 | C14011 | C14002B |
|---|---|---|---|---|
| Vapendavir Free Base (Non-Micronized) | — | 44.5% | 54.1% | 54.1% |
| Vapendavir Phosphate Salt | 68.1% | — | — | — |
| Maltodextrin | — | — | 19.5% | 19.5% |
| Sodium Starch Glycolate (Explotab) | — | — | 5.8% | 5.8% |
| Silicified Microcrystalline Cellulose (Prosolv SMCC 90) | — | — | 13.4% | 13.4% |
| Magnesium Stearate | — | — | 0.7% | 0.7% |
| Dextrose, Anhydrous | 31.9% | 55.5% | — | — |
| Opadry 03F230015 | — | — | 3.8% | 3.8% |

Figure 23A:
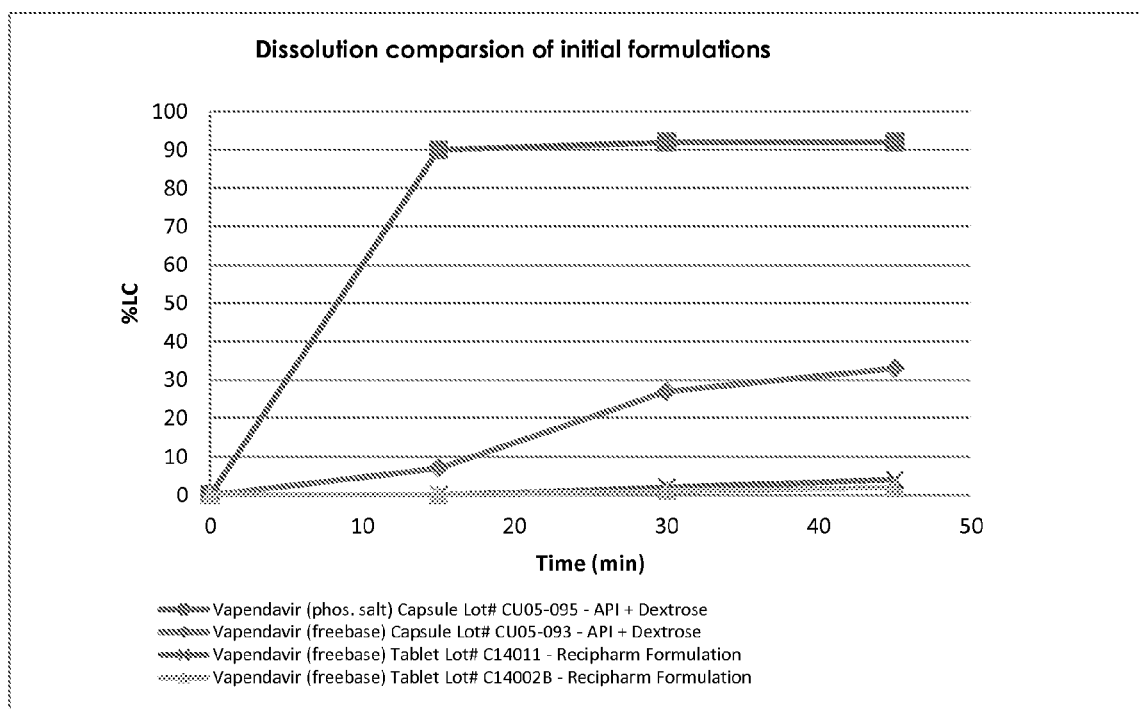
FIG. 23A is a graph of a dissolution comparison as described further herein.

The dissolution comparison of initial formulations is showed in FIG. 23A.

Following the initial characterization, formulations were prepared that were similar to the previously manufactured vapendavir freebase tablet, however these formulations omitted the use of mannitol and added sodium lauryl sulfate as a surfactant to improve drug wetting. Using this base formulation, four batches were manufactured to evaluate the effect of micronized/non-micronized drug substance and tablet/capsule dosage forms.

TABLE 25

API Micronization and Dosage form Comparison:

| Sample | CU05-129-01 | CU05-129-12 | CU05-128-01 | CU05-128-12 |
|---|---|---|---|---|
| Vapendavir Free Base (Non-Micronized) | — | — | 52.8% | 52.8% |
| Vapendavir Free Base (Micronized) | 52.8% | 52.8% | — | — |
| Sodium Lauryl Sulfate | 2.0% | 2.0% | 2.0% | 2.0% |
| Maltodextrin | 18.0% | 18.0% | 18.0% | 18.0% |
| Sodium Starch Glycolate (Explotab) | 6.0% | 6.0% | 6.0% | 6.0% |
| Silicified Microcrystalline Cellulose (Prosolv SMCC 90) | 20.5% | 20.5% | 20.5% | 20.5% |
| Magnesium Stearate | 0.8% | 0.8% | 0.8% | 0.8% |

TABLE 26

Process Procedure lot # CU05-128/129

1. Screen the API through a US 20 mesh screen
2. Add the screened drug substance, sodium lauryl sulfate, sodium starch glycolate, and maltodextrin to the 1 L bowl of the high shear granulator.
3. Mix for 2 minutes with mixing blade only at 870 rpm.
4. With both mixer (870 rpm) and chopper (1800 rpm) at low setting, add water until sufficient granulation is observed.
5. Place the wet granulation on a tray and dry in an oven at 40° C.
6. Screen the granulation through a US 20 mesh.
7. Blend the granulation and SMCC 90 for 10 minutes in a V-Blender.
8. Screen the magnesium stearate through a US 20 mesh and add to the blend.
9. Blend for an additional 2 minutes.
10. Fill one portion of the blend into a size 00EL gelatin capsules.[1]
11. Compress remaining portion of the blend into tablets.[2]

[1]CU05-XXX-12
[2]CU05-XXX-01

Figure 23B:
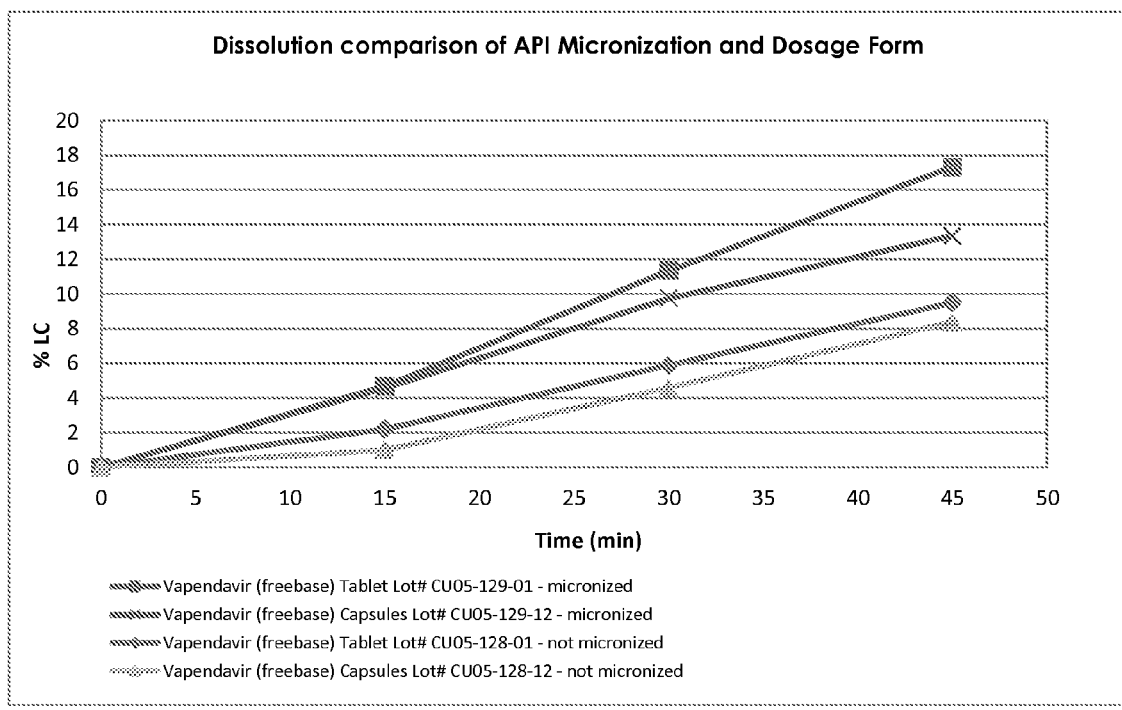
FIG. 23B is a graph of a dissolution comparison as described further herein.

A dissolution comparison of API Micronization and Dosage form is shown in the accompanying FIG. 23B.

The dissolution results showed negligible differences in the dissolution rates between the micronized and non-micronized vapendavir freebase formulations. The potential dissolution benefit of increased surface area from micronizing the drug substance may have been negated by aggregation of the drug particles due to its hydrophobicity. In order to improve surface wetting of the drug, formulations containing a variety of surfactant/wetting agents were evaluated.

TABLE 27

Wetting Agent Comparison:

| Sample | CU05-095(4) | CLF13-113 | CLF13-112 | CLF13-114 | CU05-093 | CLF13-115 | CU05-128-12 |
|---|---|---|---|---|---|---|---|
| Vapendavir Free Base (Non-Micronized) | — | 67.0% | 67.0% | 67.0% | 44.5% | 67.0% | 52.8% |
| Vapendavir Phosphate Salt | 68.1% | — | — | — | — | — | — |
| Poloxamer (KolliphorP188) | — | 25.4% | — | — | — | — | — |
| Sodium Lauryl Sulfate | — | — | — | — | — | — | 2.0% |
| Soluplus | — | — | — | 25.4% | — | — | — |
| Providone K29/32 | — | — | — | — | — | 25.4% | — |
| Polysorbate 80 | — | — | 2.5% | — | — | — | — |
| Maltodextrin | — | — | 22.8% | — | — | — | 18.0% |
| Sodium Starch Glycolate (Explotab) | — | 7.6% | 7.6% | 7.6% | — | 7.6% | 6.0% |
| SMCC 90 | — | — | — | — | — | — | 20.5% |
| Magnesium Stearate | — | — | — | — | — | — | 0.8% |
| Dextrose, Anhydrous | 31.9% | — | — | — | 55.5% | — | — |

TABLE 28

Process Procedure lot # CLF13-112/113/114/115

1. Screen the API through a US 20 mesh screen
2. Add the screened API, sodium starch glycolate, wetting agent[1] and maltodextrin to the 1 L bowl of the high shear granulator.
3. Mix for 2 minutes with mixing blade only at 870 rpm.
4. Dispense the required quantity of polysorbate 80 into a beaker. Add to it appropriate amount of water.[2]
5. With both mixer (870 rpm) and chopper (1800 rpm) at low setting, add water[3] until sufficient granulation is observed.
6. Place the wet granulation on a tray and dry in an oven at 40° C.
7. Screen the granulation through a US 20 mesh.
8. Fill granulation into a size 00EL gelatin capsules.[1]

[1]Poloxamer, Soluplus, and PVP k29/32
[2]This step was only performed for the Polysorbate 80 formulation.
[3]The water for the Polysorbate 80 formulation is a mixture of PS80 and water.

Figure 24A:
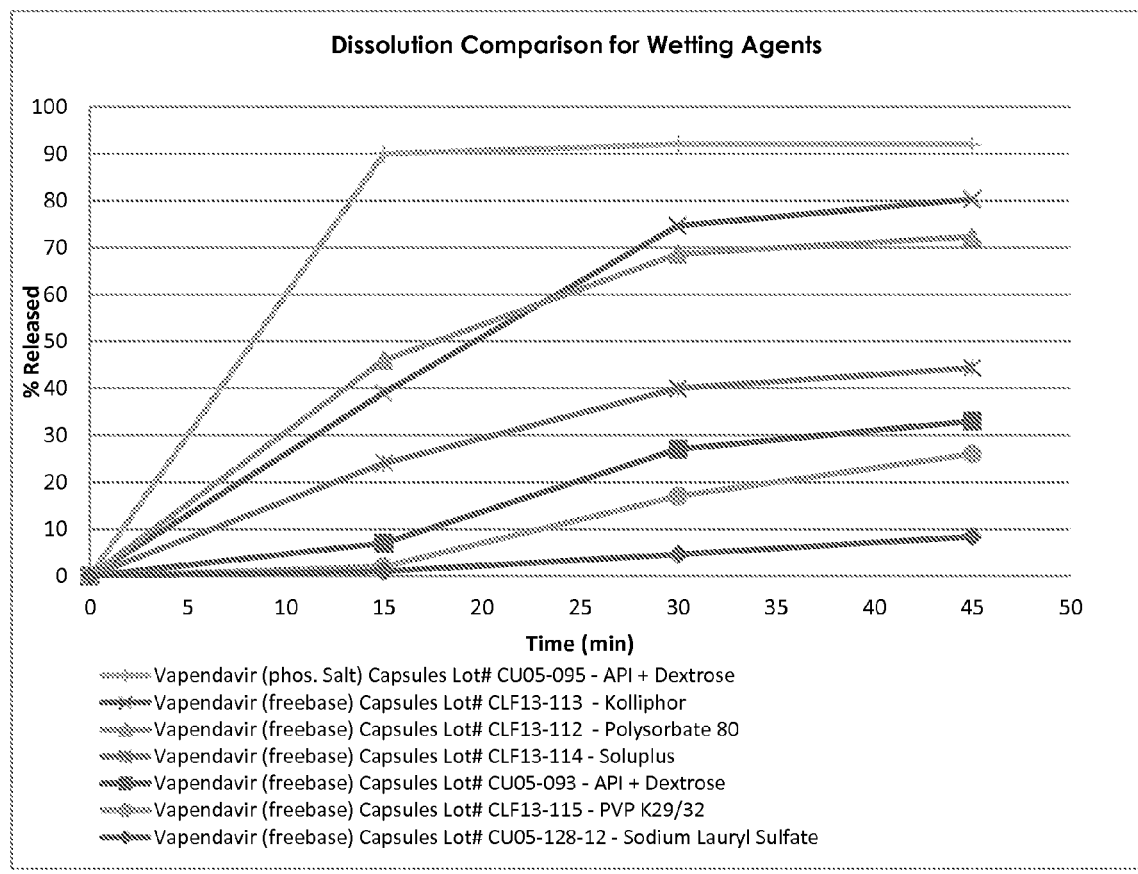
FIG. 24A is a graph of a dissolution comparison as described further herein.

A dissolution comparison using various wetting agents is shown in the accompanying FIG. 24A.

The formulations with poloxamer and polysorbate 80 had the most dramatic effect on dissolution rate. Soluplus provided a modest improvement on the dissolution rate and povidone K29/32 did not improve the dissolution rate. This was most likely due to slow disintegration caused by the formation of a hydrogel inside the dissolution basket.

An infinity time point was added to the dissolution profile by increasing to basket speed to 150 rpm for 30 minutes before sampling.

TABLE 29

Dissolution Comparison Wetting Agents (Infinity Point)

| Formulation | Infinity Point (% released) |
|---|---|
| Vapendavir (freebase) Capsules Lot# CLF13-112 - Polysorbate 80 | 77% |
| Vapendavir (freebase) Capsules Lot# CLF13-113 - Kolliphor | 84% |
| Vapendavir (freebase) Capsules Lot# CLF13-114 - Soluplus | 50% |
| Vapendavir (freebase) Capsules Lot# CLF13-115 - PVP K29/32 | 82% |

The infinity point data supports the theory that the slow dissolution profile observed for the povidone formulation was caused by slow disintegration because the drug release at the infinity point was comparable to other wetting agents. The increase basket speed expedited the disintegration of the hydrogel and allowed the drug to release into solution.

From the wetting agents that were evaluated, poloxamer was chosen for further study. Formulations were prepared to evaluate the use of poloxamer with micronized and non-micronized drug substance. Also, formulations were prepared to evaluate lower use levels of poloxamer.

TABLE 30

Micronized API and Poloxamer Level Comparison

| Sample | CU05-095(4) | CLF13-113 | PS01-08 | PS01-12 |
|---|---|---|---|---|
| Vapendavir Free Base (Non-Micronized) | — | 67.0% | — | 76.7% |
| Vapendavir Free Base (Micronized) | — | — | 67.0% | — |
| Vapendavir Phosphate Salt | 68.1% | — | — | — |
| Poloxamer (Kolliphor P188) | — | 25.4% | 25.4% | 14.5% |
| Sodium Starch Glycolate (Explotab) | — | 7.6% | 7.6% | 8.7% |
| Dextrose, Anhydrous | 31.9% | — | — | — |

TABLE 31

Process Procedure lot # CLF13-112/113/114/115

1. Screen the API through a US 20 mesh screen.
2. Add the screened drug substance, sodium starch glycolate, poloxamer and maltodextrin to the 1 L bowl of the high shear granulator.
3. Mix for 2 minutes with mixing blade only at 870 rpm.
4. With both mixer (870 rpm) and chopper (1800 rpm) at low setting, add water until sufficient granulation is observed.
5. Place the wet granulation on a tray and dry in an oven at 40° C.
6. Screen the granulation through a US 20 mesh.
7. Fill granulation into a size 00EL gelatin capsules.[1]

Figure 24B:
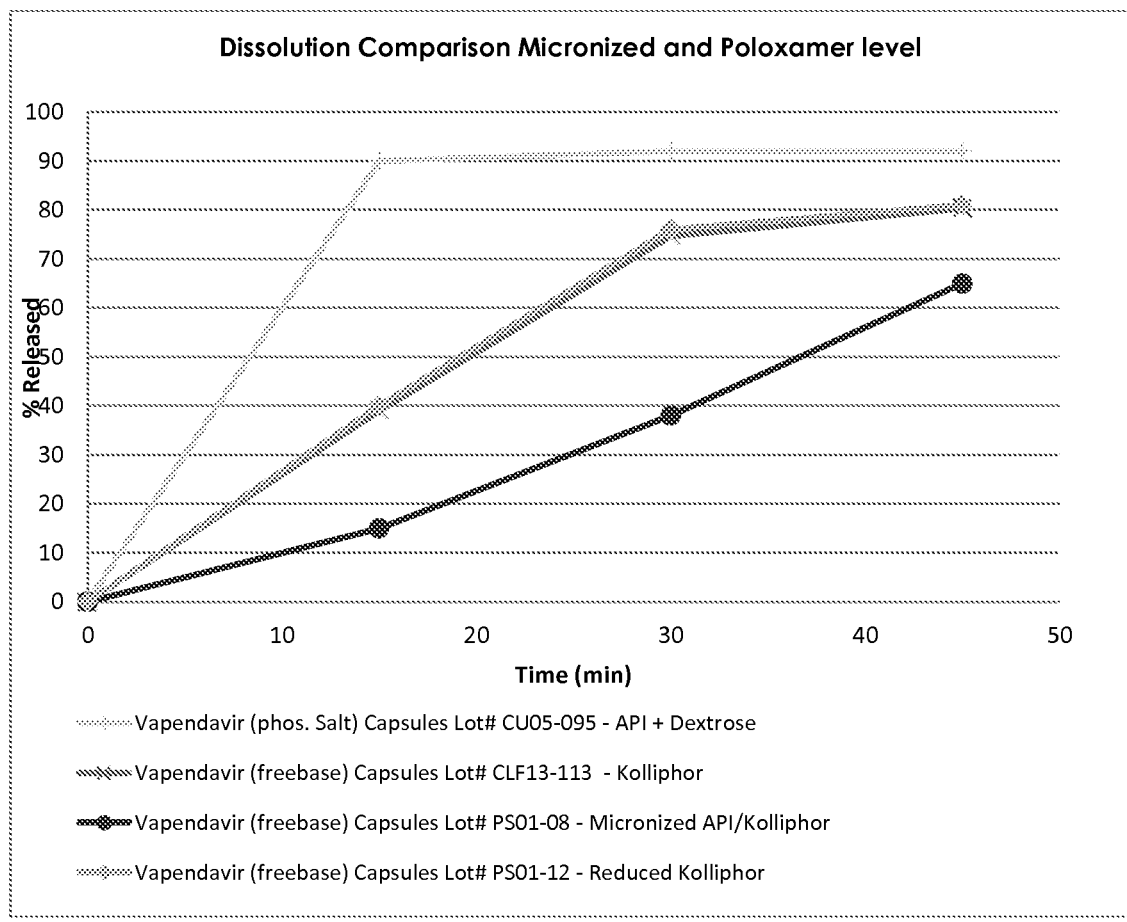
FIG. 24B is a graph of a dissolution comparison as described further herein.

A dissolution comparison based on Micronized and Poloxamer Level is shown in the accompanying FIG. 24B.

There was no difference in the dissolution profiles between the different levels of poloxamer indicated the poloxamer use level can be reduced in the formulation. This will minimize the size of the final dosage form and potential compliance with the FDA's inactive ingredient guide (the limits for poloxamer in an oral capsule is ambiguous). Using the micronized drug substance decreased the dissolution rate when compared to non-micronized drug substance. This was most likely due physical differences in the granules produced with the micronized/non-micronized material. The micronized material produced larger granules than the non-micronized material. These larger granules may have been more dense and slower to disintegrate causing a slower dissolution rate.

An infinity point was collected for these formulations.

TABLE 32

Dissolution Comparison Micronized and Poloxamer Level (Infinity Point)

| Formulation | Infinity Point (% released) |
| --- | --- |
| Vapendavir (freebase) Capsules Lot# CLF13-113 - Kolliphor | 84% |
| Vapendavir (freebase) Capsules Lot# PS01-08 - Micronized API | 98% |
| Vapendavir (freebase) Capsules Lot# PS01-12 - Reduce Kolliphor | 88% |

The infinity point determination shows the formulation using the micronized vapendavir freebase releases to a greater extent than the formulation contain non-micronized material.

The dissolution rate and extent of vapendavir freebase solid oral formulations has been significantly increased over previously manufactured tablet formulations. The lead and back-up granulation formulations are listed below:

| Sample | Lead formulation | Backup formulation |
| --- | --- | --- |
| Vapendavir freebase (micronized) | 76.7% | 67.0% |
| Poloxamer (Kolliphor P188) | 14.5% | — |
| Sodium Starch Glycolate (Explotab) | 8.7% | 7.6% |
| Polysorbate 80 | — | 2.5% |
| Maltodextrin | — | 22.8% |

In accordance with the above tests, it was shown that the use of a wetting agent in the micronization process further assisted in obtaining a suitable and stable pharmaceutical composition with the crystalline free base vapendavir of the present invention.

Example 10: Assessment of Pre- and Post-Micronization XRPD Pattern

In accordance with the present invention, tests were conducted to confirm that the polymorph of the present crystalline free base vapendavir were the same following the micronization process identified above. In this regard, the pre- and post-micronization crystalline free base vapendavir compounds were tested under the following measurement conditions:

| | | | |
| --- | --- | --- | --- |
| X-Ray | 40 kV, 15 mA | Scan speed/ Duration time | 10.0000 deg/min |
| Goniometer | MiniFlex 300/600 | Step width | 0.0200 deg |
| Attachment | Standard | Scan axis | Theta/2-Theta |
| Filter | None | Scan range | 3.0000-90.0000 deg |
| CBO selection slit | — | Incident slit | 1.250 deg |
| Diffracted beam mono. | None | Length limiting slit | 10.0 mm |
| Detector | SC-70 | Receiving slit #1 | 1.250 deg |
| Scan mode | CONTINUOUS | Receiving slit #2 | 0.3 mm |

Figure 25:
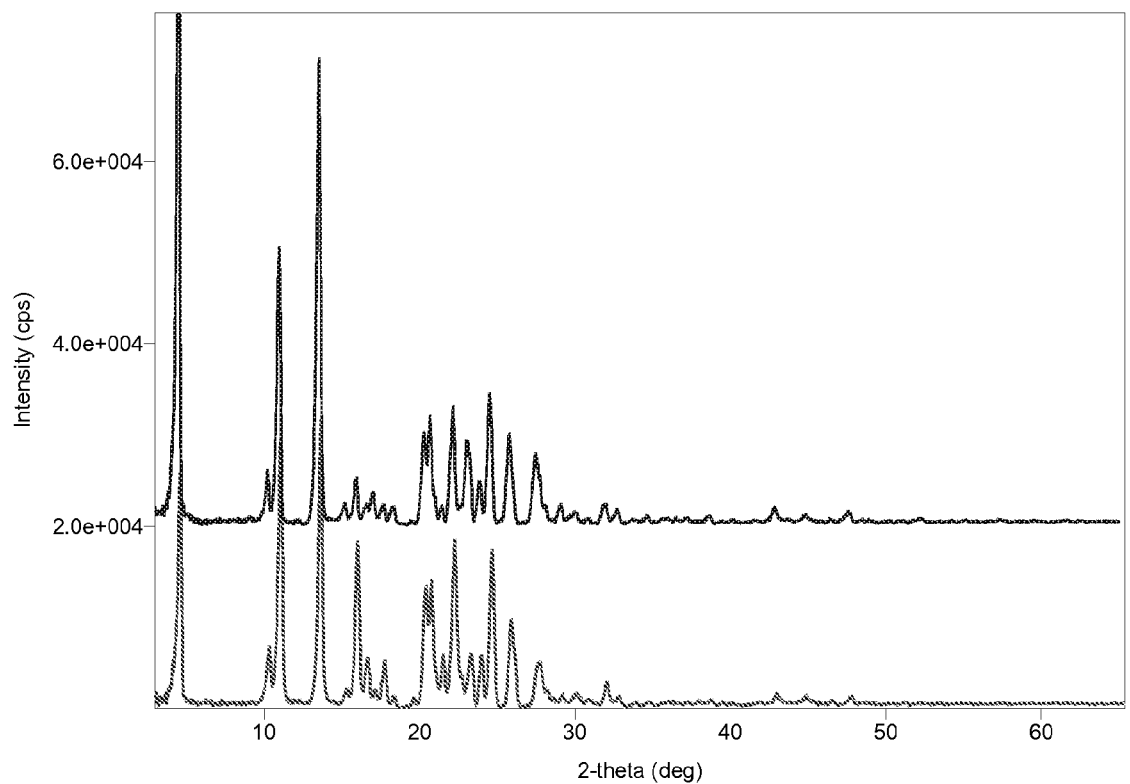
FIG. 25 shows an overlay of the XRDP patterns for the non-micronized and the micronized versions of the compounds of the invention.

The overlay of the XRDP patterns are shown in the graph in FIG. 25. As observed therein, the free-base polymorph is the same both pre- and post-micronization, and thus the polymorph of the present invention is very stable to mechanical processing.

What is claimed is:

1. A compound comprising an anhydrous crystalline free base form of 6-{2-[1-(6-methyl-3-pyridazinyl)-4-piperidinyl]ethoxy}-3-ethoxy-1,2-benzoxazole, wherein the crystalline free base form has a needle-like crystal habit.

2. The compound of claim 1, wherein the crystalline form has XRPD peaks (d-space, Å) selected from the group consisting of approximately the following values: 19.5, 8.0, 6.5, 4.4, 4.3, 4.0, 3.8, 3.6, and 3.5.

3. The compound of claim 1, wherein the crystalline form XRPD peaks (2θ) selected from the group consisting of the following approximate values: 4.5, 11.0, 13.6, 20.3, 20.6, 22.1, 23.1, 24.5, and 25.7.

4. The compound of claim 1, wherein the crystalline form has XRPD peaks (d-space, Å) selected from the group consisting of approximately the following values: 19.2, 8.5, 8.0, 6.5, 5.5, 5.3, 5.0, 4.35, 4.27, 4.12, 4.03, 3.99, 3.96, 3.80 and 3.60.

5. The compound of claim 1, wherein the crystalline form XRPD peaks (2θ) selected from the group consisting of the following approximate values: 4.6, 11.1, 13.7, 16.1, 20.4, 20.8, 22.3, and 24.8.

6. The compound of claim 1, wherein the crystalline form has XRPD peaks (2θ) selected from the group consisting of the following approximate values: 4.6, 10.4, 11.1, 13.7, 16.1, 16.7, 17.8, 20.4, 20.8, 21.6, 22.1, 22.3, 22.4, 23.4, and 24.8.

7. The compound of claim 1, wherein the crystalline form has the XRPD pattern shown in FIG. 1A, 1B, 2A, 2B or 3.

* * * * *